US012673952B2

(12) United States Patent
Bligh et al.

(10) Patent No.: US 12,673,952 B2
(45) Date of Patent: Jul. 7, 2026

(54) PROCESSES FOR PREPARING MODULATORS OF ALPHA-1 ANTITRYPSIN

(71) Applicant: Vertex Pharmaceuticals Incorporated, Boston, MA (US)

(72) Inventors: Cavan McKeon Bligh, Melrose, MA (US); Robert Daniel Giacometti, Malden, MA (US); Cristian Harrison, Beverly, MA (US); Stephen W. Laws, Dorchester, MA (US); Adam Looker, Newtonville, MA (US); Stefanie Roeper, Medford, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 459 days.

(21) Appl. No.: 18/018,245

(22) PCT Filed: Jul. 26, 2021

(86) PCT No.: PCT/US2021/043154
§ 371 (c)(1),
(2) Date: Jan. 26, 2023

(87) PCT Pub. No.: WO2022/026372
PCT Pub. Date: Feb. 3, 2022

(65) Prior Publication Data

US 2023/0279010 A1 Sep. 7, 2023

Related U.S. Application Data

(60) Provisional application No. 63/114,739, filed on Nov. 17, 2020, provisional application No. 63/080,877, filed on Sep. 21, 2020, provisional application No. 63/079,735, filed on Sep. 17, 2020, provisional application No. 63/056,958, filed on Jul. 27, 2020.

(51) Int. Cl.
*C07D 487/04* (2006.01)
*C07D 231/56* (2006.01)
*C07D 309/06* (2006.01)

(52) U.S. Cl.
CPC ......... *C07D 487/04* (2013.01); *C07D 231/56* (2013.01); *C07D 309/06* (2013.01)

(58) Field of Classification Search
CPC .................................................... C07D 487/04
See application file for complete search history.

(56) References Cited

U.S. PATENT DOCUMENTS

| | | | |
|---|---|---|---|
| 2,538,341 | A | 1/1951 | Ullyot |
| 2,612,503 | A | 9/1952 | Ullyot |
| 4,198,415 | A | 4/1980 | Kornfeld et al. |
| 4,647,667 | A | 3/1987 | Schaus et al. |
| 4,778,894 | A | 10/1988 | Schaus et al. |
| 5,216,001 | A | 6/1993 | Perregaard et al. |
| 5,358,949 | A | 10/1994 | Tabusa et al. |
| 6,201,129 | B1 | 3/2001 | Miller et al. |
| 11,623,924 | B2 | 4/2023 | Bandarage et al. |
| 11,884,672 | B2 | 1/2024 | Bandarage et al. |
| 12,331,057 | B2 | 6/2025 | Bandarage et al. |
| 2001/0051620 | A1 | 12/2001 | Berger et al. |
| 2003/0097000 | A1 | 5/2003 | Bovy et al. |
| 2003/0165712 | A1 | 9/2003 | Lin et al. |
| 2003/0212085 | A1 | 11/2003 | McCall et al. |
| 2004/0077865 | A1 | 4/2004 | Zhao et al. |
| 2005/0009754 | A1 | 1/2005 | Pan et al. |
| 2005/0043381 | A1 | 2/2005 | Johnson et al. |
| 2005/0153957 | A1 | 7/2005 | Cuenoud et al. |
| 2007/0027177 | A1 | 2/2007 | Trotter et al. |
| 2007/0232682 | A1 | 10/2007 | Beard et al. |
| 2007/0248947 | A1 | 10/2007 | Cezar |
| 2008/0021056 | A1 | 1/2008 | Konradi et al. |
| 2010/0016285 | A1 | 1/2010 | Uchida et al. |
| 2010/0076018 | A1 | 3/2010 | Liu et al. |
| 2011/0118221 | A1 | 5/2011 | Von Nussbaum et al. |
| 2013/0167932 | A1 | 7/2013 | Maeda et al. |
| 2013/0319530 | A1 | 12/2013 | Maeda et al. |
| 2014/0135359 | A1 | 5/2014 | Martineau |
| 2014/0341899 | A1 | 11/2014 | Dinarello et al. |
| 2016/0083363 | A1 | 3/2016 | Hamm et al. |
| 2016/0145271 | A1 | 5/2016 | Vakalopoulos et al. |
| 2018/0251460 | A1 | 9/2018 | Aktoudianakis et al. |
| 2020/0361939 | A1 | 11/2020 | Bandarage et al. |

(Continued)

FOREIGN PATENT DOCUMENTS

| | | | |
|---|---|---|---|
| CA | 3114672 | A1 | 4/2020 |
| CN | 1704404 | A | 7/2001 |

(Continued)

OTHER PUBLICATIONS

Al-Shaar et al. The Synthesis of Heterocycles via Addition-Elimination Reactions of 4- and 5-aminoimidazoles. J. Chern. Soc. Perkin Trans. 1 (1992).

Carta et al. Reactions of Alkylation of Biologically Interesting triazolo[4,5-g]quinolines and triazolo[4,5-g]quinoline-1-oxides with Electrophilic Reagents. Heterocycles 75(10) 2493-2505 (2008).

Chemical Abstracts Service, CAS Registry No. 2255-53-0. CA Index Name: Carbostyril, 3-ethyl-8-hydroxy-4-methoxy-(8CI) Date: Nov. 16, 1984.

Chemical Abstracts Service, CAS Registry No. 56513-01-0. CA Index Name: 8-Hydroxy-3-methyl-1(2H)-isoquinolinone, Date: Nov. 16, 1984.

(Continued)

*Primary Examiner* — Benjamin J Packard
(74) *Attorney, Agent, or Firm* — Finnegan, Henderson, Farabow, Garrett & Dunner, LLP

(57) ABSTRACT

This disclosure provides large-scale processes for preparing a modulator of alpha-1 antitrypsin (AAT) activity that may be useful for treating alpha-1 antitrypsin deficiency (AATD), such as 4-(5-(4-fluorophenyl)-6-(tetrahydro-2H-pyran-4-yl)-1,5-dihydropyrrolo[2,3-f]indazol-7-yl)benzoic acid (Compound 1), 3-[5-(4-fluorophenyl)-6-isopropyl-1H-pyrrolo[2,3-f]indazol-7-yl]propanoic acid (Compound 2), or a pharmaceutically acceptable salt of any of the foregoing.

5 Claims, No Drawings

(56) References Cited

U.S. PATENT DOCUMENTS

| | | | |
|---|---|---|---|
| 2021/0260036 | A1 | 8/2021 | Bozic et al. |
| 2023/0157999 | A1 | 5/2023 | Clark et al. |
| 2023/0159502 | A1 | 5/2023 | Giroux et al. |
| 2023/0159504 | A1 | 5/2023 | Giroux et al. |
| 2023/0159521 | A1 | 5/2023 | Giroux et al. |
| 2023/0159580 | A1 | 5/2023 | Giroux et al. |
| 2023/0265080 | A1 | 8/2023 | Bandarage et al. |
| 2023/0339915 | A1 | 10/2023 | Giroux et al. |
| 2024/0002386 | A1 | 1/2024 | Shi et al. |
| 2024/0012010 | A1 | 1/2024 | Penney et al. |
| 2024/0158404 | A1 | 5/2024 | Grey, Jr. et al. |
| 2024/0336614 | A1 | 10/2024 | Bandarage et al. |

FOREIGN PATENT DOCUMENTS

| | | | |
|---|---|---|---|
| CN | 1505613 | A | 6/2004 |
| CN | 102850324 | A | 1/2013 |
| CN | 103239451 | | 8/2013 |
| CN | 107698505 | A | 2/2018 |
| CN | 109414596 | A | 3/2019 |
| CN | 110776459 | A | 2/2020 |
| CN | 113164761 | A | 7/2021 |
| CN | 115361946 | A | 11/2022 |
| EP | 0 465 398 | A2 | 1/1992 |
| EP | 1 396 488 | A1 | 3/2004 |
| EP | 3571187 | B1 | 11/2019 |
| EP | 3 699 179 | A1 | 8/2020 |
| ES | 323287 | A1 | 3/1967 |
| JP | 4856667 | A | 8/1973 |
| JP | 2000-072751 | A | 3/2000 |
| JP | 2000-281654 | A | 10/2000 |
| JP | 5107589 | B2 | 12/2012 |
| RU | 2337915 | C1 | 11/2008 |
| RU | 2617405 | C2 | 4/2017 |
| WO | WO 1996/037467 | A1 | 11/1996 |
| WO | WO 00/35919 | | 6/2000 |
| WO | WO 2000/075114 | A1 | 12/2000 |
| WO | WO 2001/044197 | A2 | 6/2001 |
| WO | WO 2002/008224 | A1 | 1/2002 |
| WO | WO 2002/094790 | A1 | 11/2002 |
| WO | WO 2003/099824 | A1 | 12/2003 |
| WO | WO 2004/065367 | A1 | 8/2004 |
| WO | WO 2004/108120 | A1 | 12/2004 |
| WO | WO 2006/019831 | A1 | 2/2006 |
| WO | WO 2006/093823 | A1 | 9/2006 |
| WO | WO 2007/022501 | A2 | 2/2007 |
| WO | WO 2007/115315 | A2 | 10/2007 |
| WO | WO 2009/060209 | A1 | 5/2009 |
| WO | WO 2009/127686 | A1 | 10/2009 |
| WO | WO 2009/158587 | A1 | 12/2009 |
| WO | WO 2011/056222 | A1 | 5/2011 |
| WO | WO 2011/110852 | A1 | 9/2011 |
| WO | WO 2012/016695 | A2 | 2/2012 |
| WO | WO 2012/038820 | A2 | 3/2012 |
| WO | WO 2016/154051 | A1 | 9/2016 |
| WO | WO 2017/035418 | A1 | 3/2017 |
| WO | WO 2017/117304 | A1 | 7/2017 |
| WO | WO 2017/197240 | A1 | 11/2017 |
| WO | WO 2017/207118 | A1 | 12/2017 |
| WO | WO 2018/218192 | A1 | 11/2018 |
| WO | WO 2019/076336 | A1 | 4/2019 |
| WO | WO 2019/089667 | A1 | 5/2019 |
| WO | WO 2019/116302 | A1 | 6/2019 |
| WO | WO 2019/149522 | A1 | 8/2019 |
| WO | WO 2019/243841 | A1 | 12/2019 |
| WO | WO 2020/002611 | A1 | 1/2020 |
| WO | WO 2020/033288 | A1 | 2/2020 |
| WO | WO 2020/048694 | A1 | 3/2020 |
| WO | WO 2020/081257 | A1 | 4/2020 |
| WO | WO 2020/247160 | A1 | 12/2020 |
| WO | WO 2021/067584 | A1 | 4/2021 |
| WO | WO 2021/155087 | A1 | 8/2021 |
| WO | WO 2021/203007 | A1 | 10/2021 |
| WO | WO 2021/203010 | A1 | 10/2021 |
| WO | WO 2021/203014 | A1 | 10/2021 |
| WO | WO 2021/203023 | A1 | 10/2021 |
| WO | WO 2021/203025 | A1 | 10/2021 |
| WO | WO 2021/203028 | A1 | 10/2021 |
| WO | WO 2022/026372 | A2 | 2/2022 |
| WO | WO 2022/104353 | A1 | 5/2022 |
| WO | WO 2022/109553 | A2 | 5/2022 |
| WO | WO 2024/054624 | A1 | 3/2024 |

OTHER PUBLICATIONS

Chemical Abstracts Service, CAS Registry No. 73109-03-2. CA Index Name: 7-Hydroxy-3-methyl-2-phenyl-1(2H)-isoquinolinone, Date: Nov. 16, 1984.

Chemical Abstracts Service, CAS Registry No. 73828-43-0. CA Index Name: 1(2H)-Isoquinolinone, 3-ethyl-7-hydroxy—Date: Nov. 16, 1984.

Chemical Abstracts Service, CAS Registry No. 73828-46-3. CA Index Name: 1(2H)-Isoquinolinone, 3-ethyl-7-hydroxy-2-methyl—Date: Nov. 16, 1984.

Chemical Abstracts Service, CAS Registry No. 73828-51-0. CA Index Name: 7-Hydroxy-2-(2-hydroxyethyl)-3-methyl-l(2H)-isoquinolinone. Date: Nov. 16, 1984.

Chemical Abstracts Service, CAS Registry No. 73828-52-1. CA Index Name: 1(2H)-Isoquinolinone, 3-ethyl-7-hydroxy-2-(2-hydroxyethyl)—Date: Nov. 16, 1984.

Chemical Abstracts Service, CAS Registry No. 73828-55-4. CA Index Name: 1(2H)-Isoquinolinone, 3-ethyl-2,7-dihydroxy—Date: Nov. 16, 1984.

Chemical Abstracts Service, CAS Registry No. 91348-44-6. CA Index Name: 3-(2-Bromoethyl)-8-hydroxy-2(1H)-quinolinone. Date: Nov. 16, 1984.

Chemical Abstracts Service, CAS Registry No. 872787-19-4. CA Index Name: 1(2H)-Isoquinolinone, 7-amino-3-ethyl—Date: Jan. 27, 2006.

Chemical Abstracts Service, CAS Registry No. 102559-86-4. CA Index Name: 8-Quinolinol, 4-chloro-2-[2-(diethylamino)ethyl]-3-ethyl—Date: Jun. 7, 1986.

Chemical Abstracts Service, CAS Registry No. 1045710-22-2. CA Index Name: 8-Quinolinol, 3-(1-methylethyl)-2-(2-methylpropyl)—Date: Sep. 2, 2008.

Chemical Abstracts Service, CAS Registry No. 105909-75-9. CA Index Name: 8-Quinolinol, 3-ethyl-2-methyl—Date: Dec. 25, 1986.

Chemical Abstracts Service, CAS Registry No. 1078095-05-2. CA Index Name: 8-Quinolinol, 3-ethyl-2-phenyl—Date: Dec. 1, 2008.

Chemical Abstracts Service, CAS Registry No. 1780592-67-7. CA Index Name: 2-(7-hydroxy-2-methoxyquinolin-3-yl)acetic acid. Date: Jun. 15, 2015.

Chemical Abstracts Service, CAS Registry No. 1785114-56-8. CA Index Name: 7-Hydroxy-3-methyl-I-isoquinolinecarboxylic acid. Date: Jun. 21, 2015.

Chemical Abstracts Service, CAS Registry No. 1854272-23-3. CA Index Name: 4-Chloro-3-ethyl-2-methyl-8-(phenylmethoxy)quinoline Date: Jan. 28, 2016.

Chemical Abstracts Service, CAS Registry No. 1869801-41-1. CA Index Name: 3-Ethyl-N-methyl-7-(phenylmethoxy)-2-quinolinamine Date: Feb. 18, 2016.

Chemical Abstracts Service, CAS Registry No. 1873904-99-4. CA Index Name: 4-Chloro-3-ethyl-2-methyl-7-(phenylmethoxy)quinoline Date: Feb. 25, 2016.

Chemical Abstracts Service, CAS Registry No. 1875846-68-6. CA Index Name: N,3-Diethyl-7-(phenylmethoxy)-2-quinolinamine Date: Feb. 29, 2016.

Chemical Abstracts Service, CAS Registry No. 1877816-72-2. CA Index Name: N-Methyl-3-(1-methylethyl)-7-(phenylmethoxy)-2-quinolinamine Date: Mar. 2, 2016.

Chemical Abstracts Service, CAS Registry No. 1878025-01-4. CA Index Name: 4-Chloro-2-methyl-3-(1-methylethyl)-7-(phenylmethoxy)quinoline Date: Mar. 2, 2016.

Chemical Abstracts Service, CAS Registry No. 1880486-29-2. CA Index Name: 4-Chloro-2-methyl-3-(1-methylethyl)-8-(phenylmethoxy)quinoline Date: Mar. 6, 2016.

Chemical Abstracts Service, CAS Registry No. 1893503-08-6. CA Index Name: 1,2-Dihydro-8-hydroxy-1-methyl-2-oxo-3-

(56) References Cited

OTHER PUBLICATIONS quinolineacetic acid Date: Apr. 20, 2016.
Chemical Abstracts Service, CAS Registry No. 1936181-19-9. CA Index Name: 8-Hydroxy-3-(hydroxymethyl)-1(2H)-isoquinolinone Date: Jun. 21, 2016.
Chemical Abstracts Service, CAS Registry No. RN 2106364-27-4. Index Name: Pyrrolo[2,3-f]benzimidazole-7-carboxylic acid, 3,5-dihydro-2,5,6-trimethyl-, ethyl ester Date: Aug. 1, 2017.
Chemical Abstracts Service, CAS Registry No. RN 2137577-83-2. Index Name: 7-Hydroxy-3-(methylamino)-1(2H)-isoquinolinone, Date: Nov. 1, 2017.
Fujisawa, T. (1959) "Studies on the Utilisation of Safrole as Medicinal Raw Materials XII. Synthesis of Indole Derivatives" Journal of the Pharmaceutical Society of Japan, 79(6): 778-783.
International Search Report and Written Opinion from International Application No. PCT/US2025/019485, mailed Jul. 2, 2025 (10 pages).
Jiang, B. et al. (2011) "A multi-component domino reaction for the direct access to polyfunctionalized indolesvia intermolecular allylic esterification and indolation," Chem. Commun., 2012,48,808-810.
Kapetanovic IM. (2008). Computer-aided drug discovery and development (CADDD): in silico-chemico-biological approach. Chem Biol Interact. 30;171(2):165-76.
Kathuria, A. et al. (2011). Substrate specificity of acetoxy derivatives of coumarins and quinolones towards Calreticulin mediated transacetylation: Investigations on antiplatelet function. Bioorganic & Medicinal Chemistry, vol. 20: 1624-1638.
Khusnutdinov, R. et al. (2015), "Quinoline Synthesis by the Reaction of Anilines with 1,2-diols Catalyzed by Iron Compounds," J. Heterocyclic Chem., vol. 53: 1022-1029.
Liu, M. et al. (2016) "Synthesis and Antifungal Activities of Novel Strobilurin Derivatives Containing Quinolin-2(1H)-one Moiety," Chem. Res. Chin. Univ., 32(4): 600-606.
Lyubchanskaya, V. M. et al., Nenitzescu synthesis of derivatives of 5-hydroxybenzofuran and 5- and 6-hydroxyindoles, Khimiko-Farmatsevtichesik Zhurnal, 1992, 26(9-10), 108-112.
Modi, A. R. et al., "Synthesis of 3-Methyl, 3-Formyl & Other 3-Substituted N-Arylisoquinolones", Indian Journal of Chemistry, 1979, vol. 18B, pp. 304-306.
Modi, A. R. et al., "Synthesis of 7-hydroxy-3-alkylisoquinolones and 7-hydroxy-3-alkylisocoumarins from 4-hydroxyhomophthalic acid", Indian Journal of Chemistry, 1979, vol. 17B, No. 4, pp. 360-363.
Priya, N. et al. (2010) "Characterization of 4-methyl-2-oxo-1,2-dihydroquinolin-6-yl acetate as an effective antiplatelet agent," Bioorganic & Medicinal Chemistry, vol. 18: 4085-4094.
Stoller, J.K. "Alpha-1 antitrypsin deficiency: An underrecognized, treatable cause of COPD." *Cleve Clin J Med* 83, No. 7 (2016): 507-14.
U.S. Appl. No. 18/630,559, filed Apr. 9, 2024, by Bozic et al.
Xu, M. et al, Facile Assembly of 11H-Indolo[3,2-c]quinoline by a Two-Step Protocol Involving a Regioselective 6-endo-Cyclization Promoted by the Hendrickson Reagent, Synthesis 2011, No. 4, pp. 0626-0634.
American Thoracic Society & European Respiratory Society (2003) "American Thoracic Society/European Respiratory Society Statement: Standards for the Diagnosis and Management of Individuals with Alpha-1 Antitrypsin Deficiency," *Am J Respir Crit Care Med.*, 168:818-900.
Akhapkina, V.I. et al. (2012) "Fundamental bases of modulatory concept and classification of modulatory drugs", Russian Medical Journal, 19: 933-951.
Aldonyte Ruta et al: "Analysis of systemic biomarkers in COPD patients", COPD: Journal of Chronic Obstructive Pulmonary Disease, Informa Healthcare, US, vol. 1, No. 2, Jan. 1, 2004 (Jan. 1, 2004), pp. 155-164.
Balle, T. et al. (2003) "Synthesis and Structure-Affinity Relationship Investigations of 5-Aminomethyl and 5-Carbamoyl Analogues of the Antipsychotic Sertindole. A New Class of Selective $\alpha_1$ Adrenoceptor Antagonists," Bioorg. Med. Chem., 11:1065-1078.
Belikov, V.G. (2007) "Pharmaceutical Chemistry", textbook, Moscow, MEDpress-inform, pp. 27-29.
Bergin, D.A. et al. (2014) "The circulating proteinase inhibitor alpha-1 antitrypsin regulates neutrophil degranulation and autoimmunity," *Sci Transl Med.*, 6(217):217ra1 (70 pages).
Chemical Abstracts Service, CAS Registry No. 1516110-75-0. CA Index Name: Pyrrolo[2,3-f]benzimidazole-7-methanamine, 6-ethyl-3,5-dihydro-2-methyl-6-Ethyl-3,5-dihydro-2-methylpyrrolo[2,3-f]benzimidazole-7-methanamine Date: Jan. 10, 2014.
Chemical Abstracts Service, CAS Registry No. 2103889-64-9. CA Index Name: Pyrrolo[2,3-f]benzimidazole-7-carbonitrile, 3,5-dihydro-2,5,6-trimethyl Date: Jul. 27, 2017.
Chou, T.-C. (2010) "Drug Combination Studies and Their Synergy Quantification Using the Chou-Talalay Method", Cancer Res; 70(2):440-446.
Dafforn, T. R. et al: "A kinetic mechanism for the polymerization of alpha1-antitrypsin", The Journal of Biological Chemistry, vol. 274, No. 4, Apr. 2, 1999 (Apr. 2, 1999), pp. 9548-9555.
Donawade, D.S. et al. (Apr. 2007) "Synthesis and antimicrobial activity of novel linearly fused 5-substituted-7-acetyl-2,6-dimethyloxazolo[4,5-f] indoles," *Indian Journal of Chemistry*, 46B:690-693.
Eggenschwiler, R. et al: "Sustained Knockdown of a DiseaseCausing Gene in Patient-Specific Induced Pluripotent Stem Cells Using Lentiviral Vector-Based Gene Therapy", Stem Cells Translational Medicine, vol. 2, No. 9, Sep. 1, 2013 (Sep. 1, 2013), pp. 641-654.
Forbes, I.T. et al. (1996) "Synthesis, Biological Activity, and Molecular Modeling Studies of Selective 5-$HT_{2C/2B}$ Receptor Antagonists," *J. Med. Chem.*, 39:4966-4977.
Ferrarotti, I. et al: "Quantification of circulating alpha-1-antitrypsin polymers in dried blood spots", Molecular Pathology and Funct. Genomics, vol. 56, Sep. 7, 2020 (Sep. 7, 2020), p. 326.
Fregonese, F. & J. Stolk (2008) "Hereditary alpha-1-antitrypsin deficiency and its clinical consequences," *Orphanet J. Rare Dis.*, 3:16 (9 pages).
Geraghty, P. et al. (Dec. 2014), "$\alpha$1-Antitrypsin Activates Protein Phosphatase 2A to Counter Lung Inflammatory Responses," *Am J Respir Crit Care Med*, 190(11):1229-1242.
Grant & Hackh's Chemical Dictionary (5th ed. 1987), at p. 148.
Grinev, A.N. et al. (1975), "Synthesis of Aldehydes and Nitriles in the 5-Hydroxyindole Series," *Chem. Heterocycl. Compd.*, 11:1087-1090.
Gadaginamath, G.S. et al. (2000) "Chemoselective Reaction of 3,6-Diacetylindole Towards Hydroxylamine: Synthesis and Antimicrobial Activity of Novel Isoxazolo[4,5-f]indole Derivatives," *Rev. Roum. Chim.*, 45(10):929-933.
Ghorai, J. et al. (2016) "Cobalt(III)-Catalyzed Intramolecular Cross-Dehydrogenative C-H/X-H Coupling: Efficient Synthesis of Indoles and Benzofurans," *Chem. Eur. J.*, 22:16042-16046.
Ghorai, J. et al. (2018) "Divergent Functionalization of N-Alkyl-2-alkenylanilines: Efficient Synthesis of Substituted Indoles and Quinolines," *Chem. Asian J.*, 13(17):2499-2504.
Gosai, S. et al. (Nov. 2010) "Automated High-Content Live Animal Drug Screening Using C. elegans Expressing the Aggregation Prone Serpin al-antitrypsin Z," *PLoS One*, 5(11):e15460 (16 pages).
Harkevich, D.A. (2010) Pharmacology/Textbook, 10th edition, pp. 72-82.
He, L. et al. (2014) "Transition-metal-free synthesis of multisubstituted N-arylindoles via reaction of arynes and $\alpha$-amino ketones," *Tetrahedron*, 70:2400-2405.
International Search Report and Written Opinion for International Application No. PCT/US2019/054681, mailed Mar. 30, 2020 (14 pages).
International Search Report and Written Opinion for International Application No. PCT/US2020/032832, mailed Oct. 27, 2020 (17 pages).
International Search Report and Written Opinion for International Application No. PCT/US2020/053777, mailed Mar. 4, 2021 (11 pages).
International Search Report and Written Opinion for International Application No. PCT/US2021/015614, mailed Apr. 29, 2021 (9 pages).

(56) References Cited

OTHER PUBLICATIONS

International Search Report and Written Opinion from International Application No. PCT/US2021/025597, mailed Jun. 14, 2021 (12 pages).
International Search Report and Written Opinion for International Application No. PCT/US2021/025601, mailed Jun. 15, 2021 (13 pages).
International Search Report and Written Opinion from International Application No. PCT/US2021/025614, mailed Jun. 16, 2021 (14 pages).
International Search Report and Written Opinion from International Application No. PCT/US2021/025616, mailed Jun. 14, 2021 (12 pages).
International Search Report and Written Opinion from International Application No. PCT/US2021/025623, mailed Jun. 14, 2021 (18 pages).
International Search Report and Written Opinion from International Application No. PCT/US2021/043154, mailed Feb. 4, 2022 (21 pages).
International Search Report and Written Opinion from International Application No. PCT/US2021/072352, mailed Apr. 25, 2022 (25 pages).
International Search Report and Written Opinion from International Application No. PCT/US2021/072451, mailed May 24, 2022 (19 pages).
Jafarpour, F. et al. (2019) "A Fast Track to Indoles and Annulated Indoles through *ortho- vs ipso*-Amination of Aryl Halides," *Org. Lett.*, 21:10143-10148.
Jiang, H. et al. (2016) "Multiple Roles of the Pyrimidyl Group in the Rhodium-Catalyzed Regioselective Synthesis and Functionalization of Indole-3-carboxylic Acid Esters," *Advanced Synthesis & Catalysis*, 358:188-194.
Kamat, A.G. et al. (Mar. 1994), "Synthesis and Antimicrobial Activity of Furoindole Derivatives," *Indian J. Chem. Sect. B*, 33B(3):255-259.
Kummerer, K. (2010) "Pharmaceuticals in the environment", Annual Review of Environment and Resources, 35:57-75.
Kuznetsova, G.A. (2005) "Methodological instructions", Irkutsk State University, Department of General Physics, pp. 2-3.
Laffranchi, M. et al: "Heteropolymerization of [alpha]-1-antitrypsin mutants in cell models mimicking heterozygosity", Human Molecular Genetics, vol. 27, No. 10, Mar. 10, 2018 (Mar. 10, 2018), pp. 1785-1793.
Maity, S. et al. (Sep. 2012) "A Visible-Light-Mediated Oxidative C—N Bond Formation/Aromatization Cascade: A New Photocatalytic Preparation of N-Arylindoles," *Angew Chem Int Ed Engl.*, 51(38):9562-9566. NIH Public Access Author Manuscript; available in PMC Sep. 17, 2013 (11 pages).
Mali, R.S. et al. (1994) "Useful Syntheses of Pyrano- and Pyridoindoles," *Organic Preparations and Procedures International: The New Journal for Organic Synthesis*, 26(5):573-577.
Mashkovsky (2001) M.D. Drugs, 14th edition, Moscow, 1:11.
Meti, P. et al. (2017) "Regioselective synthesis of dipyrrolopyrazine (DPP) derivatives via metal free and metal catalyzed amination and investigation of their optical and thermal properties," *RSC Adv.*, 7:18120-18131.
Notice of Allowance and Fee(s) Due for U.S. Appl. No. 15/931,256, mailed Jul. 17, 2023.
Ogushi, F. et al. (1987) "Z-type α1-antitrypsin is less competent than M1-type α1-antitrypsin as an inhibitor of neutrophil elastase," *J Clin Invest.*, 80(5):1366-1374.
Piitulainen, E. & H.A. Tanash (2015), "The Clinical Profile of Subjects Included in the Swedish National Register on Individuals with Severe Alpha 1-Antitrypsin deficiency," *COPD*, 12(S1):36-41.
Saccarello, M.L. et al. (Sep. 1979) "A New Synthesis of 1-Alkyl-3-aminoindoles," *Synthesis*, 1979(9):727-729.
Song, X. et al. (2018) "Regioselective Synthesis of 2-Alkenylindoles and 2-Alkenylindole-3-carboxylates through the Cascade Reactions of N-Nitrosoanilines with Propargyl Alcohols," *J. Org. Chem.*, 83:8509-8521.
Tanash, H.A. et al. (2016) "Cause-specific mortality in individuals with severe alpha 1-antitrypsin deficiency in comparison with the general population in Sweden," *International Journal of COPD*, 2016(11):1663-1669.
Tidwell, R.R. et al. (1978) "Diarylamidine Derivatives with One or Both of the Aryl Moieties Consisting of an Indole or Indole-like Ring. Inhibitors of Arginine-Specific Esteroproteases," J Med Chem, vol. 21, No. 7:613-623.
U.S. Appl. No. 17/060,945, filed Oct. 1, 2020, by Bozic et al.
U.S. Appl. No. 17/916,388, filed Sep. 30, 2022, by Giroux et al.
U.S. Appl. No. 18/036,491, filed May 11, 2023, by Penney et al.
U.S. Appl. No. 18/037,121, filed May 16, 2023, by Shi et al.
*Vertex Provides Update on its Clinical Programs Targeting Alpha-1 Antitrypsin Deficiency*, Vertex (Oct. 14, 2020), https://news.vrtx.com/press-release/vertex-provides-update-its-clinical-programs-targeting-alpha-1-antitrypsin-deficiency (4 pages).
*Vertex Announces Primary Endpoint Achieved in Phase 2 Study of VX-864 in Alpha-1 Antitrypsin Deficiency*, Vertex (Jun. 10, 2021), https://news.vrtx.com/press-release/vertex-announces-primary-endpoint-achieved-phase-2-study-vx-864-alpha-1-antitrypsin (5 pages).
Wen, W. et al. (2014) "Substituted indoles as selective protease activated receptor 4 (PAR-4) antagonists: Discovery and SAR of ML354," *Bioorg. Med. Chem. Lett.*, http://dx.doi.org/10.1016/j.bmcl.2014.08.021.
Yu-Liang, L. et al. (2017) "Diagnosis and Treatment of α1-Antitrypsin Deficiency," Practical Clinical Medicine, 18(2): 104-107.
Zorgdrager, J. et al. (1989) "Synthesis of indoles using (N-arylaminomethyl)diphenylphosphine oxides," *Recueil des Travaux Chimiques des Pays-Bas*, vol. 108, No. 12, pp. 441-444.

PROCESSES FOR PREPARING MODULATORS OF ALPHA-1 ANTITRYPSIN

This application claims the benefit of priority of U.S. Provisional Application No. 63/056,958, filed Jul. 27, 2020, U.S. Provisional Application No. 63/079,735, filed Sep. 17, 2020, U.S. Provisional Application No. 63/080,877, filed Sep. 21, 2020, and U.S. Provisional Application No. 63/114,739, filed Nov. 17, 2020, the contents of each of which are incorporated by reference herein in their entireties.

This disclosure provides processes for preparing modulators of alpha-1-antitrypsin (AAT) activity that may be useful in the treatment of alpha-1 antitrypsin deficiency (AATD), including 4-(5-(4-fluorophenyl)-6-(tetrahydro-2H-pyran-4-yl)-1,5-dihydropyrrolo[2,3-f]indazol-7-yl)benzoic acid (Compound 1), such as, for example, solid forms of Compound 1, 3-[5-(4-fluorophenyl)-6-isopropyl-1H-pyrrolo[2,3-f]indazol-7-yl]propanoic acid (Compound 2), such as, for example, solid forms of Compound 2, and pharmaceutically acceptable salts of any of the foregoing.

AATD is a genetic disorder characterized by low circulating levels of AAT. While treatments for AATD exist, there is currently no cure. AAT is produced primarily in liver cells and secreted into the blood, but it is also made by other cell types, including lung epithelial cells and certain white blood cells. AAT inhibits several serine proteases secreted by inflammatory cells (most notably neutrophil elastase [NE], proteinase 3, and cathepsin G) and thus protects organs such as the lungs from protease-induced damage, especially during periods of inflammation.

The mutation most commonly associated with AATD involves a substitution of lysine for glutamic acid (E342K) in the SERPINA1 gene that encodes the AAT protein. This mutation, known as the Z mutation or the Z allele, leads to misfolding of the translated protein, which is therefore not secreted into the bloodstream and can polymerize within the producing cell. Consequently, circulating AAT levels in individuals homozygous for the Z allele (PiZZ) are markedly reduced; only approximately 15% of mutant Z-AAT protein folds correctly and is secreted by the cell. An additional consequence of the Z mutation is that the secreted Z-AAT has reduced activity compared to wild-type protein, exhibiting 40% to 80% of normal anti-protease activity (American thoracic society/European respiratory society, Am J Respir Crit Care Med. 2003; 168(7):818-900; and Ogushi et al. J Clin Invest. 1987; 80(5):1366-74).

The accumulation of polymerized Z-AAT protein within hepatocytes results in a gain-of-function cytotoxicity that can result in cirrhosis or liver cancer later in life and neonatal liver disease in 12% of patients. This accumulation may spontaneously remit but can be fatal in a small number of children. The deficiency of circulating AAT results in unregulated protease activity that degrades lung tissue over time, resulting in emphysema, a form of chronic obstructive pulmonary disease (COPD). This effect is severe in PiZZ individuals and typically manifests in middle age, resulting in a decline in quality of life and shortened lifespan (mean: 68 years of age) (Tanash et al. Int J Chron Obstruct Pulm Dis. 2016; 11:1663-9). The effect is more pronounced in PiZZ individuals who smoke, resulting in an even further shortened lifespan (58 years) (Piitulainen and Tanash, COPD 2015; 12(1):36-41). PiZZ individuals account for the majority of those with clinically relevant AATD lung disease. Accordingly, there is a need for additional and effective treatments for AATD.

A milder form of AATD is associated with the SZ genotype in which the Z-allele is combined with an S-allele. The S allele is associated with somewhat reduced levels of circulating AAT but causes no cytotoxicity in liver cells. The result is clinically significant lung disease but not liver disease (Fregonese and Stolk, Orphanet J Rare Dis. 2008; 33:16). As with the ZZ genotype, the deficiency of circulating AAT in subjects with the SZ genotype results in unregulated protease activity that degrades lung tissue over time and can result in emphysema, particularly in smokers.

The current standard of care for AAT deficient individuals who have or show signs of developing significant lung or liver disease is augmentation therapy or protein replacement therapy. Augmentation therapy involves administration of a human AAT protein concentrate purified from pooled donor plasma to augment the missing AAT. Although infusions of the plasma protein have been shown to improve survival or slow the rate of emphysema progression, augmentation therapy is often not sufficient under challenging conditions (such as, for example, during an active lung infection). Similarly, although protein replacement therapy shows promise in delaying progression of disease, augmentation does not restore the normal physiological regulation of AAT in patients and efficacy has been difficult to demonstrate. In addition, augmentation therapy requires weekly visits for treatment and cannot address liver disease, which is driven by the toxic gain-of-function of the Z allele. Thus, there is a continuing need for new and more effective treatments for AATD.

4-(5-(4-fluorophenyl)-6-(tetrahydro-2H-pyran-4-yl)-1,5-dihydropyrrolo[2,3-f]indazol-7-yl)benzoic acid or Compound 1 is disclosed in International Patent Application No. PCT/US2020/032832, published as International Patent Application Publication No. WO 2020/247160 (incorporated herein by reference in its entirety), as a potent modulator of AAT activity for treatment of AATD:

(Compound 1)

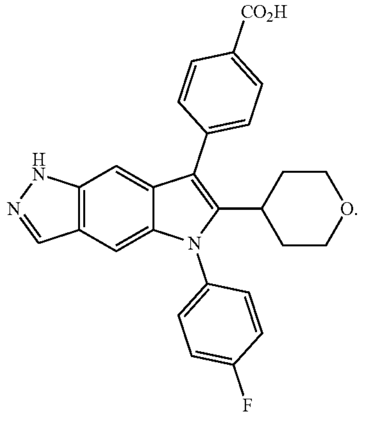

WO 2020/247160 also describes synthesis processes for Compound 1 and pharmaceutically acceptable salts thereof.

Additionally, 3-[5-(4-fluorophenyl)-6-isopropyl-1H-pyrrolo[2,3-f]indazol-7-yl]propanoic acid or Compound 2 is disclosed in International Patent Application No. PCT/US2019/054681, published as International Patent Application Publication No. WO 2020/081257 (incorporated herein by reference in its entirety), as a potent modulator of AAT activity for treatment of AATD:

(Compound 2)

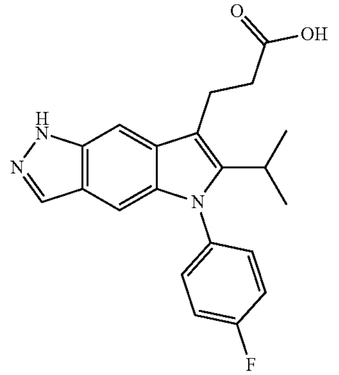

WO 2020/081257 also describes synthesis processes for Compound 2 and pharmaceutically acceptable salts thereof.

As medical uses of Compound 1 and Compound 2 are further studied, a need exists for alternative synthesis processes for each compound that are capable of producing large batches of the compound or a pharmaceutically acceptable salt thereof, so as to support clinical studies conducted at multiple locations, each with large populations of subjects. Such large-scale synthesis processes would also be useful if either compound is approved for the treatment of AATD and becomes accessible to the patient population public.

It is generally appreciated in the pharmaceutical industry that scaling up drug manufacturing from milligram levels to mass manufacturing in kilogram levels is not a simple, linear process. Common issues encountered when drug manufacturing is scaled up include formation of new impurities, different impurity profiles, and changes in polymorphic forms. It is plausible that if the manufacturing of a drug cannot be successfully scaled up, then the drug may never reach the market even if it has secured regulatory approval.

This disclosure addresses unmet needs by providing synthesis processes that are capable of producing large batches of Compound 1 or a pharmaceutically acceptable salt thereof (e.g., 100 kg and above) and are compliant with current GMP (Good Manufacturing Practices) guidelines. This disclosure also provides alternative syntheses of a solid form of Compound 1 or a pharmaceutically acceptable salt thereof, as well as alternative processes for preparing intermediates employed in the synthesis of Compound 1.

Additionally, this disclosure addresses unmet needs by providing synthesis processes that are capable of producing large batches of Compound 2 or a pharmaceutically acceptable salt thereof (e.g., 100 kg and above) and are compliant with current GMP (Good Manufacturing Practices) guidelines. This disclosure also provides an alternative synthesis of a solid form of Compound 2 or a pharmaceutically acceptable salt thereof.

DETAILED DESCRIPTION

Definitions

As used herein, the term "solid form" includes any solid form of a compound, such as Compound 1 or Compound 2, including a substantially crystalline form, a crystalline form, an amorphous form, a solid dispersion, a solvate, a cocrystal, or a salt of the compound that is in solid form. A crystalline form is a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, solid state nuclear magnetic resonance (SSNMR), differential scanning calorimetry (DSC), dynamic vapor sorption (DVS), and/or thermogravimetric analysis (TGA). In some embodiments, crystalline forms are characterized by an X-ray powder diffractogram having signals at one or more specified two-theta values (° 2θ). On the other hand, an amorphous form is a solid material having no long range order in the position of its molecules. Amorphous solids are generally supercooled liquids in which the molecules are arranged in a random manner so that there is no well-defined arrangement, e.g., molecular packing, and no long range order. For example, an amorphous material is a solid material having no sharp characteristic signal(s) in its X-ray power diffractogram (i.e., is not crystalline as determined by XRPD).

"Compound 1," as used throughout this disclosure, refers to 4-(5-(4-fluorophenyl)-6-(tetrahydro-2H-pyran-4-yl)-1,5-dihydropyrrolo[2,3-f]indazol-7-yl)benzoic acid, which can be depicted as having the following structure:

(Compound 1)

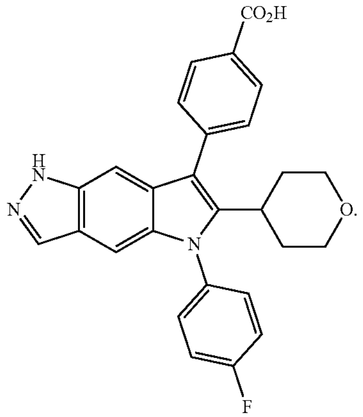

Compound 1 may be in the form of an isomeric mixture or enantioenriched (e.g., >90% ee, >95% ee, >98% ee) isomers. Compound 1 may be in the form of a pharmaceutically acceptable salt.

"Compound 2," as used throughout this disclosure, refers to 3-(5-(4-fluorophenyl)-6-isopropyl-1,5-dihydropyrrolo[2,3-f]indazol-7-yl)propanoic acid, which can be depicted as having the following structure:

(Compound 2)

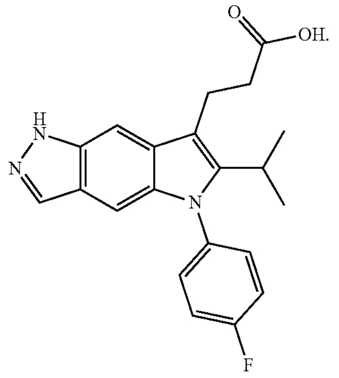

Compound 2 may be in the form of an isomeric mixture or enantioenriched (e.g., >90% ee, >95% ee, >98% ee) isomers. Compound 2 may be in the form of a pharmaceutically acceptable salt.

A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences,* 1977, 66, 1-19.

Acids commonly employed to form pharmaceutically acceptable salts include inorganic acids such as hydrogen bisulfide, hydrochloric acid, hydrobromic acid, hydroiodic acid, sulfuric acid, and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, and acetic acid, as well as related inorganic and organic acids. Such pharmaceutically acceptable salts include, but are not limited to, sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate, and other salts. In some embodiments, pharmaceutically acceptable acid addition salts include those formed with mineral acids, such as, e.g., hydrochloric acid and hydrobromic acid, and those formed with organic acids, such as, e.g., maleic acid.

Pharmaceutically acceptable salts derived from appropriate bases include, but are not limited to, alkali metal, alkaline earth metal, ammonium, and $N^+(C_{1-4}\ alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions, such as, e.g., halide, hydroxide, carboxylate, sulfate, phosphate, nitrate, lower alkyl sulfonate, and aryl sulfonate. Other suitable, non-limiting examples of pharmaceutically acceptable salts include besylate and glucosamine salts.

Examples of suitable solvents that may be used in this disclosure include, but not limited to, water, methanol (MeOH), ethanol (EtOH), 1-propanol, 2-propanol, dichloromethane (DCM) or "methylene chloride" ($CH_2Cl_2$), dimethylacetamide (DMAc), toluene, xylene, methyl cyclohexane, acetonitrile (MeCN; ACN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, trifluoromethylbenzene, cyclopentyl methyl ether (CPME), propan-2-one/cyclopentane mixture, ethyl acetate/ethanol mixture, N-methyl pyrrolidone (NMP) piperidine, N-formylpiperidine, 2,2,6,6-tetramethylpiperidine, pyridine, etc. Suitable solvents for specific reaction steps in the processes provided herein are described in greater detail in the non-limiting exemplary embodiments and appended examples.

Examples of suitable bases that may be used in this disclosure include, but not limited to, 1,8-diazabicyclo [5.4.0]undec-7-ene (DBU), potassium tert-butoxide (KOtBu), sodium tert-butoxide (NaOtBu), sodium tert-amylate (NaOt-Am), sodium carbonate ($Na_2CO_3$), potassium carbonate ($K_2CO_3$), cesium carbonate ($Cs_2CO_3$), N-methylmorpholine (NMM), triethylamine ($Et_3N$; TEA), diisopropyl-ethyl amine (i-$Pr_2$EtN; DIPEA), pyridine, potassium hydroxide (KOH), sodium hydroxide (NaOH), lithium hydroxide (LiOH), and sodium methoxide (NaOMe; $NaOCH_3$). Suitable bases for specific reaction steps in the processes provided herein are described in greater detail in the non-limiting exemplary embodiments and appended examples.

As used herein, the term "palladium-phosphine complex-based catalyst" refers to a catalyst with one or more palladium ions being coordinated by multiple phosphine ($PR^A_3$) ligands, where $R^A$ is hydrogen, an organic aliphatic group, or an aryl group. The positive charge of the palladium-phosphine complexes is typically neutralized by pairing the complexes with anions, such as, e.g., chloride, fluoride, etc. Non-limiting examples of palladium-phosphine complex-based catalysts include 2-dicyclohexylphosphino-2',4',6'-triisopropylbiphenyl palladium or XPhos Pd (G1-G4), 2-di-tert-butylphosphino-2',4',6'-triisopropylbiphenyl palladium or tBuXPhos Pd (G1-G4), dicyclohexyl(2',4',6'-triisopropyl-3,6-dimethoxy-[1,1'-biphenyl]-2-yl)phosphine or BrettPhos Pd (G1-G4), 2-(di-tert-butylphosphino)-2',4',6'-triisopropyl-3,6-dimethoxy-1,1'-biphenyl, tBuBrettPhos Pd (G1-G4), bis (tri-t-butylphosphine) Pd, bis(triphenylphosphine)Pd dichloride or $Pd(PPh_3)_2Cl_2$, and 1,1'-bis(diphenylphosphino)ferrocene]dichloropalladium(II) that is optionally complexed with dichloromethane or $Pd(dppf)Cl_2$ or $Pd(dppf)Cl_2{\cdot}CH_2Cl_2$. Suitable catalysts from the list above for specific reaction steps in the processes provided herein are described in greater detail in the non-limiting exemplary embodiments and appended examples.

As used herein, the term "silicon-based reducing agent" refers to a substance that contains at least one Si—X group (e.g., X=Cl or $OR^B$, $R^B$ being an organic aliphatic or aryl group) bond that can be reduced to Si—H, and is in turn capable of donating an electron to an electron recipient (oxidizing agent) in a redox chemical reaction, such as, e.g., silanes (where the central silicon bonded to four atoms (not all four are hydrogen) or functional groups) or siloxanes (which are characterized by the —Si—O—Si— linkage). Non-limiting examples of silicon-based reducing agents or silane reducing agents include triethylsilane, trichlorosilane, methyldichlorosilane, dimethylchlorosilane, triphenylsilane, tris(trimethylsilyl)silane, and dimethylsilyloxy(dimethyl)silane. Suitable silicon-based reducing agents for specific reaction steps in the processes provided herein are described in greater detail in the non-limiting exemplary embodiments and appended examples.

As used herein, the term "phosphetane oxide catalyst" refers to a catalyst having a general formula of

where each open valence of the carbon atom or phosphorus atom on the four-membered ring may be substituted, for example, with an organic aliphatic or aryl group, or a halogen atom.

The terms "about" and "approximately," when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. Typically, the term "about" refers to a variation of up to 10%, up to 5%, or up to 2% of a stated value.

Previously Disclosed Synthesis Processes of Compound 1

As mentioned above, synthesis processes of Compound 1 and pharmaceutically acceptable salts thereof are provided in International Patent Application No. PCT/US2020/032832, published as International Patent Application Publication No. WO 2020/247160. These processes as described in WO 2020/247160 are depicted in Schemes 1A-1C below. Alternative reaction steps are indicated with dashed arrows.

Scheme 1A - Part A: Synthesis of Intermediate C13

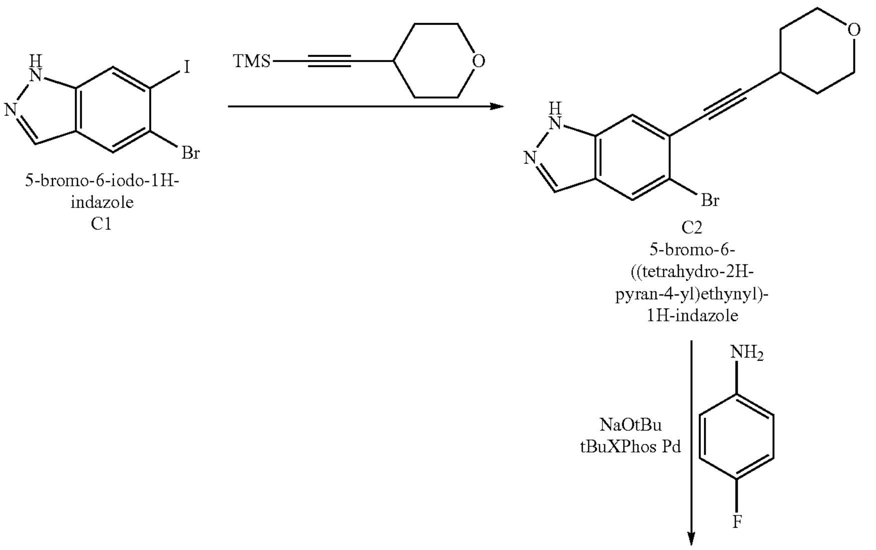

5-bromo-6-iodo-1H-indazole
C1

C2
5-bromo-6-((tetrahydro-2H-pyran-4-yl)ethynyl)-1H-indazole

-continued
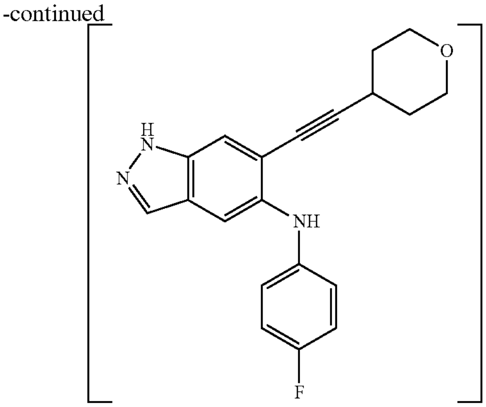
N-(4-fluorophenyl)-6-((tetrahydro-2H-pyran-4-yl)ethynyl)-1H-indazol-5-amine
C12
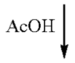
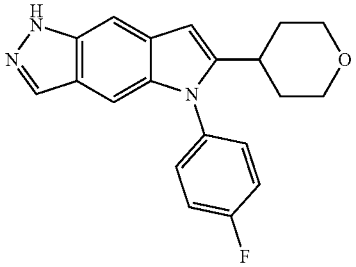
C13
5-(4-fluorophenyl)-6-(tetrahydro-2H-pyran-4-yl)-1,5-dihydropyrrolo[2,3-f]indazole
Scheme 1B - Part B: Synthesis of Intermediate S6 or S4
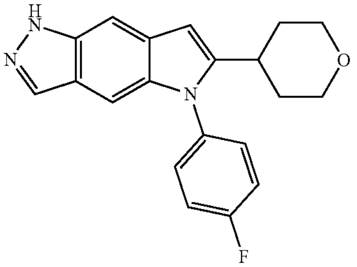
C13
5-(4-fluorophenyl)-6-(tetrahydro-2H-pyran-4-yl)-1,5-dihydropyrrolo[2,3-f]indazole
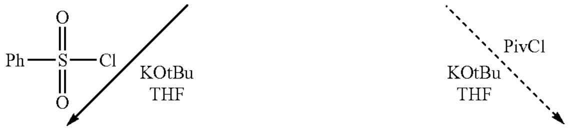

-continued
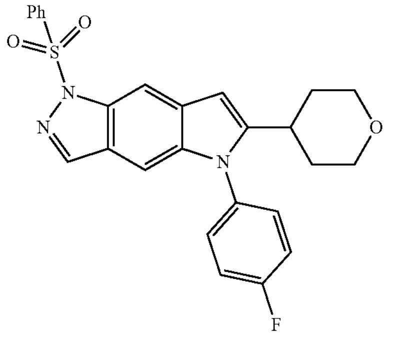
C15
5-(4-fluorophenyl)-1-(phenylsulfonyl)-6-(tetrahydro-2H-pyran-4-yl)-1,5-dihydropyrrolo[2,3-f]indazole
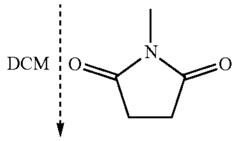
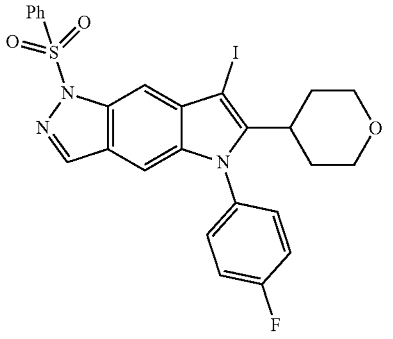
S6
5-(4-fluorophenyl)-7-iodo-1-(phenylsulfonyl)-6-(tetrahydro-2H-pyran-4-yl)-1,5-dihydropyrrolo[2,3-f]indazole
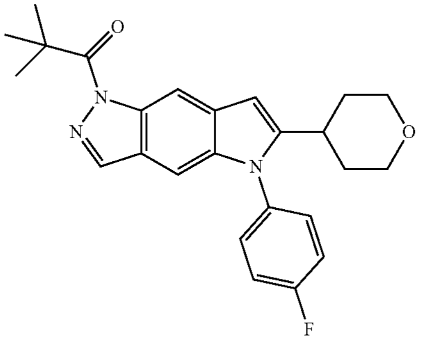
C14
1-(5-(4-fluorophenyl)-6-(tetrahydro-2H-pyran-4-yl)pyrrolo[2,3-f]indazol-1(5H)-yl)-2,2-dimethylpropan-1-one
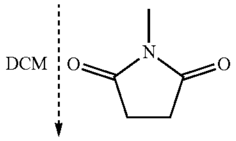
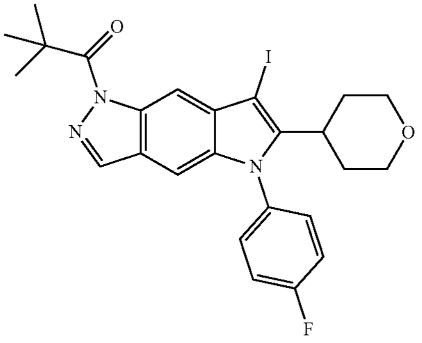
S4
1-(5-(4-fluorophenyl)-7-iodo-6-(tetrahydro-2H-pyran-4-yl)pyrrolo[2,3-f]indazole-1(5H)-yl)-2,2-dimethylpropan-1-one Scheme 1C - Part C: Synthesis of Compound 1

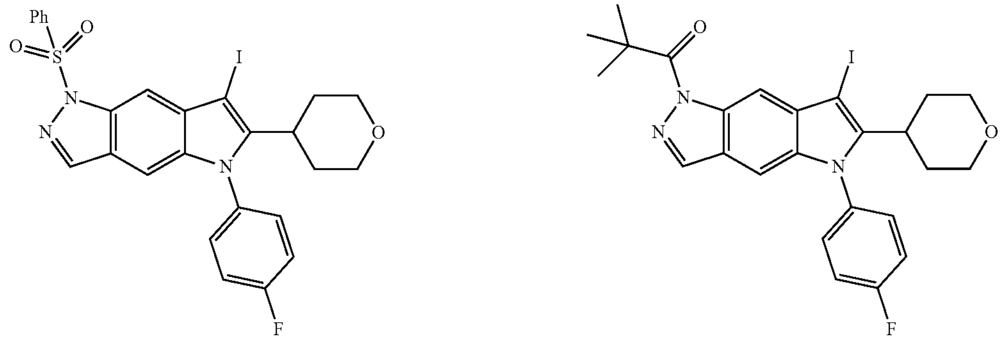

S6
5-(4-fluorophenyl)-7-iodo-1-(phenylsulfonyl)-6-(tetrahydro-2H-pyran-4-yl)-1,5-dihydropyrrolo[2,3-f]indazole S4
1-(5-(4-fluorophenyl)-7-iodo-6-(tetrahydro-2H-pyran-4-yl)pyrrolo[2,3-f]indazol-1(5H)-yl)-2,2-dimethylpropan-1-one

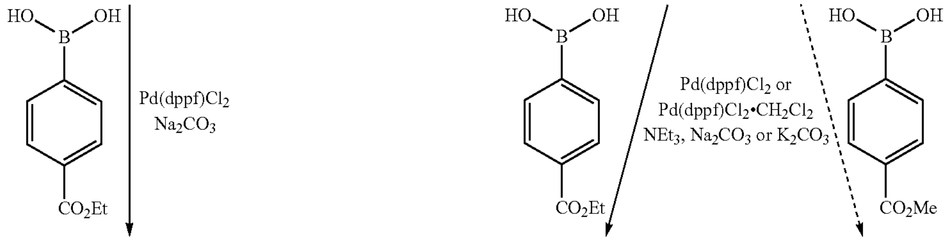

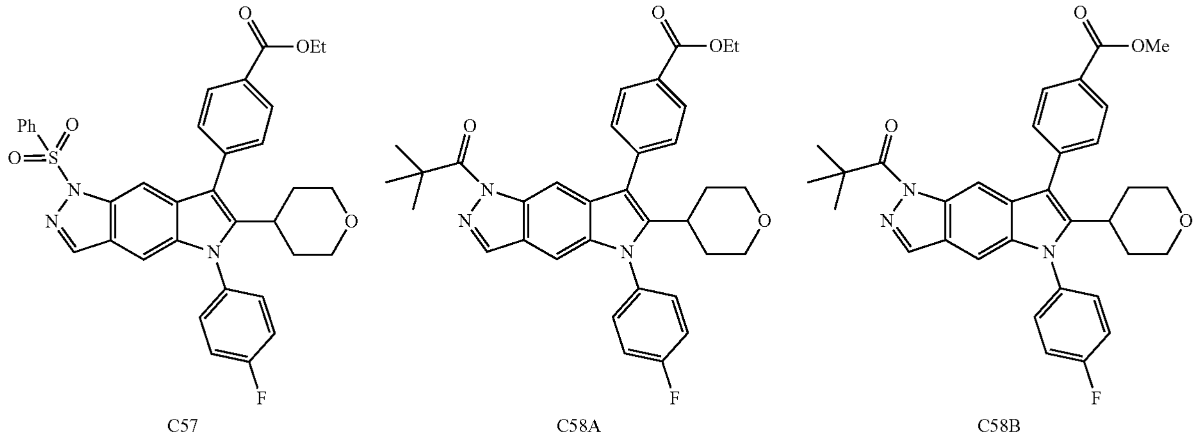

C57
ethyl 4-(5-(4-fluorophenyl)-1-(phenylsulfonyl)-6-tetrahydro-2H-pyran-4-yl)-1,5-dihydropyrrolo[2,3-f]indazole-7-yl)benzoate C58A
ethyl 4-(5-(4-fluorophenyl)-1-pivaloyl-6-(tetrahydro-2H-pyran-4-yl)-1,5-dihydropyrrolo [2,3-f]indazole-7-yl)benzoate C58B
methyl 4-(5-(4-fluorophenyl)-1-pivaloyl-6-(tetrahydro-2H-pyran-4-yl)-1,5-dihydropyrrolo [2,3-f]indazole-7-yl)benzoate

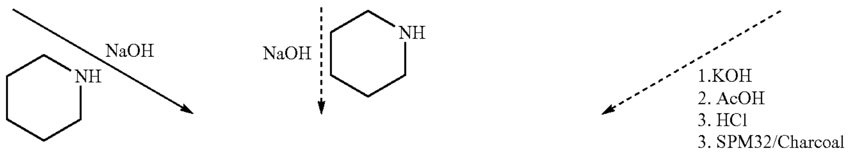

-continued

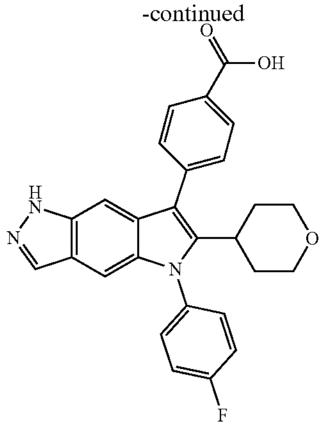

Compound 1

Referring to Schemes 1A-1C above, the synthesis processes as described in WO 2020/247160 can be divided into three parts: Part A that begins with the starting material C1 (5-bromo-6-iodo-1H-indazole) and culminates in the formation of the intermediate C13 5-(4-fluorophenyl)-6-(tetrahydro-2H-pyran-4-yl)-1,5-dihydropyrrolo[2,3-f]indazole; Part B that culminates in the formation of the key intermediate with a protecting group that prevents the nitrogen atom at position 1 of the tri-cyclic 1,5-dihydropyrrolo[2,3-f]indazole core from being reacted upon: S6 (5-(4-fluorophenyl)-7-iodo-1-(phenylsulfonyl)-6-(tetrahydro-2H-pyran-4-yl)-1,5-dihydropyrrolo[2,3-f]indazole) with a phenylsulfonyl protecting group or S4 (1-(5-(4-fluorophenyl)-7-iodo-6-(tetrahydro-2H-pyran-4-yl)pyrrolo[2,3-f]indazol-1(5H)-yl)-2,2-dimethylpropan-1-one) with a pivaloyl protecting group; and Part C that culminates in the synthesis of Compound 1 from the intermediate S6 or S4 derived from Part B via the formation any one of the esters C57 (ethyl 4-(5-(4-fluorophenyl)-1-(phenylsulfonyl)-6-(tetrahydro-2H-pyran-4-yl)-1,5-dihydropyrrolo[2,3-f]indazol-7-yl)benzoate), C58A (ethyl 4-(5-(4-fluorophenyl)-1-pivaloyl-6-(tetrahydro-2H-pyran-4-yl)-1,5-dihydropyrrolo[2,3-f]indazol-7-yl)benzoate), or C58B (methyl 4-(5-(4-fluorophenyl)-1-pivaloyl-6-(tetrahydro-2H-pyran-4-yl)-1,5-dihydropyrrolo[2,3-f]indazol-7-yl)benzoate).

Non-Limiting Differences Between and Advantages of New Processes of Preparing Compound 1

The present disclosure provides alternative processes for preparing a solid form of Compound 1 or a pharmaceutically acceptable salt thereof that can be distinguished from previously disclosed processes in several aspects. For instance, S6 or S4, which are each a 5-(4-fluorophenyl)-6-(tetrahydro-2H-pyran-4-yl)-1,5-dihydropyrrolo[2,3-f]indazole having the phenylsulfonyl or pivaloyl protecting group, is a key intermediate that is common to all previously disclosed processes. In contrast, the process provided herein does not produce this class of intermediates having a tri-cyclic fused ring system that is linked to a tetrahydro-2H-pyranyl ring and a phenyl ring. Instead, a new intermediate, such as B1 as depicted in Scheme 3 and described in the appended Example 1, is formed. B1 is a phenyl-indazolamine that differs from S6 and S4 not only in that it possesses a two-ring indazole ring core, but also in that the fluorophenyl ring is not directly linked to this indazole core but is instead linked via an amino group. Furthermore, B1 lacks the tetrahydro-2H-pyranyl ring linked to the indazole core.

Furthermore, the processes provided herein incorporate starting materials, reagents, and catalysts that are different from those utilized in the previously disclosed processes. For instance, Example 1 below utilizes a starting material having a pivaloyl (Piv) protecting group and having a nitro group and a halogen as substituents (e.g., A1). This contrasts with the starting material in the previously disclosed processes, which possesses halogen groups as substituents (i.e., C1). Furthermore, the starting material in Example 1 below is reacted with a phenylboronic acid in the presence of a siloxane (i.e., with a —Si—O—Si— linkage) and a phosphetane oxide catalyst (see Step 1 of Scheme 3B), neither of which are utilized in the previously disclosed processes, to form B1. B1 then proceeds to react with methyl 4-(2-oxo-2-(tetrahydro-2H-pyran-4-yl)ethyl)benzoate or D1, another new class of reagent, to form C58B.

Importantly, the processes provided herein enable Compound 1 to be synthesized using a reduced number of steps. Specifically, while the previously described processes contain as many as 7 reaction steps (as shown in Schemes 1A-1C), the processes of this disclosure, such as Example 1, contains at most contain 4 reaction steps. Moreover, the processes of this disclosure are capable of producing amounts of a solid form of Compound 1 or a pharmaceutically acceptable salt thereof of about 100 kg and above.

The key advantages of bypassing one or more reaction steps are that such a process, especially when preparing a compound on a large scale, would be significantly more efficient in terms of cost, time, and energy use. As discussed above, Compound 1 is being studied for medical uses. As Compound 1 moves to higher phase clinical studies with larger subject populations and when the drug is approved and becomes accessible to the public, the advantages of a cost-, time-, and energy-efficient Compound 1 synthesis process would be even more clearly manifested.

The alternative processes for preparing a solid form of Compound 1 or a pharmaceutically acceptable salt thereof are described in greater detail in the following non-limiting exemplary embodiments and also in the appended Example 1.

Non-Limiting Exemplary Embodiments (Compound 1 Processes)

1. A process for preparing a solid form of Compound 1

(Compound 1)

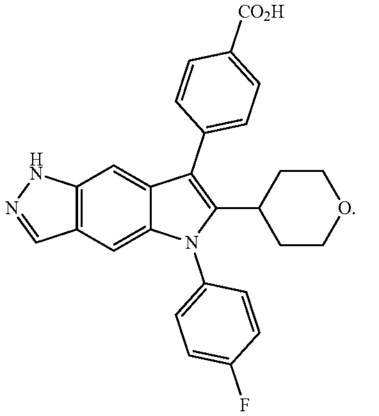

or a pharmaceutically acceptable salt thereof, comprising:

(a) reacting

B1

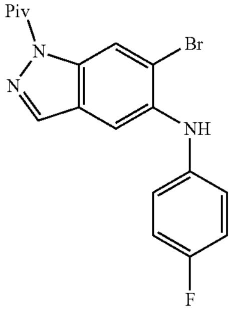

or a pharmaceutically acceptable salt thereof with

D1

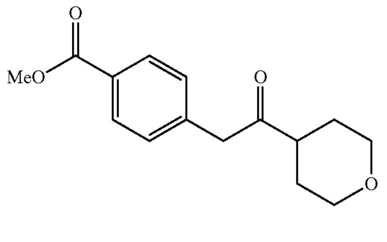

to form

C58B

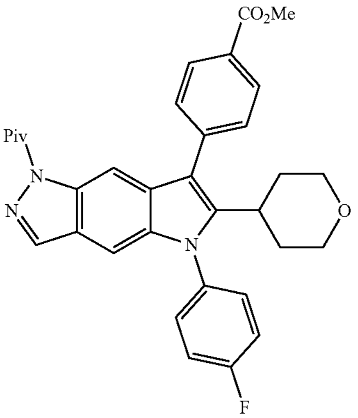

or a pharmaceutically acceptable salt thereof, and (b) de-esterifying C58B or a pharmaceutically acceptable salt thereof to yield the solid form of Compound 1 or a pharmaceutically acceptable salt thereof.

2. The process according to embodiment 1, wherein step (a) comprises reacting B1 or a pharmaceutically acceptable salt thereof with D1 in the presence of a palladium-phosphine complex-based catalyst, a base, and a solvent selected from tetrahydrofuran, 2-methyltetrahydrofuran, cyclopentyl methyl ether, toluene, dimethylformamide, acetonitrile, propionitrile, and a combination thereof.

3. The process according to embodiment 1 or embodiment 2, wherein the solvent is selected from selected from tetrahydrofuran, 2-methyltetrahydrofuran, cyclopentyl methyl ether, acetonitrile, and a combination thereof (e.g., selected from tetrahydrofuran, 2-methyltetrahydrofuran, cyclopentyl methyl ether, and a combination thereof).

4. The process according to embodiment 2 or embodiment 3, wherein the palladium-phosphine complex-based catalyst is selected from XPhos Pd, tBuXPhos Pd, BrettPhos Pd, tBuBrettPhos Pd, bis(tri-t-butylphosphine) Pd, di-adamantylalkylphosphine Pd, 2-(di-tert-butylphosphino)-1-(2-methoxyphenyl)-1H-pyrrole Pd, and bis(triphenylphosphine)Pd dichloride.

5. The process according to any one of embodiments 2 to 4, wherein the palladium-phosphine complex-based catalyst is selected from XPhos Pd, tBuXPhos Pd, BrettPhos Pd, tBuBrettPhos Pd, bis(tri-t-butylphosphine) Pd, and bis(triphenylphosphine)Pd dichloride.

6. The process according to any one of embodiments 2 to 4, wherein the palladium-phosphine complex-based catalyst is selected from XPhos Pd, BrettPhos Pd, di-adamantylalkylphosphine Pd, and 2-(di-tert-butylphosphino)-1-(2-methoxyphenyl)-1H-pyrrole Pd.

7. The process according to any one of embodiments 2 to 5, wherein the palladium-phosphine complex-based catalyst is bis(tri-t-butylphosphine) Pd.

8. The process according to any one of embodiments 2 to 7, wherein the base is selected from potassium dihydrogen phosphate, potassium phosphate tribasic (e.g., anhydrous potassium phosphate tribasic and potassium phosphate monohydrate), dipotassium hydrogen phosphate, cesium carbonate, sodium carbonate, potassium carbonate, and a combination thereof.

9. The process according to any one of embodiments 2 to 8, wherein the base is selected from potassium dihydrogen phosphate, dipotassium hydrogen phosphate, cesium carbonate, potassium carbonate, and a combination thereof.

10. The process according to any one of embodiments 2 to 8, wherein the base is selected from sodium carbonate, potassium carbonate, and a combination thereof.

11. The process according to any one of embodiments 2 to 10, wherein the base is potassium carbonate.

12. The process according to any one of embodiments 2 to 11, wherein the solvent is 2-methyltetrahydrofuran.

13. The process according to any one of embodiments 2 to 11, wherein the solvent is tetrahydrofuran.

14. The process according to any one of embodiments 1 to 13, wherein step (a) comprises reacting B1 or a pharmaceutically acceptable salt thereof with D1 at about 35-100° C. (e.g., about 50-80° C.).

15. The process according to any one of embodiments 1 to 14, wherein step (a) comprises reacting B1 or a pharmaceutically acceptable salt thereof with D1 at about 70-80° C. (e.g., 75° C.).

16. The process according to any one of embodiments 1 to 14, wherein step (a) comprises reacting B1 or a pharmaceutically acceptable salt thereof with D1 at about 50-55° C.

17. The process according to any one of embodiments 1 to 16, wherein step (b) comprises de-esterifying C58B or a pharmaceutically acceptable salt thereof with a base selected from lithium hydroxide, potassium hydroxide, sodium hydroxide, and a combination thereof.

18. The process according to embodiment 17, wherein the base is sodium hydroxide.

19. The process according to any one embodiments 1 to 18, wherein step (b) comprises de-esterifying C58B or a pharmaceutically acceptable salt thereof in the presence of a solvent selected from 2-methyltetrahydrofuran, tetrahydrofuran, methanol, ethanol, isopropyl alcohol, and a combination thereof.

20. The process according to embodiment 19, wherein the solvent is tetrahydrofuran.

21. The process according to embodiment 19 or embodiment 20, wherein step (b) comprises de-esterifying C58B or a pharmaceutically acceptable salt thereof at about 55-65° C.

22. The process according to any one of embodiments 1 to 21, wherein the process further comprises at least one additional step selected from:

(a1) reacting

A0

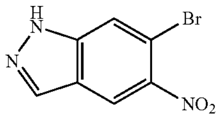

or a pharmaceutically acceptable salt thereof with pivaloyl chloride to form

A1

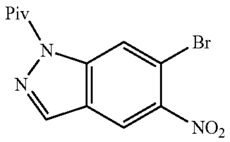

or a pharmaceutically acceptable salt thereof; and (a2) reacting A1 or a pharmaceutically acceptable salt thereof with 4-fluorophenylboronic acid to form B1 or a pharmaceutically acceptable salt thereof.

23. The process according to embodiment 22, wherein step (a1) comprises reacting A0 or a pharmaceutically acceptable salt thereof with pivaloyl chloride in the presence of a base and a solvent selected from tetrahydrofuran, 2-methyltetrahydrofuran, cyclopentyl methyl ether, and a combination thereof.

24. The process according to embodiment 23, wherein the solvent is tetrahydrofuran.

25. The process according to embodiment 23 or embodiment 24, wherein the base is selected from sodium tert-butoxide, potassium tert-butoxide, sodium tert-amylate, and a combination thereof (e.g., sodium tert-amylate).

26. The process according to embodiment 25, wherein the base is potassium tert-butoxide.

27. The process according to any one of embodiments 22 to 26, wherein step (a1) comprises reacting A0 or a pharmaceutically acceptable salt thereof with pivaloyl chloride at about −10° C. to 20° C. (e.g., about 10-20° C.).

28. The process according to any one of embodiments 22 to 27, wherein step (a2) comprises reacting A1 or a pharmaceutically acceptable salt thereof with 4-fluorophenylboronic acid in the presence of a catalyst, a reducing agent, and a solvent selected from toluene, isopropanol, xylene, methyl cyclohexane, cyclopentyl methyl ether, methyl tert-butyl ether, isopropyl acetate, tetrahydrofuran, an aqueous solution comprising sodium carbonate and/or potassium carbonate (e.g., a sodium chloride aqueous solution comprising sodium carbonate and/or potassium carbonate), and a combination thereof (e.g., an isopropanol/toluene mixture).

29. The process according to embodiment 28, wherein the catalyst is selected from hexamethyloxophosphetane, $(MoO_2Cl_2)DMF_2$ with $PPh_3$ or a silane, 4-methyl-1-phenyl-2,3-dihydrophosphole 1-oxide 4, (2R,5R)-1-{2-[(2R,5R)-2,5-diethylphospholan-1-yl]phenyl}-2,5-diethyl-1-phospholan-1-one, and 1-(adamantan-1-ylphosphoroso)adamantane.

30. The process according to embodiment 28 or 29, wherein the catalyst is a phosphetane oxide catalyst.

31. The process according to any one of embodiments 28 to 30, wherein the solvent is selected from toluene, cyclopentyl methyl ether, isopropyl acetate, tetrahydrofuran, and a combination thereof.

32. The process according to any one of embodiments 22 to 27, wherein step (a2) comprises reacting A1 or a pharmaceutically acceptable salt thereof with 4-fluorophenylboronic acid in the presence of a phosphetane oxide catalyst, a reducing agent, and a solvent selected from toluene, xylene, methyl cyclohexane, and a combination thereof.

33. The process according to embodiment 30 or embodiment 32, wherein the phosphetane oxide catalyst is hexamethyloxophosphetane.
34. The process according to embodiment 32 or embodiment 33, wherein the reducing agent is selected from triethylsilane, trichlorosilane, polymethylsilane, methyldichlorosilane, dimethylchlorosilane, phenylsilane, triphenylsilane, triphenylphosphine, triphenylphosphine oxide, tris(trimethylsilyl)silane, dimethylsilyloxy(dimethyl)silane, and a combination thereof.
35. The process according to any one of embodiments 32 to 34, wherein the reducing agent is selected from polymethylsilane, phenylsilane, triphenylphosphine, triphenylphosphine oxide, dimethylsilyloxy(dimethyl)silane, and a combination thereof.
36. The process according to embodiment 32 or embodiment 33, wherein the reducing agent is a silicon-based reducing agent selected from triethylsilane, trichlorosilane, methyldichlorosilane, dimethylchlorosilane, triphenylsilane, tris(trimethylsilyl)silane, dimethylsilyloxy(dimethyl)silane, and a combination thereof.
37. The process according to embodiment 36, wherein the reducing agent is dimethylsilyloxy(dimethyl)silane.
38. The process according to any one of embodiments 32 to 37, wherein the solvent is toluene.
39. The process according to any one of embodiments 32 to 38, wherein step (a2) comprises reacting A1 or a pharmaceutically acceptable salt thereof with 4-fluorophenylboronic acid at about 85-105° C. (e.g., about 90° C., about 100° C.).
40. The process according to any one of embodiments 32 to 39, wherein step (a2) comprises reacting A1 or a pharmaceutically acceptable salt thereof with 4-fluorophenylboronic acid at about 85-95° C. (e.g., about 90° C.).
41. The process according to any one of embodiments 1 to 40, further comprising:
    (c) converting the solid form of Compound 1 or a pharmaceutically acceptable salt thereof to Compound 1 Form A.
42. The process according to embodiment 41, wherein step (c) comprises aging a slurry comprising the solid form of Compound 1 or a pharmaceutically acceptable salt thereof at about 20-25° C.
43. The process according to embodiment 41 or 42, wherein the solid form of Compound 1 or a pharmaceutically acceptable salt thereof is Compound 1 THF solvate.
44. The process according to any one of embodiments 1 to 43, wherein the process further comprises at least one additional step selected from:
    (b1) reacting

F1

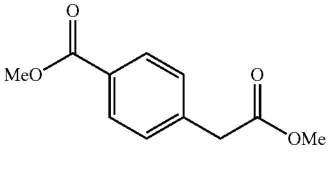

with oxane-4-carbonyl chloride to form

E1

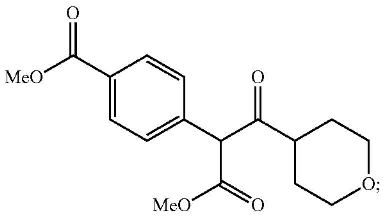

(b2) reacting E1 with an aqueous solution to form D1.
45. The process according to embodiment 44, wherein the aqueous solution comprises chloride (e.g., sodium chloride, lithium chloride).
46. The process according to embodiment 44 or embodiment 45, wherein the aqueous solution is a sodium chloride aqueous solution.
47. The process according to any one of embodiments 44 to 46, wherein step (b2) comprises reacting E1 with the aqueous solution at about 100-200° C. (e.g., about 200° C.).
48. The process according to embodiment 46 or embodiment 47, wherein step (b2) comprises reacting E1 with the sodium chloride aqueous solution at about 120-180° C. (e.g., about 150° C.).
49. The process according to any one of embodiment 44 to 47, wherein step (b2) comprises reacting E1 with an aqueous solution (e.g., water) in the presence of tetrahydrofuran.
50. The process according to any one of embodiments 44 to 49, wherein step (b2) comprises reacting E1 with a chloride containing aqueous solution (e.g., a sodium chloride aqueous solution, a lithium chloride aqueous solution) in the presence of a solvent selected from dimethyl sulfoxide, ethyl acetate/ethanol mixture, 2-methyltetrahydrofuran, tetrahydrofuran, dimethylacetamide, and a combination thereof.
51. The process according to embodiment 50, wherein step (b2) comprises reacting E1 with a sodium chloride aqueous solution in the presence of a solvent selected from dimethyl sulfoxide, ethyl acetate/ethanol mixture, 2-methyltetrahydrofuran, and a combination thereof.
52. The process according to embodiment 50 or embodiment 51, wherein the solvent is dimethyl sulfoxide.
53. The process according to any one of embodiments 44 to 52, wherein step (b1) comprises reacting F1 with oxane-4-carbonyl chloride in the presence of a base and a solvent selected from tetrahydrofuran, 2-methyltetrahydrofuran, cyclopentyl methyl ether, and a combination thereof.
54. The process according to embodiment 53, wherein the solvent is tetrahydrofuran.
55. The process according to embodiment 53 or embodiment 54, wherein the base is selected from sodium tert-butoxide, potassium tert-butoxide, lithium tert-butoxide, sodium tert-amylate, sodium bis(trimethylsilyl)amide, potassium bis(trimethylsilyl)amide, lithium bis(trimethylsilyl)amide, and a combination thereof.
56. The process according to any one of embodiments 53 to 55, wherein the base is selected from sodium tert-butoxide, potassium tert-butoxide, sodium tert-amylate, and a combination thereof.

57. The process according to any one of embodiments 53 to 56, wherein the base is potassium tert-butoxide.

58. The process according to any one of embodiments 53 to 55, wherein the base is lithium bis(trimethylsilyl) amide.

59. The process according to any one of embodiments 44 to 58, wherein step (b1) comprises reacting F1 with oxane-4-carbonyl chloride at about −40° C. to 15° C. (e.g., about 0° C.).

60. The process according to any one of embodiments 44 to 59, wherein step (b1) comprises reacting F1 with oxane-4-carbonyl chloride at about −40° C. to 0° C.

61. A process for preparing a solid form of Compound 1

(Compound 1)

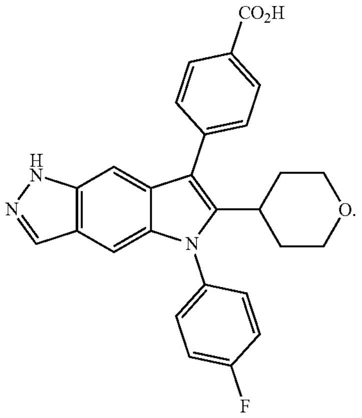

or a pharmaceutically acceptable salt thereof, comprising:

(a1) reacting

A0

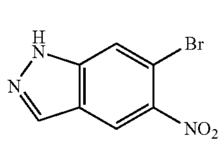

or a pharmaceutically acceptable salt thereof with pivaloyl chloride to form

A1

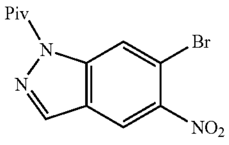

or a pharmaceutically acceptable salt thereof;

(a2) reacting A1 or a pharmaceutically acceptable salt thereof with 4-fluorophenylboronic acid to form

B1

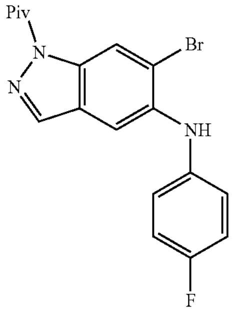

or a pharmaceutically acceptable salt thereof;

(a) reacting B1 or a pharmaceutically acceptable salt thereof with

D1

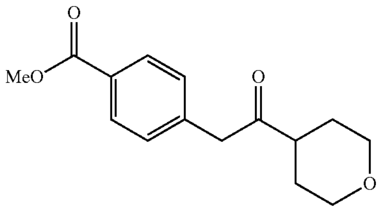

to form

C58B

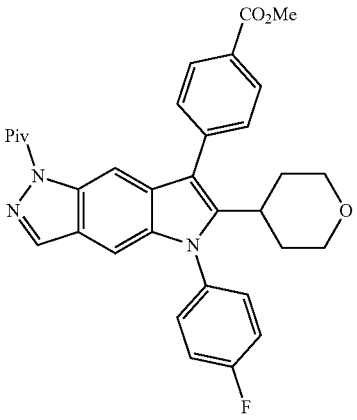

or a pharmaceutically acceptable salt thereof, and (b) de-esterifying C58B or a pharmaceutically acceptable salt thereof to yield the solid form of Compound 1 or a pharmaceutically acceptable salt thereof.

62. The process according to embodiment 61, wherein the process can be further defined with the additional reaction steps, the reagents and conditions recited in any one of embodiments 2 to 60.

63. The process according to embodiment 61 or embodiment 62, further comprising: (c) converting the solid form of Compound 1 or a pharmaceutically acceptable salt thereof to Compound 1 Form A.

64. The process according to embodiment 63, wherein step (c) comprises aging a slurry comprising the solid form of Compound 1 or a pharmaceutically acceptable salt thereof at about 20-25° C.

65. The process according to embodiment 63 or embodiment 64, wherein the solid form of Compound 1 or a pharmaceutically acceptable salt thereof is Compound 1 THF solvate.

66. A compound

A1

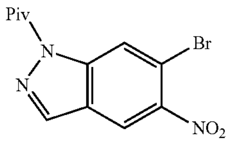

or a pharmaceutically acceptable salt thereof.

67. A compound

B1

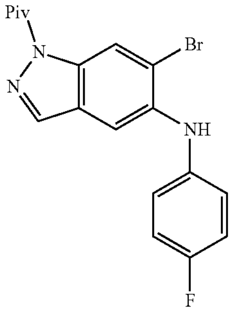

or a pharmaceutically acceptable salt thereof.

68. A compound

D1

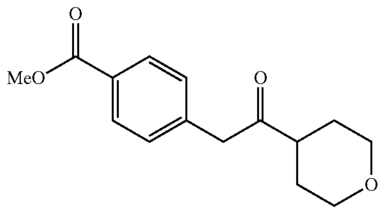

or a pharmaceutically acceptable salt thereof.

69. A compound

E1

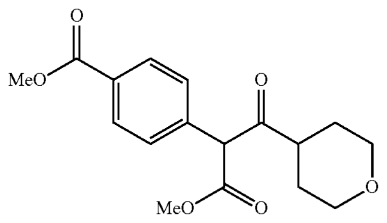

or a pharmaceutically acceptable salt thereof.

70. A process for preparing a solid form of Compound 1

(Compound 1)

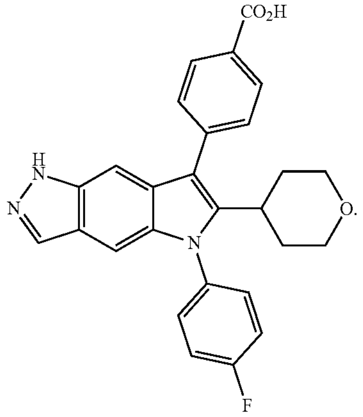

or a pharmaceutically acceptable salt thereof, comprising:

(i) reacting

B1

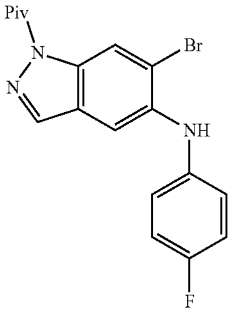

or a pharmaceutically acceptable salt thereof with trimethyl((tetrahydro-2H-pyran-4-yl)ethynyl)silane to form

C13

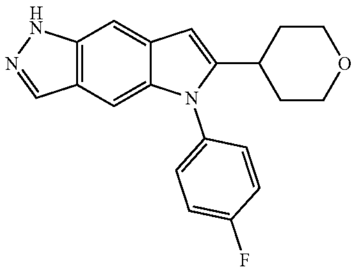

or a pharmaceutically acceptable salt thereof;

(ii) reacting C13 or a pharmaceutically acceptable salt thereof with benzenesulfonyl chloride to form

S6

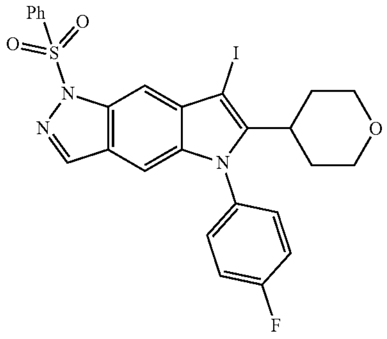

or a pharmaceutically acceptable salt thereof, (iii) halogenizing C15 or a pharmaceutically acceptable salt thereof to form

S6

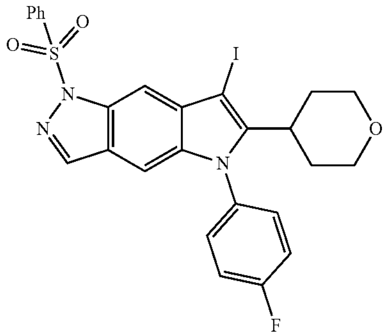

or a pharmaceutically acceptable salt thereof;

(iv) reacting S6 or a pharmaceutically acceptable salt thereof with (4-(ethoxycarbonyl)phenyl)boronic acid to form

C57

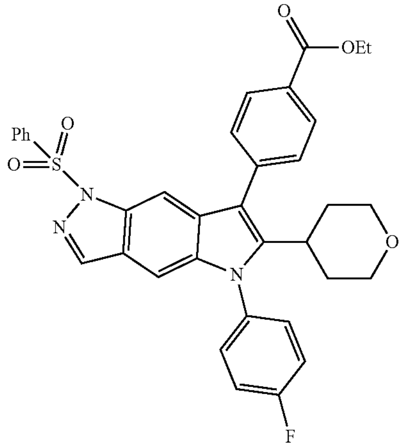

or a pharmaceutically acceptable salt thereof; and (v) de-esterifying C57 or a pharmaceutically acceptable salt thereof to yield the solid form of Compound 1 or a pharmaceutically acceptable salt thereof.

71. The process according to embodiment 70, further comprising:

(vi) converting the solid form of Compound 1 or a pharmaceutically acceptable salt thereof to Compound 1 Form A.

72. The process according to embodiment 71, wherein step (vi) comprises aging a slurry comprising the solid form of Compound 1 or a pharmaceutically acceptable salt thereof at about 20-25° C.

73. The process according to embodiment 71 or embodiment 72, wherein the solid form of Compound 1 or a pharmaceutically acceptable salt thereof is Compound 1 THF solvate.

74. A process for preparing a solid form of Compound 1

(Compound 1)

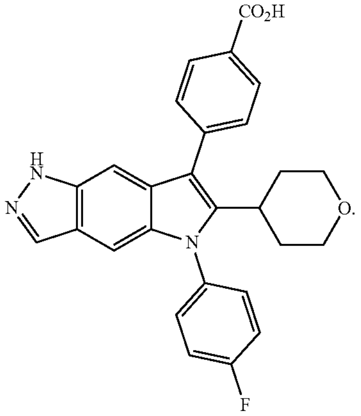

or a pharmaceutically acceptable salt thereof, comprising:

(i) reacting

B1

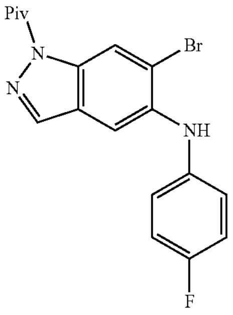

or a pharmaceutically acceptable salt thereof with trimethyl ((tetrahydro-2H-pyran-4-yl)ethynyl)silane to form

C13

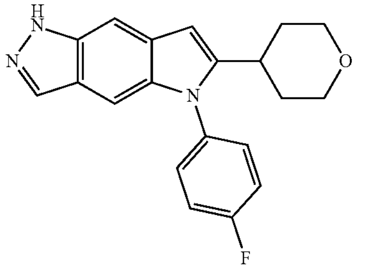

or a pharmaceutically acceptable salt thereof;

(ii) reacting C13 or a pharmaceutically acceptable salt thereof with pivaloyl chloride to form

C14

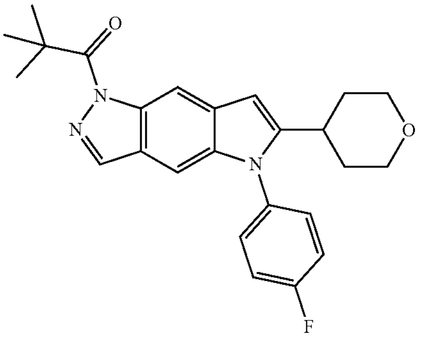

or a pharmaceutically acceptable salt thereof;

(iii) halogenizing C14 or a pharmaceutically acceptable salt thereof to form

S4

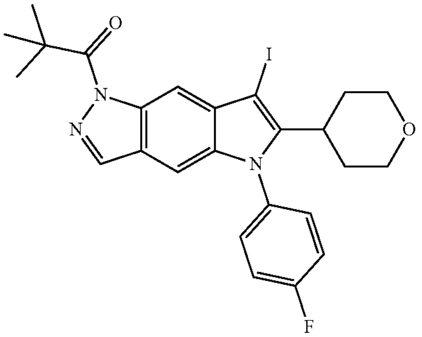

or a pharmaceutically acceptable salt thereof, (iv) reacting S4 or a pharmaceutically acceptable salt thereof with (4-(ethoxycarbonyl)phenyl)boronic acid to form

C58A

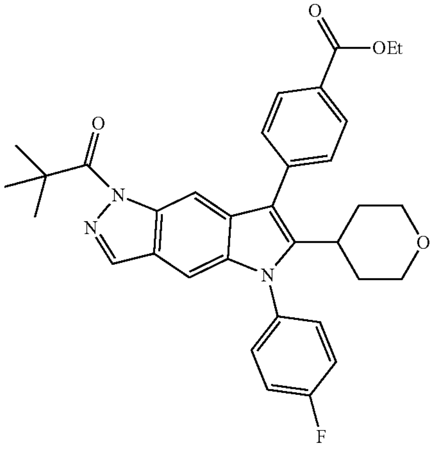

or a pharmaceutically acceptable salt thereof; or alternatively reacting S6 or a pharmaceutically acceptable salt thereof with (4-(methoxycarbonyl)phenyl)boronic acid to form

C58B

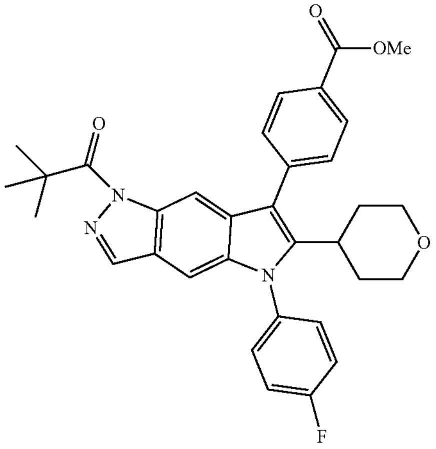

or a pharmaceutically acceptable salt thereof, and (v) de-esterifying C58A or a pharmaceutically acceptable salt thereof or C58B or a pharmaceutically acceptable salt thereof to yield the solid form of Compound 1 or a pharmaceutically acceptable salt thereof.

75. The process according to embodiment 74, further comprising:

(vi) converting the solid form of Compound 1 or a pharmaceutically acceptable salt thereof to Compound 1 Form A.

76. The process according to embodiment 75, wherein step (vi) comprises aging a slurry comprising the solid form of Compound 1 or a pharmaceutically acceptable salt thereof at about 20-25° C.

77. The process according to embodiment 75 or embodiment 76, wherein the solid form of Compound 1 or a pharmaceutically acceptable salt thereof is Compound 1 THF solvate.

78. A process for preparing C13:

C13

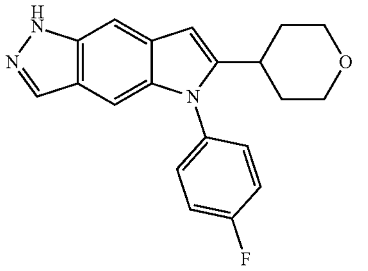

or a pharmaceutically acceptable salt thereof, comprising:

(i) reacting

B1

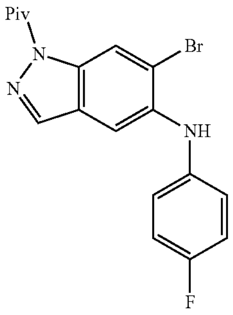

or a pharmaceutically acceptable salt thereof with trimethyl ((tetrahydro-2H-pyran-4-yl)ethynyl)silane to yield C13 or a pharmaceutically acceptable salt thereof.

79. The process according to any one of embodiments 70 to 78, wherein step (i) comprises reacting B1 or a pharmaceutically acceptable salt thereof with trimethyl ((tetrahydro-2H-pyran-4-yl)ethynyl)silane in the presence of a base selected from lithium hydroxide, potassium hydroxide, sodium hydroxide, and a combination thereof.

80. The process according to embodiment 79, wherein the base is potassium hydroxide.

81. The process according to any one of embodiments 70 to 80, wherein step (i) comprises reacting B1 or a pharmaceutically acceptable salt thereof with trimethyl ((tetrahydro-2H-pyran-4-yl)ethynyl)silane in the presence of copper iodide.

82. The process according to any one of embodiments 70 to 81, wherein step (i) comprises reacting B1 or a pharmaceutically acceptable salt thereof with trimethyl ((tetrahydro-2H-pyran-4-yl)ethynyl)silane in the presence of a palladium-phosphine complex-based catalyst.

83. The process according to embodiment 82, wherein the palladium-phosphine complex-based catalyst is selected from XPhos Pd, tBuXPhos Pd, BrettPhos Pd, tBuBrettPhos Pd, bis(tri-t-butylphosphine) Pd, and bis (triphenylphosphine)Pd dichloride.

84. The process according to embodiment 83, wherein the palladium-phosphine complex-based catalyst is bis(triphenylphosphine)Pd dichloride.

85. The process according to any one of embodiments 70 to 84, wherein step (i) comprises reacting B1 or a pharmaceutically acceptable salt thereof with trimethyl ((tetrahydro-2H-pyran-4-yl)ethynyl)silane in the presence of an alcohol selected from 2-propanol, 1-butanol, and ethanol.

86. The process according to embodiment 85, wherein the alcohol is 2-propanol.

87. The process according to any one of embodiments 70 to 86, wherein step (i) comprises reacting B1 or a pharmaceutically acceptable salt thereof with trimethyl ((tetrahydro-2H-pyran-4-yl)ethynyl)silane in the presence of acetic acid, acetic anhydride in combination with acetic acid or water, or potassium bisulfite (e.g., in the presence of acetic acid).

88. The process according to embodiment 87, wherein step (i) comprises reacting B1 or a pharmaceutically acceptable salt thereof with trimethyl((tetrahydro-2H-pyran-4-yl)ethynyl)silane in the presence of acetic acid.

89. The process according to any one of embodiments 70, 74, and 79 to 88, wherein step (ii) comprises reacting C13 or a pharmaceutically acceptable salt thereof with benzenesulfonyl chloride or pivaloyl chloride in the presence of a base selected from sodium tert-butoxide, potassium tert-butoxide, sodium tert-amylate, and a combination thereof.

90. The process according to embodiment 89, wherein the base is potassium tert-butoxide.

91. The process according to any one of embodiments 70, 74, and 79 to 90, wherein step (ii) comprises reacting C13 or a pharmaceutically acceptable salt thereof with benzenesulfonyl chloride or pivaloyl chloride in the presence of a solvent selected from tetrahydrofuran, 2-methyltetrahydrofuran, cyclopentyl methyl ether, and a combination thereof.

92. The process according to embodiment 91, wherein the solvent is tetrahydrofuran.

93. The process according to any one of embodiments 70, 74, and 79 to 92, wherein step (iii) comprises reacting C15 or a pharmaceutically acceptable salt thereof or C14 or a pharmaceutically acceptable salt thereof with 1-iodopyrrolidine-2,5-dione.

94. The process according to any one of embodiments 70, 74, and 79 to 93, wherein step (iii) comprises reacting C15 or a pharmaceutically acceptable salt thereof or C14 or a pharmaceutically acceptable salt thereof in the presence of a solvent selected from dichloromethane, propan-2-one/cyclopentane mixture, ethyl acetate/ethanol mixture, and a combination thereof (e.g., reacting C15 or a pharmaceutically acceptable salt thereof in the presence of a solvent selected from dichloromethane, propan-2-one/cyclopentane mixture, ethyl acetate/ethanol mixture, and a combination thereof; reacting C14 or a pharmaceutically acceptable salt thereof in the presence of dichloromethane).

95. The process according to embodiment 94, wherein the solvent is dichloromethane.

96. The process according to any one of embodiments 70, 74, and 79 to 95, wherein step (iv) comprises reacting S6 or a pharmaceutically acceptable salt thereof or S4 or a pharmaceutically acceptable salt thereof with (4-(ethoxycarbonyl)phenyl)boronic acid or (4-(methoxycarbonyl)phenyl)boronic acid in the presence of a palladium-phosphine complex based catalyst.

97. The process according to embodiment 96, wherein the palladium-phosphine complex-based catalyst is selected from XPhos Pd, tBuXPhos Pd, BrettPhos Pd, tBuBrettPhos Pd, bis(tri-t-butylphosphine) Pd, bis(triphenylphosphine)Pd dichloride, 1,1'-bis(diphenylphosphino)ferrocene]dichloropalladium(II), and 1,1'-bis(diphenylphosphino)ferrocene]dichloropalladium(II) complexed with dichloromethane.

98. The process according to embodiment 97, wherein the palladium-phosphine complex-based catalyst is 1,1'-bis (diphenylphosphino)ferrocene]dichloropalladium(II) or 1,1'-bis(diphenylphosphino)ferrocene]dichloropalladium(II) complexed with dichloromethane (i.e., 1,1'-bis(diphenylphosphino)ferrocene]dichloropalladium (II) that is optionally complexed with dichloromethane).

99. The process according to any one of embodiments 70, 74, and 79 to 98, wherein step (iv) comprises reacting S6 or a pharmaceutically acceptable salt thereof or S4 or a pharmaceutically acceptable salt thereof with (4-(ethoxycarbonyl)phenyl)boronic acid or (4-(methoxycarbonyl)phenyl)boronic acid in the presence of a base selected from triethylamine, sodium carbonate, potassium carbonate, and a combination thereof.

100. The process according to any one of embodiments 70, 74, and 79 to 99, wherein step (v) comprises reacting C58A or a pharmaceutically acceptable salt thereof or C58B or a pharmaceutically acceptable salt thereof with a base selected from lithium hydroxide, potassium hydroxide, sodium hydroxide, and a combination thereof.

101. The process according to embodiment 100, wherein the base is sodium hydroxide.

102. The process according to any one of embodiments 70, 74, and 79 to 101, wherein step (v) comprises reacting C58A or a pharmaceutically acceptable salt thereof or C58B or a pharmaceutically acceptable salt thereof with a base in the presence of a solvent selected from piperidine, N-formylpiperidine, 2,2,6,6-tetramethylpiperidine, pyridine, and a combination thereof.

103. The process according to embodiment 102, wherein the solvent is piperidine.

104. The process according to any one of embodiments 70 to 103, wherein the process can be further defined with the additional reaction steps, reagents and conditions recited in any one of embodiments 22 to 65.

105. A process for preparing A1:

A1

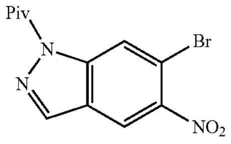

or a pharmaceutically acceptable salt thereof, comprising:

(a1) reacting

A0

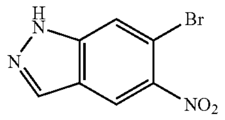

or a pharmaceutically acceptable salt thereof with pivaloyl chloride to form A1 or a pharmaceutically acceptable salt thereof.

106. A process for preparing B1:

B1

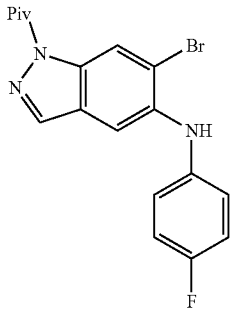

or a pharmaceutically acceptable salt thereof, comprising:

(a1) reacting

A0

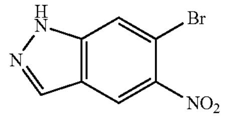

or a pharmaceutically acceptable salt thereof with pivaloyl chloride to form

A1

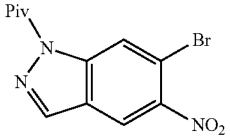

or a pharmaceutically acceptable salt thereof; and (a2) reacting A1 or a pharmaceutically acceptable salt thereof with 4-fluorophenylboronic acid to form B1 or a pharmaceutically acceptable salt thereof.

107. The process according to embodiment 69 or embodiment 70, wherein the process can be further defined with the additional reaction steps, reagents and conditions recited in any one of embodiments 23 to 43.

108. A process for preparing E1:

E1

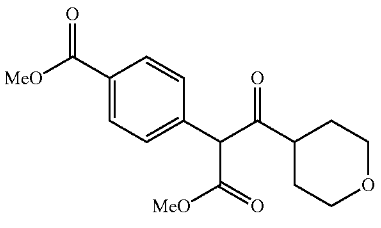

comprising:

(b1) reacting

F1

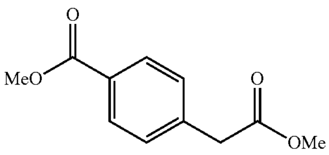

with oxane-4-carbonyl chloride to form E1.

109. A process for preparing D1:

D1

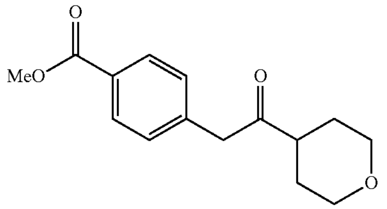

comprising:

(b1) reacting

F1

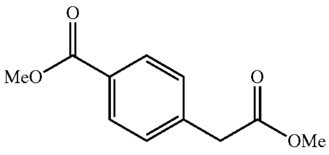

with oxane-4-carbonyl chloride to form

E1

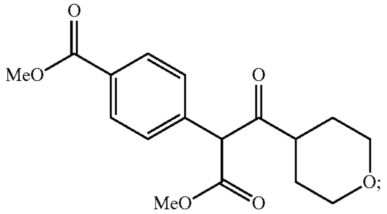

(b2) reacting E1 with an aqueous solution (e.g., an aqueous solution comprising chloride (e.g., sodium chloride, lithium chloride)) to form D1.

110. The process according to embodiment 72 or embodiment 73, wherein the process can be further defined with the additional reaction steps, reagents and conditions recited in any one of embodiments 47 to 60.

111. A process for preparing C13:

C13

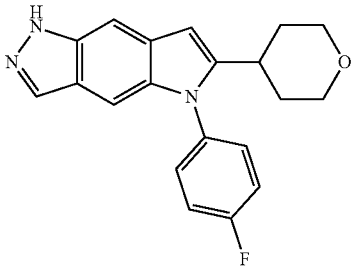

or a pharmaceutically acceptable salt thereof, comprising:

(a1) reacting

H184

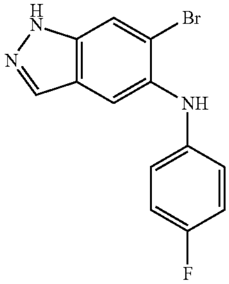

or a pharmaceutically acceptable salt thereof with trimethyl((tetrahydro-2H-pyran-4-yl)ethynyl)silane to form

C12

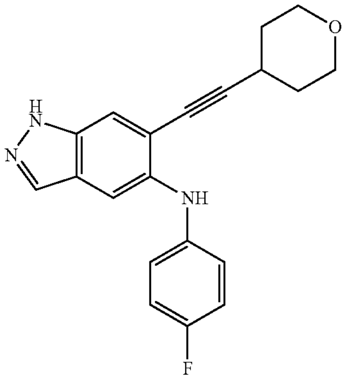

or a pharmaceutically acceptable salt thereof;

(a2) reacting C12 or a pharmaceutically acceptable salt thereof with an acid to yield C13 or a pharmaceutically acceptable salt thereof.

112. The process according to embodiment 111, wherein step (a1) comprises reacting H184 or a pharmaceutically acceptable salt thereof with trimethyl((tetrahydro-2H-pyran-4-yl)ethynyl)silane in the presence of copper iodide.

113. The process according to embodiment 111 or embodiment 112, wherein step (a1) comprises reacting H184 or a pharmaceutically acceptable salt thereof with trimethyl((tetrahydro-2H-pyran-4-yl)ethynyl)silane in the presence of a palladium-phosphine complex-based catalyst, an alcohol, and a base.

114. The process according to embodiment 113, wherein the palladium-phosphine complex-based catalyst is bis(triphenylphosphine)palladium(II) dichloride.

115. The process according to embodiment 113 or embodiment 114, wherein the alcohol is selected from 1-butanol, ethanol, 2-propanol, and a combination thereof.

116. The process according to any one of embodiments 113 to 115, wherein the alcohol is 2-propanol.

117. The process according to any one of embodiments 113 to 116, wherein the base is selected from sodium hydroxide, lithium hydroxide, potassium hydroxide, and a combination thereof.

118. The process according to any one of embodiments 113 to 117, wherein the base is potassium hydroxide.

119. The process according to any one of embodiments 111 to 118, wherein step (a1) comprises reacting H184 or a pharmaceutically acceptable salt thereof with trimethyl((tetrahydro-2H-pyran-4-yl)ethynyl)silane at about 70-85° C.

120. The process according to any one of embodiments 111 to 119, wherein step (a2) comprises reacting $Cl_2$ or a pharmaceutically acceptable salt thereof with an acid at about 70-85° C.

121. The process according to any one of embodiments 111 to 120, wherein step (a2) comprises reacting C12 or a pharmaceutically acceptable salt thereof with acetic acid.

122. A process for preparing C58B:

C58B

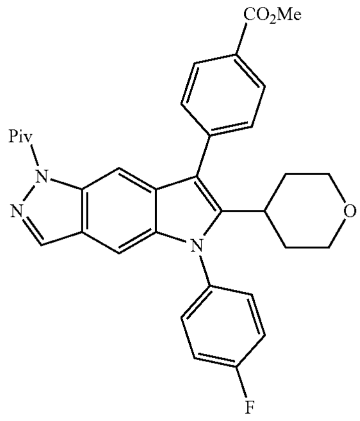

or a pharmaceutically acceptable salt thereof, comprising:

(a) reacting

B1

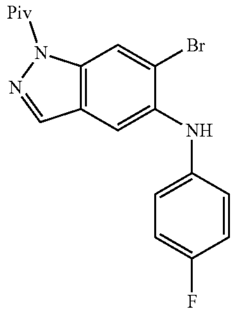

or a pharmaceutically acceptable salt thereof with

D1

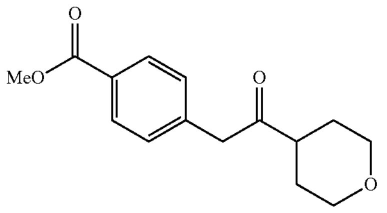

to form

G1

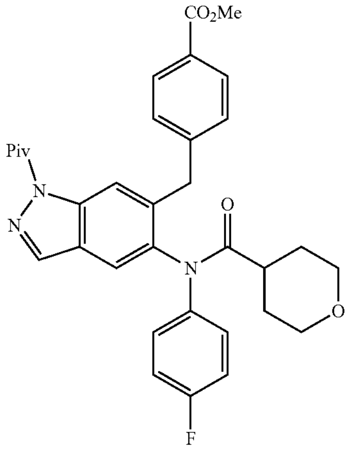

or a pharmaceutically acceptable salt thereof; and (b) reacting G1 or a pharmaceutically acceptable salt thereof with a base in the presence of a solvent to form C58B.

123. The process according to embodiment 122, wherein step (b) comprises reacting G1 or a pharmaceutically acceptable salt thereof with a base at about −40° C. to about 20° C. (e.g., −35° C.).

124. The process according to embodiment 122 or embodiment 123, wherein the base is selected from lithium hexamethyldisilazide, potassium tert-butoxide, lithium diisopropylamide, and a combination thereof.

125. The process according to any one of embodiments 122 to 124, wherein the base is lithium hexamethyldisilazide.

126. The process according to any one of embodiments 122 to 125, wherein the solvent is selected from tetrahydrofuran, tetrahydropyran, 1,3-dioxolane, and a combination thereof (e.g., tetrahydrofuran).

127. The process according to any one of embodiments 122 to 126, wherein step (a) comprises reacting B1 or a pharmaceutically acceptable salt thereof with D1 in the presence of a palladium-phosphine complex-based catalyst, a base selected from tripotassium phosphate, potassium carbonate, and cesium carbonate, and a solvent selected from tetrahydrofuran, 2-methyltetrahydrofuran, cyclopentyl methyl ether, toluene, dimethylformamide, acetonitrile, propionitrile, and a combination thereof.

128. The process according to embodiment 127, wherein the palladium-phosphine complex-based catalyst is selected from XPhos Pd, tBuXPhos Pd, BrettPhos Pd, tBuBrettPhos Pd, bis(tri-t-butylphosphine) Pd, di-adamantylalkylphosphine Pd, 2-(di-tert-butylphosphino)-1-(2-methoxyphenyl)-1H-pyrrole Pd, and bis(triphenylphosphine)Pd dichloride.

129. The process according to embodiment 127 or embodiment 128, wherein the palladium-phosphine complex-based catalyst is selected from XPhos Pd, tBuXPhos Pd, BrettPhos Pd, tBuBrettPhos Pd, bis(tri-t-butylphosphine) Pd, and bis(triphenylphosphine)Pd dichloride.

130. The process according to embodiment 127 or embodiment 128, wherein the palladium-phosphine complex-based catalyst is selected from XPhos Pd, BrettPhos Pd, di-adamantylalkylphosphine Pd, and 2-(di-tert-butylphosphino)-1-(2-methoxyphenyl)-1H-pyrrole Pd.

131. The process according to any one of embodiments 127 to 129, wherein the palladium-phosphine complex-based catalyst is bis(tri-t-butylphosphine) Pd.

132. The process according to any one of embodiments 122 to 131, wherein step (a) comprises reacting B1 or a pharmaceutically acceptable salt thereof with D1 at about 45-100° C.

133. A compound

G1

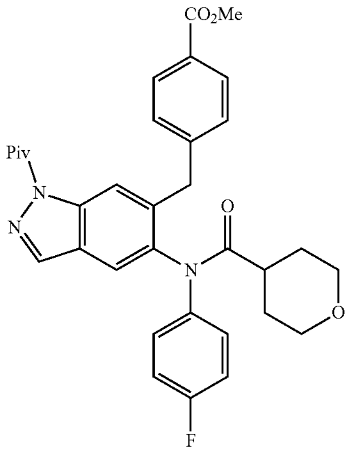

or a pharmaceutically acceptable salt thereof.

134. The process according to any one of embodiments 70 to 77, wherein $C_{13}$ or a pharmaceutically acceptable salt thereof is alternatively produced by a process comprising:

(c1) reacting 5-bromo-6-iodo-1H-indazole with trimethyl((tetrahydro-2H-pyran-4-yl)ethnyl)silane to form 5-bromo-6-((tetrahydro-2H-pyran-4-yl)ethynyl)-1H-indazole;

(c2) reacting 5-bromo-6-((tetrahydro-2H-pyran-4-yl)ethynyl)-1H-indazole with 4-fluoroaniline to form N-(4-fluorophenyl)-6-((tetrahydro-2H-pyran-4-yl)ethynyl)-1H-indazol-5-amine; and (c3) reacting N-(4-fluorophenyl)-6-((tetrahydro-2H-pyran-4-yl)ethynyl)-1H-indazol-5-amine with an acid (e.g., AcOH) to form C13 or a pharmaceutically acceptable salt thereof.

135. The process according to embodiment 134, wherein step (c1) takes place at about 70-80° C. (e.g., about 75° C.).

136. The process according to embodiment 134 or embodiment 135, wherein step (c1) comprises reacting 5-bromo-6-iodo-1H-indazole with trimethyl((tetrahydro-2H-pyran-4-yl)ethnyl)silane in the presence of an organic solvent selected from DMF, EtOH, MeOH, 1-butanol, tert-butanol, isopropyl alcohol (IPA), tAmOH, a THF/alcohol mixture, and a 2-MeTHF alcohol mixture (e.g., EtOH), a base selected from NaOH, KOH, $K_2CO_3$, $Na_2CO_3$, $Cs_2CO_3$ NaOtBu, KOtBu, and DBU (1,8-Diazabicyclo(5.4.0)undec-7-ene) (e.g., KOH), and a catalyst selected from $Pd(PPh_3)_4$, CuI, CuI/$PPh_3$, and water (e.g., $Pd(PPh_3)_4$).

137. The process according to any one of embodiments 134 to 136, wherein step (c2) takes place at about 60-70° C. (e.g., about 65° C.).

138. The process according to any one of embodiments 134 to 137, wherein step (c2) comprises reacting 5-bromo-6-((tetrahydro-2H-pyran-4-yl)ethynyl)-1H-indazole with 4-fluoroaniline to form N-(4-fluorophenyl)-6-((tetrahydro-2H-pyran-4-yl)ethynyl)-1H-indazol-5-amine in the presence of a catalyst selected from PdtBuXPhos G1-4; $(PdOAc)_2$, Pd(cinnamyl)$Cl_2$ with ligands, BrettPhos, SPHos, XPhos, XantPhos, Pd(dppf)$Cl_2CH_2Cl_2$, JosiPhos, and cataCXium® A (e.g., PdtBuXPhos), a organic solvent selected from EtOH, MeOH, 1-butanol, tert-butanol, isopropyl alcohol (IPA), tAmOH, THF, 2-MeTHF, CPMe, Toluene, DMF, ACN, DMA, and diglyme (e.g., EtOH), and a base selected from NaOH, $K_3PO_4$, $K_2CO_3$, NaOtBu, KOtBu, and NaOEt (e.g., NaOtBu).

Previously Disclosed Synthesis Processes of Compound 2

As mentioned above, synthesis processes of Compound 2 and pharmaceutically acceptable salts thereof are provided in International Patent Application Publication No. WO 2020/081257. These processes as described in WO 2020/081257 are depicted in Scheme 2 below. Alternative reaction steps are indicated with dashed arrows.

Scheme 2 - Part A: Synthesis of Intermediate T4
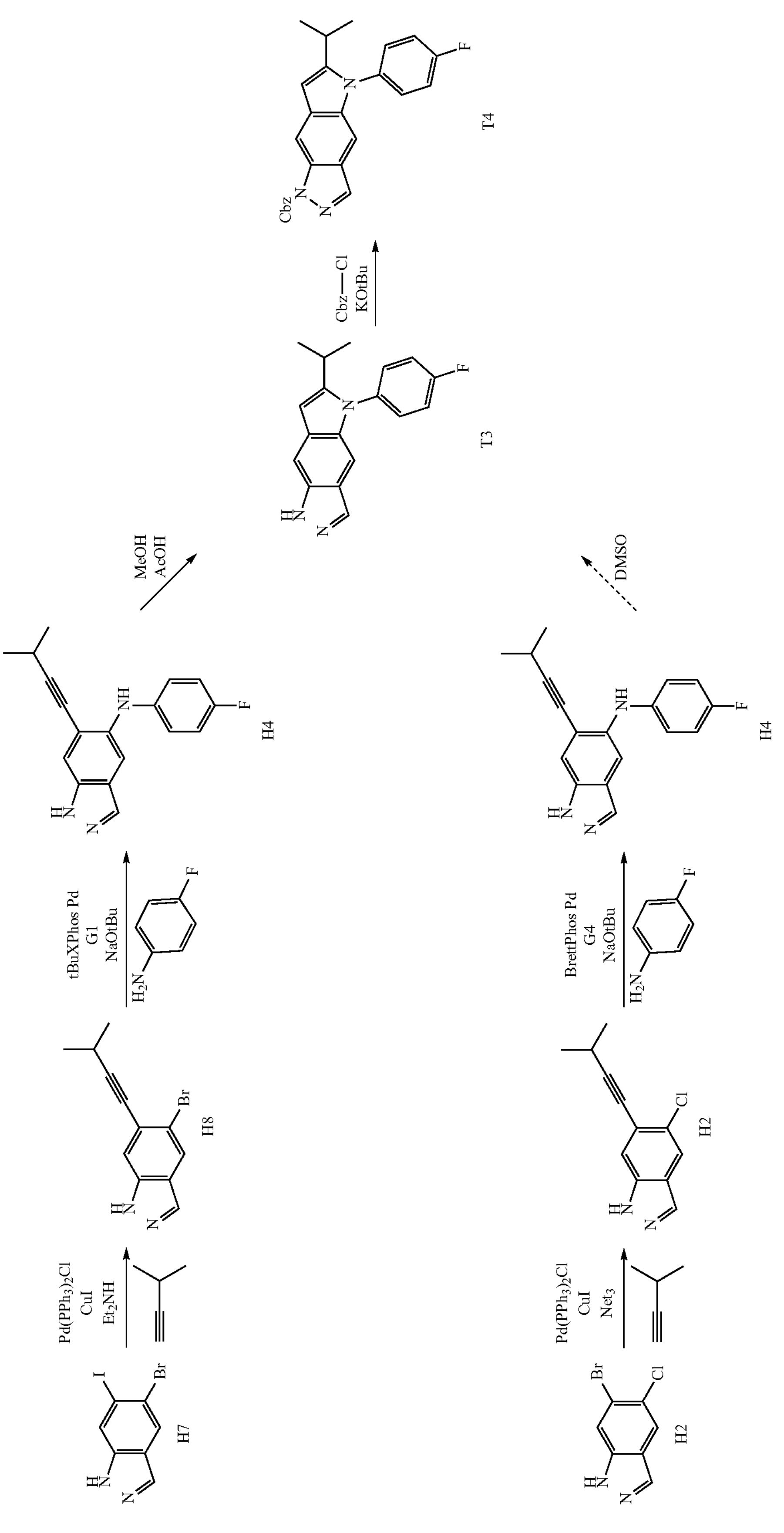
H7
H8
H4
T3
T4
H2
H2
H4

Scheme 2 - Part B: Synthesis of Compound 2 from Intermediate T4

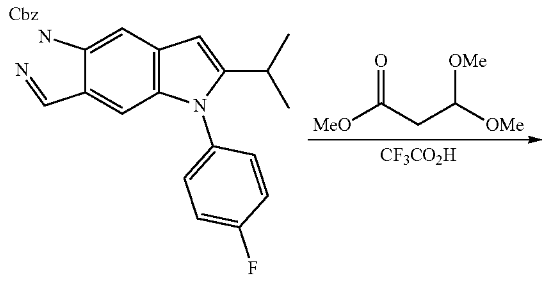

T4

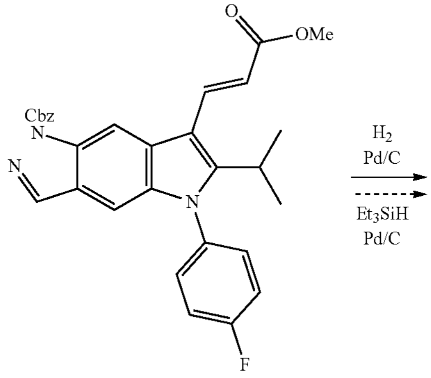

H35

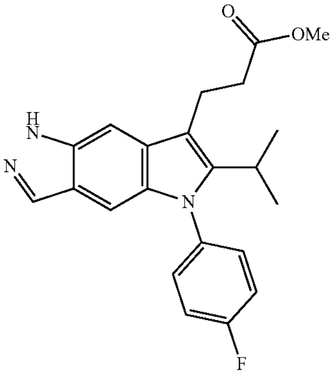

H36

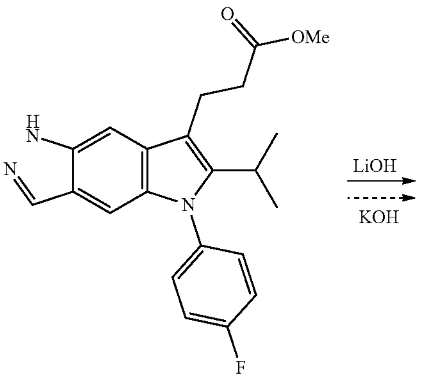

H36

-continued

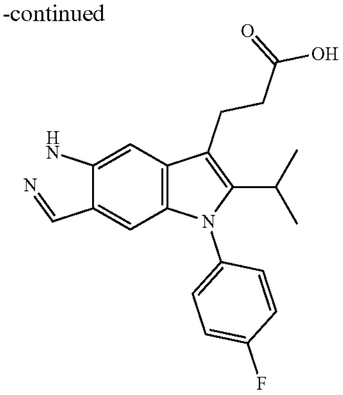

Compound 2

Referring to Scheme 2 above, the synthesis processes as described in WO 2020/081257 can be divided into two parts: Part A that culminates in the formation of the key intermediate T4 (benzyl 5-(4-fluorophenyl)-6-isopropylpyrrolo[2,3-f]indazole-1(5H)-carboxylate) and Part B that culminates in the synthesis of Compound 2 from the intermediate T4 derived from Part A. To summarize, in Part A, there are two options for the starting material, namely 5-bromo-6-iodo-1H-indazole (H7) or 6-bromo-5-chloro-1H-indazole (1). Either H7 or H1 is reacted with 3-methylbut-1-yne in the presence of copper iodide (CuI), Pd(PPh$_3$)$_2$Cl$_2$ as a catalyst, and either di- or tri-ethylamine. This step yields a 5-halo-6-(3-methylbut-1-yn-1-yl)-1H-indazole that is H8 or H2, which is further reacted with 4-fluoroaniline in the presence of sodium t-butoxide (NaOtBu) (1.3 g, 13.0 mmol), and a palladium-phosphine complex-based catalyst (i.e., tBuXPhos Pd G1 or BrettPhos Pd G4) to afford the product N-(4-fluorophenyl)-6-(3-methylbut-1-yn-1-yl)-1H-indazol-5-amine (H4) in solution (as determined by HPLC analysis). At this point, the two alternative routes of Part A have converged and the H4 solution is diluted and washed with different solvents and then concentrated in vacuo. The solids are filtered and dried to obtain T3 (5-(4-fluorophenyl)-6-isopropyl-1H-pyrrolo[2,3-f]indazole) as a solid. T3 is then reacted with benzyl chloroformate (Cbz-C1) in the presence of potassium t-butoxide (KOtBu), and the resulting slurry is diluted with methyl tert-butyl ether (MTBE) and water. The organic layer is slurried in methanol (MeOH), cooled overnight, collected, and dried to afford the key intermediate T4 as a light yellow solid. The main objective of converting T3 to T4 is to incorporate the carboxybenzyl (CBz) protecting group, which prevents the methyl 3,3-dimethoxypropanoate, which is a reagent in the next reaction step in Part B as described below, from reacting at the wrong position of the intermediate.

In Part B, T4 is reacted with methyl 3,3-dimethoxypropanoate and trifluoroacetic acid to afford benzyl 5-(4-fluorophenyl)-6-isopropyl-7-[(E)-3-methoxy-3-oxo-prop-1-enyl]pyrrolo[2,3-f]indazole-1-carboxylate (H35). 10% palladium on carbon (Pd/C) catalyst is added to H35 and the mixture is either placed under an atmosphere of hydrogen or triethylsilane (Et$_3$SiH) is added to the mixture, in order to afford the product H36 (methyl 3-[5-(4-fluorophenyl)-6-isopropyl-1H-pyrrolo[2,3-f]indazol-7-yl]propanoate). Finally, an aqueous solution of lithium hydroxide (LiOH) or potassium hydroxide (KOH) is added to a H36 solution to convert the —C(═O)OMe ester group to —C(═O)OH. After 1 hour, the reaction mixture is concentrated in vacuo, washed, acidified to ~pH 3-4, and extracted with ethyl acetate (EtOAc). The precipitate resulting from the EtOAc addition is filtered and dried under vacuum to afford the product as a Compound 2 solid.

Non-Limiting Advantages of New Processes of Preparing Compound 2

The present disclosure provides further alternative processes for preparing a solid form of Compound 2 or a pharmaceutically acceptable salt thereof that can be distinguished from previously disclosed processes in several aspects. For instance, T4 with the carboxybenzyl (CBz) protecting group is a key intermediate that is common to all previously disclosed processes. The step of introducing the CBz protecting group is common to the previously disclosed processes, specifically the step of reacting T3 with CBz-Cl in the presence of KOtBu as depicted in Scheme 2. In contrast, the processes provided herein bypass this reaction step of incorporating the CBz protecting group in the intermediates and no longer form T4 and other downstream compounds (e.g., H35 and H36) as intermediates. Instead, a new intermediate (e.g., I1 in the non-limiting exemplary embodiments and in Scheme 7B) is formed in the processes described herein. From a chemistry standpoint, it is significant that even though in this new process, methyl 3,3-dimethoxypropanoate is still being used to introduce the —C(═O)OMe ester group onto an intermediate I1, there is no need to use a protecting group to prevent methyl 3,3-dimethoxypropanoate from reacting at the wrong position on T3.

From an economic standpoint, the key advantage of bypassing one or more reaction steps is that such a process, especially when preparing a compound on a large scale, would be significantly more efficient in terms of cost, time, and energy use. Moreover, in some embodiments, at least one other intermediate need not be isolated and purified and the process can proceed directly to the next reaction step (see e.g., Example 5 where H184 need not be isolated). As discussed above, Compound 2 is being investigated for medical uses. As the drug moves to higher phase clinical studies with larger subject populations and when the drug is approved and becomes accessible to the public, the advantages of a cost-, time-, and energy-efficient Compound 2 synthesis process would be even more clearly manifested.

Secondly, some embodiments of the processes described herein incorporate starting materials and reagents that are different from those in the previously disclosed processes. For instance, Example 5 below utilizes a starting material having a pivaloyl (Piv) protecting group and having a nitro group and a halogen as substituents (J1, also referred to as A1 herein). This contrasts against the starting materials in the previously disclosed processes, which possess halogen groups as substituents (H2 or H7). Furthermore, the starting material in Example 5 below is reacted with a phenylboronic acid in the presence of a siloxane (i.e., with a —Si—O—Si-linkage) and an oxophosphetane catalyst (see Step 1A of Scheme 7), to form phenyl-indazolamine intermediates K1 (also referred to as B1 herein) and H184. These initial reaction steps in the process described in Example 5 utilize reagents and catalysts that have not been previously described and afford phenyl-indazolamine intermediates which are also not present in the previously described processes. The last phenyl-indazolamine intermediate H184 in Example 5 is then reacted with a silane in a subsequent reaction step, which is yet another class of reagent not described in the corresponding reaction step(s) of the previously disclosed processes.

The alternative processes for preparing a solid form of Compound 2 or a pharmaceutically acceptable salt thereof are described in greater detail in the following non-limiting exemplary embodiments and also the appended Examples 5 and 6.

Non-Limiting Exemplary Embodiments (Compound 2 Processes)

1. A process for preparing a solid form of Compound 2

(Compound 2)

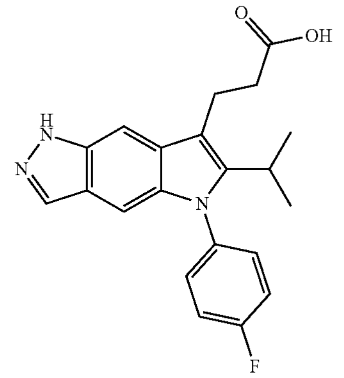

or a pharmaceutically acceptable salt thereof, comprising:

(a) reacting

T3

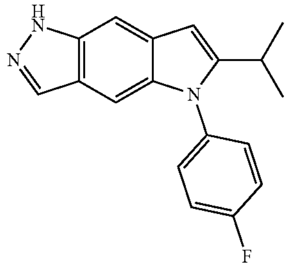

or a pharmaceutically acceptable salt thereof with methyl 3,3-dimethoxypropanoate to form

I1

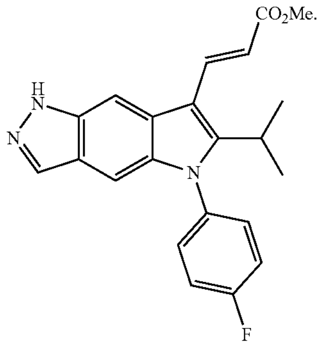

or a pharmaceutically acceptable salt thereof, (b) reducing I1 or a pharmaceutically acceptable salt thereof to

H36

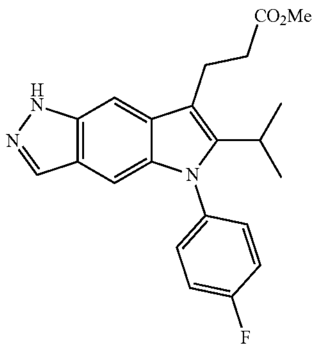

or a pharmaceutically acceptable salt thereof; and (c) de-esterifying H36 or a pharmaceutically acceptable salt thereof to yield the solid form of Compound 2 or a pharmaceutically acceptable salt thereof.

2. The process according to embodiment 1, wherein step (a) comprises reacting T3 or a pharmaceutically acceptable salt thereof with methyl 3,3-dimethoxypropanoate in the presence of a sulfonic acid and a solvent or a solvent system selected from dichloromethane, trifluoromethylbenzene, 2-methyltetrahydrofuran, propan-2-one/cyclopentane mixture, ethyl acetate/ethanol mixture, and a combination thereof.

3. The process according to embodiment 2, wherein the solvent is dichloromethane.

4. The process according to embodiment 2 or embodiment 3, wherein the sulfonic acid is selected from p-toluenesulfonic acid, p-toluenesulfonic acid monohydrate, camphorsulfonic acid, triflic acid, and a combination thereof (e.g., selected from p-toluenesulfonic acid, camphorsulfonic acid, triflic acid, and a combination thereof; p-toluenesulfonic acid).

5. The process according to embodiment 4, wherein the sulfonic acid isp-toluenesulfonic acid monohydrate.

6. The process according to any one of embodiments 1 to 5, wherein step (a) comprises reacting T3 or a pharmaceutically acceptable salt thereof with methyl 3,3-dimethoxypropanoate at about 40-50° C. and with agitation.

7. The process according to any one of embodiments 1 to 6, wherein step (b) comprises reducing I1 or a pharmaceutically acceptable salt thereof with a reducing agent selected from hydrogen gas and a silicon-based reducing agent and in the presence of a palladium catalyst.

8. The process according to embodiment 7, wherein the palladium catalyst is a catalyst comprising palladium supported on activated carbon.

9. The process according to embodiment 7 or embodiment 8, wherein the reducing agent is hydrogen gas.

10. The process according to embodiment 7 or embodiment 8, wherein the reducing agent is a silicon-based reducing agent and the silicon-based reducing agent is selected from triethylsilane, trichlorosilane, methyldichlorosilane, dimethylchlorosilane, triphenylsilane, tris (trimethylsilyl)silane, and a combination thereof.

11. The process according to embodiment 9, wherein step (b) comprises reducing I1 or a pharmaceutically acceptable salt thereof with hydrogen gas in the presence of tetramethylethylenediamine and a solvent selected from tetrahydrofuran, 2-methyltetrahydrofuran, cyclopentyl methyl ether, and a combination thereof.

12. The process according to embodiment 11, wherein the solvent is tetrahydrofuran.

13. The process according to embodiment 11 or embodiment 12, wherein step (b) comprises reducing I1 or a pharmaceutically acceptable salt thereof with hydrogen gas at a pressure level of about 1-10 bar.

14. The process according to embodiment 10, wherein step (b) comprises reducing I1 or a pharmaceutically acceptable salt thereof with the silicon-based reducing agent in the presence of an alcohol selected from methanol, ethanol, isopropyl alcohol, tert-butyl alcohol, and a combination thereof.

15. The process according to any one of embodiments 1 to 14, wherein step (b) comprises reducing I1 or a pharmaceutically acceptable salt thereof at about 25-35° C.

16. The process according to any one of embodiments 1 to 15, wherein step (c) comprises de-esterifying H36 or a pharmaceutically acceptable salt thereof with a base selected from lithium hydroxide, potassium hydroxide, sodium hydroxide, and a combination thereof.

17. The process according to embodiment 16, wherein the base is potassium hydroxide.

18. The process according to embodiment 16 or embodiment 17, wherein step (c) comprises de-esterifying H36 or a pharmaceutically acceptable salt thereof with a base (e.g., potassium hydroxide) in the presence of an alcohol selected from methanol, ethanol, isopropyl alcohol, tert-butyl alcohol, and a combination thereof.

19. The process according to embodiment 18, wherein the alcohol is ethanol.

20. The process according to any one of embodiments 1 to 19, wherein step (c) comprises de-esterifying H36 or a pharmaceutically acceptable salt thereof at 20-30° C.

21. The process according to any one of embodiments 1 to 20, wherein the process further comprises at least one additional step selected from:

(a0) reacting

J0

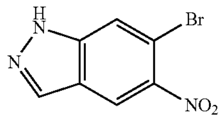

or a pharmaceutically acceptable salt thereof with pivaloyl chloride to form

J1

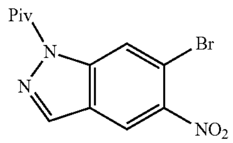

or a pharmaceutically acceptable salt thereof;

(a1) reacting J1 or a pharmaceutically acceptable salt thereof with 4-fluorophenylboronic acid to form

K1

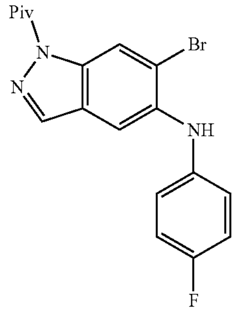

or a pharmaceutically acceptable salt thereof; and (a2) deprotecting K1 or a pharmaceutically acceptable salt thereof and adding trimethyl(3-methylbut-1-yn-1-yl)silane to form T3 or a pharmaceutically acceptable salt thereof.

22. The process according to embodiment 21, wherein step (a0) comprises reacting J0 or a pharmaceutically acceptable salt thereof with pivaloyl chloride in the presence of a base and a solvent selected from selected from tetrahydrofuran, 2-methyltetrahydrofuran, cyclopentyl methyl ether, and a combination thereof.

23. The process according to embodiment 22, wherein the solvent is tetrahydrofuran.

24. The process according to embodiment 22 or embodiment 23, wherein the base is selected from sodium tert-butoxide, potassium tert-butoxide, sodium tert-amylate, and a combination thereof (e.g., sodium tert-amylate).

25. The process according to embodiment 24, wherein the base is potassium tert-butoxide.

26. The process according to any one of embodiments 21 to 25, wherein step (a0) comprises reacting J0 or a pharmaceutically acceptable salt thereof with pivaloyl chloride at about 10-20° C.

27. The process according to any one of embodiments 21 to 26, wherein step (a1) comprises reacting J1 or a pharmaceutically acceptable salt thereof with 4-fluorophenylboronic acid in the presence of a phosphetane oxide catalyst and a reducing agent.

28. The process according to embodiment 27, wherein the phosphetane oxide catalyst is hexamethyloxophosphetane.

29. The process according to embodiment 27 or embodiment 28, wherein the reducing agent is a silicon-based reducing agent selected from triethylsilane, trichlorosilane, methyldichlorosilane, dimethylchlorosilane, triphenylsilane, tris(trimethylsilyl)silane, dimethylsilyloxy(dimethyl)silane, and a combination thereof.

30. The process according to embodiment 29, wherein the reducing agent is dimethylsilyloxy(dimethyl)silane.

31. The process according to any one of embodiments 27 to 30, wherein step (a2) comprises deprotecting K1 or a pharmaceutically acceptable salt thereof with a base selected from lithium hydroxide, potassium hydroxide, sodium hydroxide, and a combination thereof.

32. The process according to embodiment 31, wherein the base is potassium hydroxide.

33. The process according to any one of embodiments 27 to 32, wherein step (a1) comprises reacting J1 or a pharmaceutically acceptable salt thereof with 4-fluorophenylboronic acid at about 85-95° C.

34. The process according to any one of embodiments 27 to 33, wherein step (a2) comprises deprotecting K1 or a pharmaceutically acceptable salt thereof to form

H184

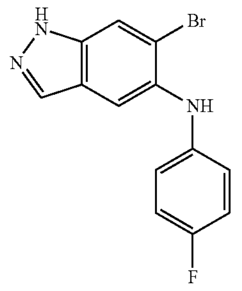

or a pharmaceutically acceptable salt thereof and reacting H184 or a pharmaceutically acceptable salt thereof with trimethyl(3-methylbut-1-yn-1-yl)silane.

35. The process according to embodiment 34, wherein step (a2) comprises reacting H184 or a pharmaceutically acceptable salt thereof with trimethyl(3-methylbut-1-yn-1-yl)silane in the presence of a palladium-phosphine complex-based catalyst, copper iodide, a base, and an alcohol.

36. The process according to embodiment 35, wherein the base is selected from lithium hydroxide, potassium hydroxide, sodium hydroxide, and a combination thereof.

37. The process according to embodiment 36, wherein the base is potassium hydroxide.

38. The process according to embodiment 35, wherein the alcohol is selected from methanol, ethanol, isopropyl alcohol, tert-butyl alcohol, and a combination thereof.

39. The process according to embodiment 38, wherein the alcohol is isopropyl alcohol.

40. The process according to embodiment 35, wherein the palladium-phosphine complex-based catalyst is selected from XPhos Pd, tBuXPhos Pd, BrettPhos Pd, tBuBrettPhos Pd, and bis(triphenylphosphine)Pd dichloride.

41. The process according to embodiment 40, wherein the palladium-phosphine complex-based catalyst is bis(triphenylphosphine)Pd dichloride.

42. The process according to any one of embodiments 34 to 41, wherein step (a2) comprises deprotecting K1 or a pharmaceutically acceptable salt thereof and reacting H184 or a pharmaceutically acceptable salt thereof with trimethyl(3-methylbut-1-yn-1-yl)silane at about 75-85° C.

43. The process according to any one of embodiments 1 to 20, wherein the process further comprises at least one additional step selected from:

(a0) reacting

J0

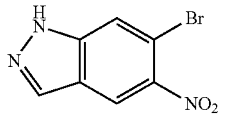

or a pharmaceutically acceptable salt thereof with 4-fluorophenylboronic acid to form

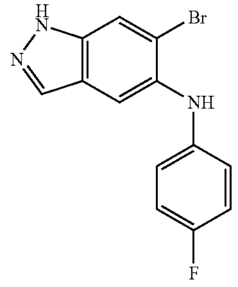

H184 or a pharmaceutically acceptable salt thereof; and (a1) reacting H184 or a pharmaceutically acceptable salt thereof with trimethyl(3-methylbut-1-yn-1-yl)silane to form

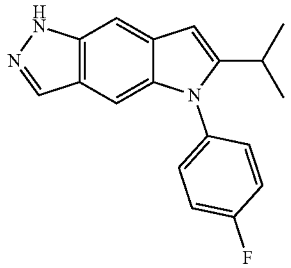

T3 or a pharmaceutically acceptable salt thereof.

44. The process according to embodiment 43, wherein step (a0) comprises reacting J0 or a pharmaceutically acceptable salt thereof with 4-fluorophenylboronic acid in the presence of a catalyst, a reducing agent, and a solvent selected from toluene, isopropanol, xylene, methyl cyclohexane, cyclopentyl methyl ether, methyl tert-butyl ether, isopropyl acetate, tetrahydrofuran, an aqueous solution comprising sodium carbonate and/or potassium carbonate (e.g., a sodium chloride aqueous solution comprising sodium carbonate and/or potassium carbonate), and a combination thereof (e.g., an isopropanol/toluene mixture).

45. The process according to embodiment 44, wherein the catalyst is selected from hexamethyloxophosphetane, $(MoO_2Cl_2)DMF_2$ with $PPh_3$ or a silane, 4-methyl-1-phenyl-2,3-dihydrophosphole 1-oxide 4, (2R,5R)-1-{2-[(2R,5R)-2,5-diethylphospholan-1-yl]phenyl}-2,5-diethyl-1-phospholan-1-one, and 1-(adamantan-1-ylphosphoroso)adamantane.

46. The process according to embodiment 44 or 45, wherein the catalyst is a phosphetane oxide catalyst.

47. The process according to embodiment 46, wherein the phosphetane oxide catalyst is hexamethyloxophosphetane.

48. The process according to any one of embodiments 44 to 47, wherein the solvent is selected from toluene, cyclopentyl methyl ether, isopropyl acetate, tetrahydrofuran, and a combination thereof.

49. The process according to any one of embodiments 44 to 48, wherein the solvent is toluene.

50. The process according to any one of embodiments 44 to 49, wherein the reducing agent is selected from triethylsilane, trichlorosilane, polymethylsilane, methyldichlorosilane, dimethylchlorosilane, phenylsilane, triphenylsilane, triphenylphosphine, triphenylphosphine oxide, tris(trimethylsilyl)silane, dimethylsilyloxy(dimethyl)silane, and a combination thereof.

51. The process according to any one of embodiments 44 to 50, wherein the reducing agent is selected from polymethylsilane, phenylsilane, triphenylphosphine, triphenylphosphine oxide, dimethylsilyloxy(dimethyl)silane, and a combination thereof.

52. The process according to any one of embodiments 44 to 49, wherein the reducing agent is a silicon-based reducing agent selected from triethylsilane, trichlorosilane, methyldichlorosilane, dimethylchlorosilane, triphenylsilane, tris(trimethylsilyl)silane, dimethylsilyloxy(dimethyl)silane, and a combination thereof.

53. The process according to embodiment 52, wherein the reducing agent is dimethylsilyloxy(dimethyl)silane.

54. The process according to any one of embodiments 43 to 53, wherein step (a0) comprises reacting J0 or a pharmaceutically acceptable salt thereof with 4-fluorophenylboronic acid at about 85-105° C. (e.g., about 90-100° C.).

55. The process according to any one of embodiments 43 to 54, wherein step (a0) further comprises cooling the reaction mixture and adding an aqueous mixture comprising a base.

56. The process according to embodiment 55, wherein the base is sodium hydroxide, potassium hydroxide, or aqueous potassium carbonate.

57. The process according to any one of embodiments 43 to 56, wherein step (a1) comprises reacting H184 or a pharmaceutically acceptable salt thereof with trimethyl(3-methylbut-1-yn-1-yl)silane in the presence of a palladium-phosphine complex-based catalyst, copper iodide, a base, and an alcohol.

58. The process according to embodiment 57, wherein the base is selected from lithium hydroxide, potassium hydroxide, sodium hydroxide, and a combination thereof.

59. The process according to embodiment 58, wherein the base is potassium hydroxide.

60. The process according to any one of embodiments 43 to 59, wherein the alcohol is selected from methanol, ethanol, isopropyl alcohol, tert-butyl alcohol, and a combination thereof.

61. The process according to embodiment 60, wherein the alcohol is isopropyl alcohol.

62. The process according to any one of embodiments 43 to 61, wherein the palladium-phosphine complex-based catalyst is selected from XPhos Pd, tBuXPhos Pd, BrettPhos Pd, tBuBrettPhos Pd, and bis(triphenylphosphine)Pd dichloride.

63. The process according to embodiment 62, wherein the palladium-phosphine complex-based catalyst is bis(triphenylphosphine)Pd dichloride.

64. The process according to any one of embodiments 43 to 63, wherein step (a1) reacting H184 or a pharmaceutically acceptable salt thereof with trimethyl(3-methylbut-1-yn-1-yl)silane at about 70-85° C. (e.g., 75-80° C.).

65. The process according to any one of embodiments 1 to 20, wherein the process further comprises at least one additional step selected from:

(a1') reacting

H7

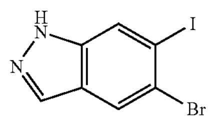

or a pharmaceutically acceptable salt thereof with trimethyl (3-methylbut-1-yn-1-yl)silane to form

H8

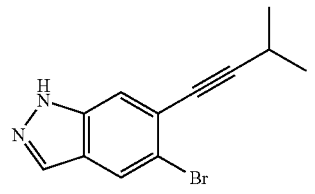

or a pharmaceutically acceptable salt thereof, and (a2') reacting H8 or a pharmaceutically acceptable salt thereof with 4-fluoroaniline to form T3 or a pharmaceutically acceptable salt thereof.

66. The process according to embodiment 65, wherein step (a1') comprises reacting H7 or a pharmaceutically acceptable salt thereof with trimethyl(3-methylbut-1-yn-1-yl)silane in the presence of a palladium-phosphine complex-based catalyst, copper iodide, a base, and an alcohol.

67. The process according to embodiment 66, wherein the base is selected from lithium hydroxide, potassium hydroxide, sodium hydroxide, and a combination thereof.

68. The process according to embodiment 67, wherein the base is potassium hydroxide.

69. The process according to embodiment 66, wherein the alcohol is selected from methanol, ethanol, isopropyl alcohol, tert-butyl alcohol, and a combination thereof.

70. The process according to embodiment 69, wherein the alcohol is ethanol.

71. The process according to embodiment 66, wherein the palladium-phosphine complex-based catalyst is selected from XPhos Pd, tBuXPhos Pd, BrettPhos Pd, tBuBrettPhos Pd, and bis(triphenylphosphine)Pd dichloride.

72. The process according to embodiment 71, wherein the palladium-phosphine complex-based catalyst is bis(triphenylphosphine)Pd dichloride.

73. The process according to any one of embodiments 66 to 72, wherein step (a1') comprises reacting H7 or a pharmaceutically acceptable salt thereof with trimethyl (3-methylbut-1-yn-1-yl)silane at about 70-80° C.

74. The process according to any one of embodiments 66 to 73, wherein step (a2') comprises reacting H8 or a pharmaceutically acceptable salt thereof with 4-fluoroaniline in the presence of a palladium-phosphine complex-based catalyst, copper iodide, a base, and an alcohol.

75. The process according to embodiment 74, wherein the base is selected from sodium tert-butoxide, potassium tert-butoxide, sodium tert-amylate, and a combination thereof.

76. The process according to embodiment 75, wherein the base is sodium tert-butoxide.

77. The process according to embodiment 74, wherein the alcohol is selected from methanol, ethanol, isopropyl alcohol, tert-butyl alcohol, and a combination thereof.

78. The process according to embodiment 77, wherein the alcohol is ethanol.

79. The process according to embodiment 74, wherein the palladium-phosphine complex-based catalyst is selected from XPhos Pd, tBuXPhos Pd, BrettPhos Pd, tBuBrettPhos Pd, and bis(triphenylphosphine)Pd dichloride.

80. The process according to embodiment 79, wherein the palladium-phosphine complex-based catalyst is tBuXPhos Pd.

81. A process for preparing a solid form of Compound 2

(Compound 2)

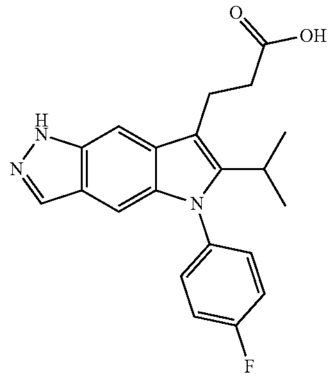

or a pharmaceutically acceptable salt thereof, comprising:

(a0) reacting

J0

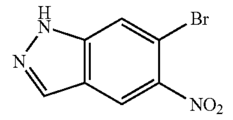

or a pharmaceutically acceptable salt thereof with 4-fluorophenylboronic acid to form

H184

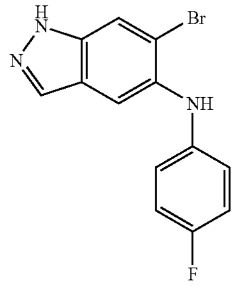

or a pharmaceutically acceptable salt thereof; and (a1) reacting H184 or a pharmaceutically acceptable salt thereof with trimethyl(3-methylbut-1-yn-1-yl) silane to form

T3

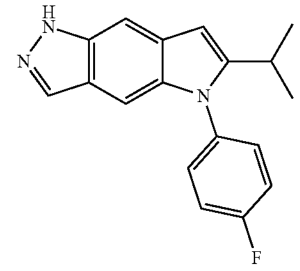

or a pharmaceutically acceptable salt thereof;

(a) reacting T3 or a pharmaceutically acceptable salt thereof with methyl 3,3-dimethoxypropanoate to form

I1

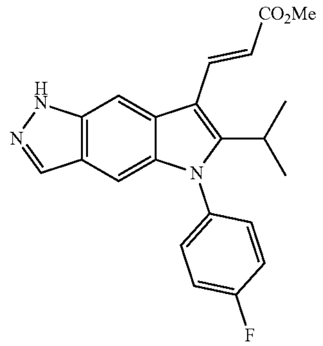

or a pharmaceutically acceptable salt thereof;

(b) reducing I1 or a pharmaceutically acceptable salt thereof to

H36

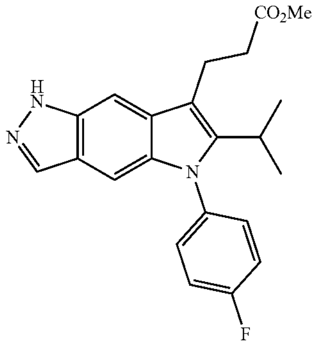

or a pharmaceutically acceptable salt thereof, and (c) de-esterifying H36 or a pharmaceutically acceptable salt thereof to yield the solid form of Compound 2 or a pharmaceutically acceptable salt thereof.

82. The process according to embodiment 81, wherein the process can be further defined with the reagents and conditions recited in any one of embodiments 2 to 80.

83. A process for preparing a solid form of Compound 2

(Compound 2)

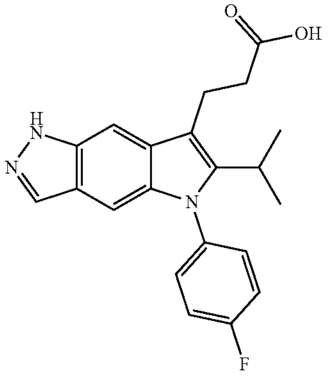

or a pharmaceutically acceptable salt thereof, comprising:

(a0) reacting

J0

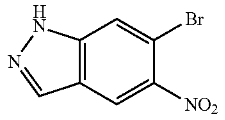

or a pharmaceutically acceptable salt thereof with pivaloyl chloride to form

J1

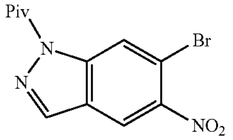

or a pharmaceutically acceptable salt thereof;

(a1) reacting J1 or a pharmaceutically acceptable salt thereof with 4-fluorophenylboronic acid to form

K1

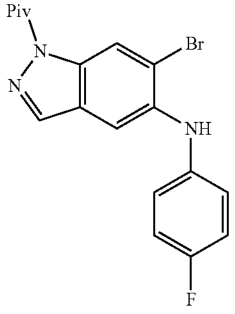

or a pharmaceutically acceptable salt thereof;

(a2) deprotecting K1 or a pharmaceutically acceptable salt thereof and adding trimethyl(3-methylbut-1-yn-1-yl)silane to form

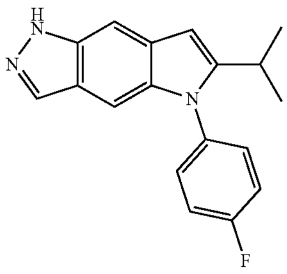

T3 or a pharmaceutically acceptable salt thereof, (a) reacting T3 or a pharmaceutically acceptable salt thereof with methyl 3,3-dimethoxypropanoate to form

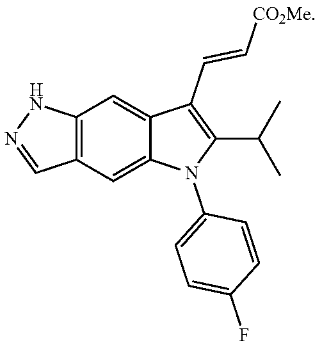

I1 or a pharmaceutically acceptable salt thereof;

(b) reducing I1 or a pharmaceutically acceptable salt thereof to

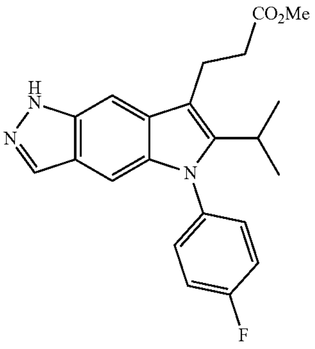

H36 or a pharmaceutically acceptable salt thereof, and (c) de-esterifying H36 or a pharmaceutically acceptable salt thereof to yield the solid form of Compound 2 or a pharmaceutically acceptable salt thereof.

84. The process according to embodiment 83, wherein the process can be further defined with the reagents and conditions recited in any one of embodiments 2 to 80.

85. A process for preparing a solid form of Compound 2

(Compound 2)

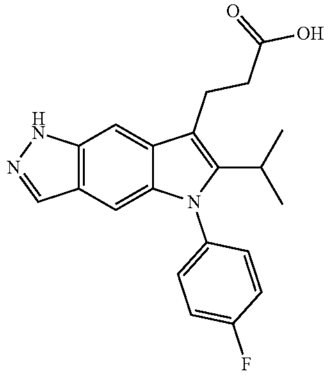

or a pharmaceutically acceptable salt thereof, comprising:

(a1')

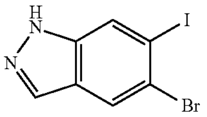

H7 or a pharmaceutically acceptable salt thereof with trimethyl (3-methylbut-1-yn-1-yl)silane to form

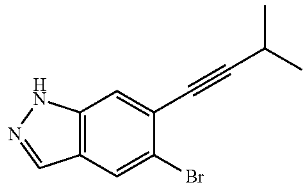

H8 or a pharmaceutically acceptable salt thereof, (a2') reacting H8 or a pharmaceutically acceptable salt thereof with 4-fluoroaniline to form

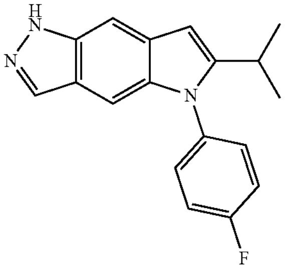

T3 or a pharmaceutically acceptable salt thereof;

(a) reacting T3 or a pharmaceutically acceptable salt thereof with methyl 3,3-dimethoxypropanoate to form

I1

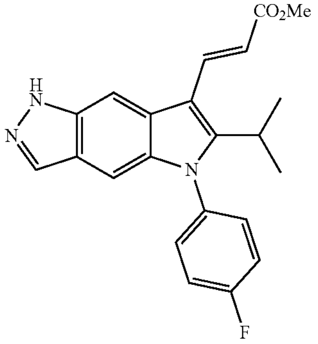

or a pharmaceutically acceptable salt thereof;

(b) reducing I1 or a pharmaceutically acceptable salt thereof to

H36

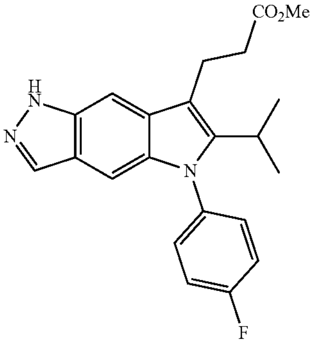

or a pharmaceutically acceptable salt thereof; and (c) de-esterifying H36 or a pharmaceutically acceptable salt thereof to yield the solid form of Compound 2 or a pharmaceutically acceptable salt thereof.

86. The process according to embodiment 85, wherein the process can be further defined with the reagents and conditions recited in any one of embodiments 2 to 80.

87. A compound

I1

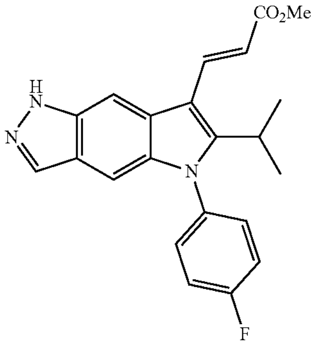

or a pharmaceutically acceptable salt thereof.

88. A process for preparing methyl (E)-3-(5-(4-fluorophenyl)-6-isopropyl-1,5-dihydropyrrolo[2,3-f]indazol-7-yl)acrylate (I1):

I1

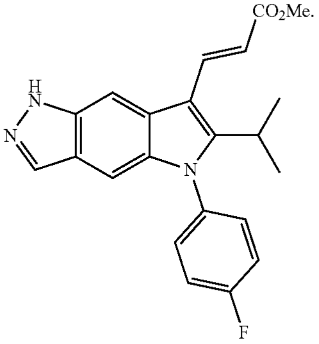

or a pharmaceutically acceptable salt thereof, comprising: reacting

T3

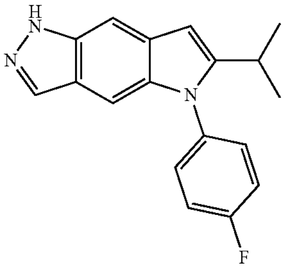

or a pharmaceutically acceptable salt thereof with methyl 3,3-dimethoxypropanoate to form

I1

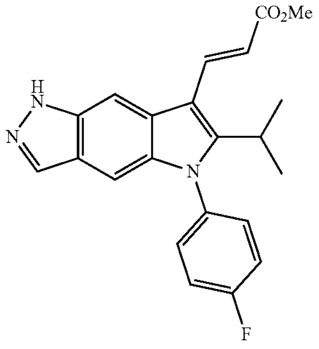

or a pharmaceutically acceptable salt thereof.

89. The process according to embodiment 88, comprising reacting T3 or a pharmaceutically acceptable salt thereof with methyl 3,3-dimethoxypropanoate in the presence of a sulfonic acid and a solvent or a solvent system selected from dichloromethane, trifluoromethylbenzene, 2-methyltetrahydrofuran, propan-2-one/cyclopentane mixture, ethyl acetate/ethanol mixture, and a combination thereof.

90. The process according to embodiment 89, wherein the solvent is dichloromethane.

91. The process according to embodiment 89 or embodiment 90, wherein the sulfonic acid is selected from p-toluenesulfonic acid, p-toluenesulfonic acid monohydrate, camphorsulfonic acid, triflic acid, and a combination thereof (e.g., selected from p-toluenesulfonic acid, camphorsulfonic acid, triflic acid, and a combination thereof; p-toluenesulfonic acid).

92. The process according to embodiment 91, wherein the sulfonic acid isp-toluenesulfonic acid monohydrate.

93. The process according to any one of embodiments 88 to 92, comprising reacting T3 or a pharmaceutically acceptable salt thereof with methyl 3,3-dimethoxypropanoate at about 40-50° C. and with agitation.

Example 1: Large-Scale Synthesis of Compound 1

Scheme 3C depicts a large-scale synthesis of Compound 1 that utilizes 1-(6-bromo-5-nitro-1H-indazol-1-yl)-2,2-dimethylpropan-1-one (A1) as the starting material. This process is expected to yield a solid form of Compound 1 or a pharmaceutically acceptable salt thereof at an amount of at least about 100 kg. Scheme 3A depicts the preparation of the starting material A1. Scheme 3B depicts the preparation of D1 that is reacted with B1 at Step 2 of Scheme 3C to form C58B. Scheme 3B' depicts an alternative preparation process for D1.

Preparation of 1-(6-bromo-5-nitro-1H-indazol-1-yl)-2,2-dimethylpropan-1-one (A1)

Scheme 3A

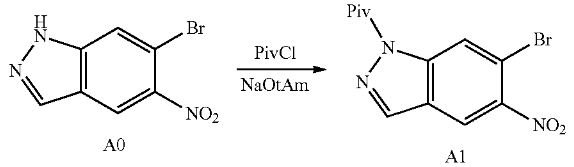

A0 A1

To A0 (3.1 kg, 11.9 mol), which is commercially available, in THF (35 L) at −26° C., sodium tert-amylate (33.4 wt % in THF, 4.55 kg, 13.8 mol) was added over 15 minutes, and the mixture was rinsed with THE (300 mL). The mixture was re-cooled to −26° C. over 15 minutes and then pivaloyl chloride (Piv-C1) (1.75 kg, 14.5 mol) was added over 4 minutes. The mixture was rinsed with THE (300 mL). The mixture was warmed to 15° C. over 55 minutes and held for 30 minutes. A solution of sodium bicarbonate (150 g) in water (2 L) was added, followed by additional water (9 L). The resulting biphasic slurry was concentrated under vacuum to ~25-L volume, then diluted with methanol (11.2 L). The slurry was heated to 40° C. for 30 minutes, diluted with water (11.3 L) over 30 minutes, and then cooled to room temperature. A second run from 3.1 kg A0 was similarly performed. The two slurries were combined, filtered, and washed with 1:1 methanol:water (20 L). The solids were dried with heated nitrogen to afford A1 (7.69 kg, 23.6 mol, 99%) as a tan solid.

Alternatively, to A0 (43.0 kg, 1.0 eq.) which is commercially available, in THF (382.7 kg) at −5-5° C., potassium tert-butoxide (23.9 kg) was added over 2 hours. Then pivaloyl chloride (Piv-C1) (25.7 kg) was added at −5-5° C. over 2 hours. The mixture was stirred for 1 hour at −5-5° C. Water (215 kg) was added at 0-10° C. over one hour, and the mixture stirred for an additional hour. The solids were filtered, and the filter cake was rinsed with THE (38.3 kg). The wet product was slurried in THF (76.5 kg) and water (301.0 kg) at 50-60° C. and stirred for 1-2 hours. The mixture was cooled to 10-20° C. and stirred for an additional 2-4 hours. The solid was filtered and the wet cake rinsed with THE (38.3 kg). The wet cake was dried with heated nitrogen to afford A1 as a tan solid (46 kg, 79.45% yield). $^1$H NMR (400 MHz, DMSO) δ 8.63 (d, J=0.4 Hz, 1H), 8.36 (d, J=1.0 Hz, 1H), 8.07 (dd, J=1.1, 0.4 Hz, 1H).

Preparation of methyl 4-(2-oxo-2-(tetrahydro-2H-pyran-4-yl)ethyl)benzoate (D1)

Scheme 3B

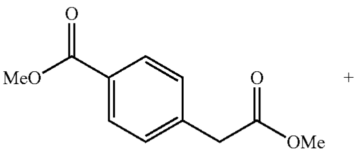

F1

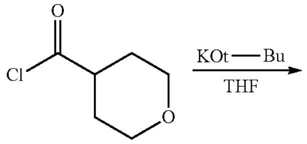

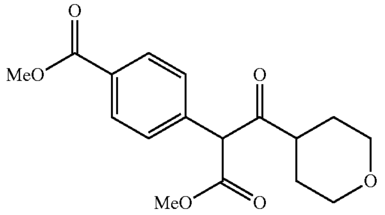

E1

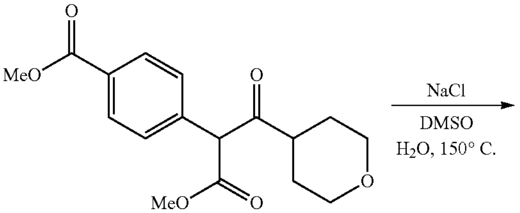

E1

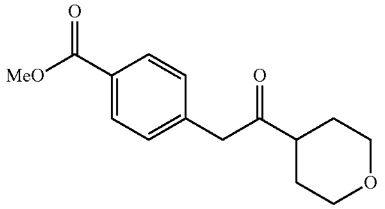

D1

The reactor was charged with methyl 4-(2-methoxy-2-oxoethyl)benzoate (F1) (500 mg, 2.401 mmol, 1 equiv.), which is commercially available, and tetrahydrofuran (4.0 mL, 8 vol.), followed by potassium tert-butoxide (2.8 mL, 1.0 M, 1.2 equiv.) at ambient temperature. The resulting slurry was transferred to a solution of oxane-4-carbonyl chloride (0.59 mL, 2 equiv.) and tetrahydrofuran (1.0 mL, 1 vol.). The reaction was quenched with saturated aqueous ammonium chloride (5.0 mL, 10 vol.) and extract three times with ethyl acetate (5.0 mL, 10 vol.). The combined organics were washed with 50% saturated aqueous sodium chloride (10.0 mL, 20 vol.), then dried with sodium sulfate, filtered, and concentrated in vacuo to afford methyl 4-(1-methoxy-1,3-dioxo-3-(tetrahydro-2H-pyran-4-yl)propan-2-yl)benzoate (E1).

$^1H$ NMR (400 MHz, $CDCl_3$) δ 8.03 (d, J=8.4 Hz, 2H), 7.42 (d, J=8.4 Hz, 2H), 4.95 (s, 1H), 3.92 (s, 3H), 3.75 (s, 3H), 3.40-3.27 (m, 2H), 3.14 (td, J=12.1, 2.0 Hz, 2H), 2.69 (tt, J=11.1, 4.1 Hz, 1H), 2.02-1.90 (m, 2H), 1.48-1.39 (m, 2H).

Next, the reactor was charged with methyl 4-(1-methoxy-1,3-dioxo-3-(tetrahydro-2H-pyran-4-yl)propan-2-yl)benzoate (E1) (489 mg, 1.528 mmol, 1 equiv.), dimethyl sulfoxide (4.9 mL, 10 vol.), and aqueous sodium chloride (0.68 mL, 4.5 M, 2.0 equiv.). The reaction mixture was heated to 150° C. for 3 hours, then cooled to room temperature. The reaction mixture was diluted with $H_2O$ (4.9 mL, 10 vol.) and extracted three times with ethyl acetate (4.9 mL, 10 vol.). The combined organics were dried with sodium sulfate, filtered, and concentrated in vacuo to afford methyl 4-(2-oxo-2-(tetrahydro-2H-pyran-4-yl)ethyl)benzoate (D1).

$^1H$ NMR (400 MHz, $CDCl_3$) δ 8.00 (d, J=8.3 Hz, 2H), 7.26 (d, J=8.4 Hz, 2H), 3.99 (dt, J=11.5, 3.5 Hz, 2H), 3.91 (s, 3H), 3.81 (s, 2H), 3.45-3.35 (m, 2H), 2.73-2.61 (m, 1H), 1.79-1.68 (m, 4H).

Alternative preparation of methyl 4-(2-oxo-2-(tetrahydro-2H-pyran-4-yl)ethyl)benzoate (D1)

Scheme 3B′

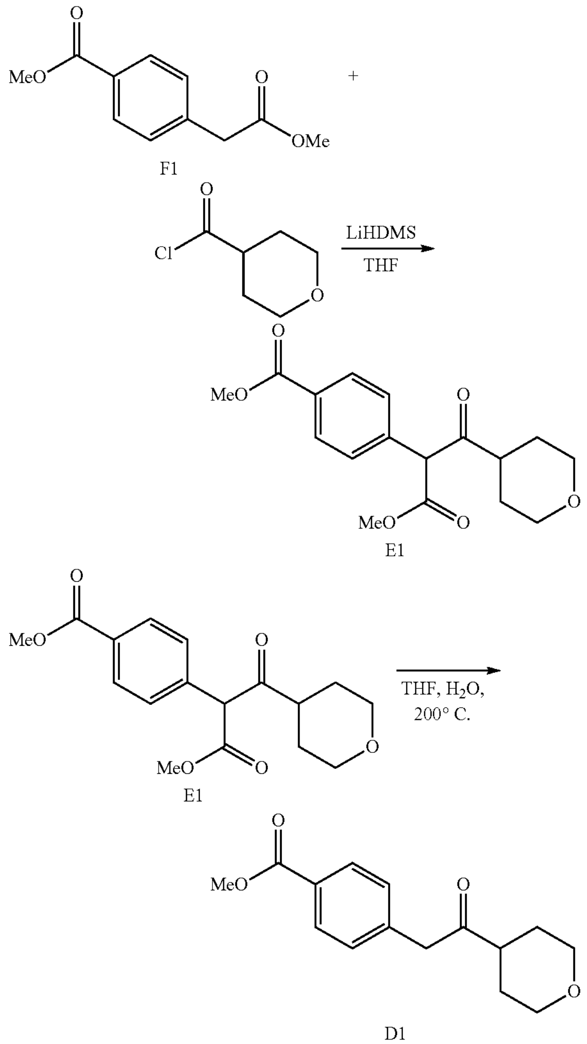

F1

E1

E1

D1

To a solution of methyl 4-(2-methoxy-2-oxoethyl)benzoate (F1) (5.0 g, 24.01 mmol) in THF (10.0 mL) at 0° C. was added LiHMDS (48.0 mL, 1.0 M, 48.03 mmol). A solution of oxane-4-carbonyl chloride (5.9 mL, 48.03 mmol) in THF (30.0 mL) was prepared in a separate vessel. Both solutions were simultaneously added over 2 hours to an empty reactor at 0° C. Upon complete addition of both reagent solutions, the mixture was diluted with water (50 mL) and HCl (2.0 M) to pH 4 at 0° C., then extracted three times with MTBE (50 mL). The combined organic phases were washed twice with HCl (1.0 M, 50 mL), then twice with water (50 mL), dried with $Na_2SO_4$, filtered, and concentrated in vacuo to afford methyl 4-(1-methoxy-1,3-dioxo-3-(tetrahydro-2H-pyran-4-yl)propan-2-yl)benzoate (E1).

$^1H$ NMR (400 MHz, $CDCl_3$) δ 8.03 (d, J=8.4 Hz, 2H), 7.42 (d, J=8.4 Hz, 2H), 4.95 (s, 1H), 3.92 (s, 3H), 3.75 (s, 3H), 3.40-3.27 (m, 2H), 3.14 (td, J=12.1, 2.0 Hz, 2H), 2.69 (tt, J=11.1, 4.1 Hz, 1H), 2.02-1.90 (m, 2H), 1.48-1.39 (m, 2H).

A solution of methyl 4-(1-methoxy-1,3-dioxo-3-(tetrahydro-2H-pyran-4-yl)propan-2-yl)benzoate (400 mg, 1.25 mmol) in THF (2.8 mL) and water (1.75 mL) was sealed and heated to 200° C. in a microwave reactor for 10 minutes. The mixture was then cooled to room temperature, diluted with water (4.0 mL), and extracted three times with EtOAc (4.0 mL). The combined organics were dried with $Na_2SO_4$, filtered, and concentrated in vacuo to afford methyl 4-(2-oxo-2-(tetrahydro-2H-pyran-4-yl)ethyl)benzoate (D1).

$^1H$ NMR (400 MHz, $CDCl_3$) δ 8.00 (d, J=8.3 Hz, 2H), 7.26 (d, J=8.4 Hz, 2H), 3.99 (dt, J=11.5, 3.5 Hz, 2H), 3.91 (s, 3H), 3.81 (s, 2H), 3.45-3.35 (m, 2H), 2.73-2.61 (m, 1H), 1.79-1.68 (m, 4H).

Alternative Telescoped Preparation of methyl 4-(2-oxo-2-(tetrahydro-2H-pyran-4-yl)ethyl)benzoate (D1)

A solution of oxane-4-carbonyl chloride (1249.3 g, 8.4 mol) in THF (4690.0 mL) was slowly added to a solution of methyl 4-(2-methoxy-2-oxoethyl)benzoate (F1) (1167.0 g, 5.6 mol) in THF (5600.0 mL) at 5° C. The reaction mixture and LiHMDS (11.2 L, 1.0 M in THF) were injected using two injector pumps, mixed in a T-shaped mixer, and then flowed into a coiled reactor cooled to 10° C. The reaction was outflowed into HCl (5250.0 mL, 4.5 M) and cooled to 15° C. The organic phase was separated and then flowed into a coiled reactor heated to 180° C. The outflow mixture was cooled to 20° C., then concentrated in vacuo. The concentrate was diluted with water (1750.0 mL), then concentrated. The resulting concentrate was diluted with MeOH (1750.0 mL) and stirred at 20° C. for 1 hour. The mixture was filtered, and the filter cake was resuspended in MeOH (3500.0 mL) and stirred at 20° C. for 1 hour. The mixture was filtered. The wet cake was washed with MeOH (2335.0 mL), then dried at 45° C. to afford methyl 4-(2-oxo-2-(tetrahydro-2H-pyran-4-yl)ethyl)benzoate (D1) (1167.0 g, 86%).

$^1H$ NMR (400 MHz, $CDCl_3$) δ 8.00 (d, J=8.3 Hz, 2H), 7.26 (d, J=8.4 Hz, 2H), 3.99 (dt, J=11.5, 3.5 Hz, 2H), 3.91 (s, 3H), 3.81 (s, 2H), 3.45-3.35 (m, 2H), 2.73-2.61 (m, 1H), 1.79-1.68 (m, 4H).

Example 2: Alternative Preparation of Compound 1 and Intermediate C13

The intermediate 1-(6-bromo-5-((4-fluorophenyl)amino)-1H-indazol-1-yl)-2,2-dimethylpropan-1-one (B1) described in Example 1 may be used as a starting material to prepare C13. As depicted in Schemes 1B-1C, C13 is a key intermediate in the synthesis of Compound 1. Accordingly, the present disclosure provides alternative preparations of Compound 1 and C13, where H184 is used as the starting material, as depicted in Scheme 4 below and described as follows:

Scheme 4

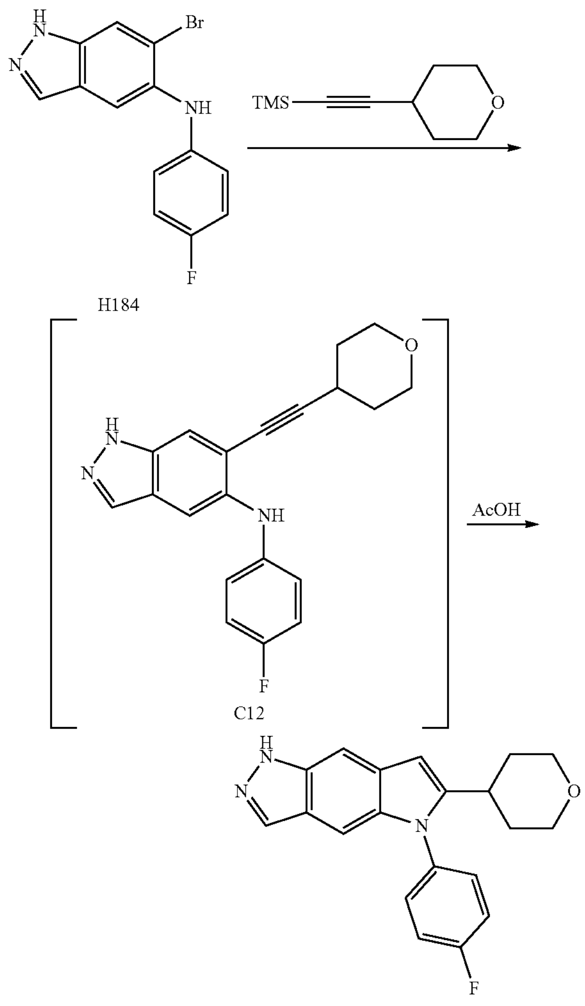

H184

C12

C13

The reactor was charged with 6-bromo-N-(4-fluorophenyl)-1H-indazol-5-amine (6.3 g, 20.579 mmol, 1 equiv.), copper iodide 99.9% (0.274 g, 1.441 mmol, 0.07 equiv.) and bis(triphenylphosphine)palladium(II) dichloride (0.144 g, 0.206 mmol, 0.01 equiv.). The reaction mixture was charged with 2-propanol (50.4 mL, 0.408 M, 8 vol.) and stirring was initiated. The system was evacuated and purged with nitrogen three times. Potassium hydroxide (2.887 g, 7.216 mL, 40 w/v %, 51.448 mmol, 2.5 equiv.) was added, followed by trimethyl((tetrahydro-2H-pyran-4-yl)ethynyl)silane (4.878 g, 26.753 mmol, 1.3 equiv.). The system was evacuated and purged with nitrogen three times. The reaction was heated to 75-80° C. Upon reaction completion, the mixture was charged with acetic acid (5.87 g, 5.596 mL, 1.049 g/mL, 97.752 mmol, 4.75 equiv.) and stirring was continued at 75-80° C. Upon reaction completion as assessed by HPLC, the mixture was cooled down to 50° C. and water (50.4 mL, 0.408 M, 8 vol.) was slowly added. The reaction was cooled to 23° C. The solids were collected by filtration, and the wet cake was washed with water. The material was dried under vacuum at 55° C. 5-(4-fluorophenyl)-6-(tetrahydro-2H-pyran-4-yl)-1,5-dihydropyrrolo[2,3-f]indazole was isolated in 94% yield.

Non-limiting examples of alternative reagents and solvents that can be used in the conversion of B1 to $C_{13}$ are:

Solvents: Other alcohol solvents such as 1-butanol, ethanol, and the like;

Base: NaOH.

Subsequent reaction steps for preparing Compound 1 are depicted in Schemes 1B and 1C and are also described in International Patent Application No. PCT/US2020/032832, published as International Patent Application Publication No. WO 2020/247160.

Example 3: Alternative Preparation of Compound 1

Scheme 5 depicts an alternative large-scale synthesis of Compound 1 that utilizes 1-(6-bromo-5-nitro-1H-indazol-1-yl)-2,2-dimethylpropan-1-one (A1) as the starting material.

Scheme 5

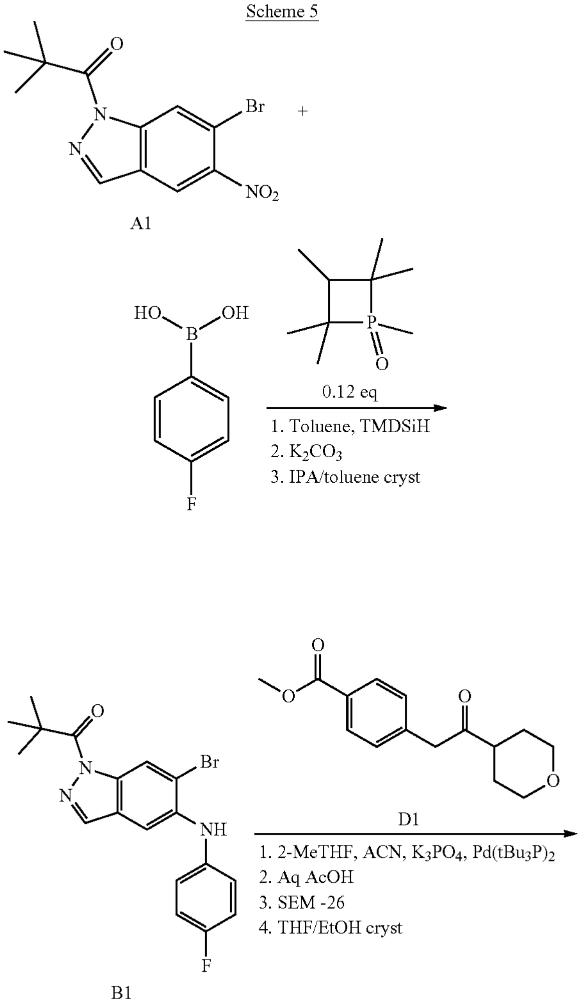

A1

D1

B1

-continued

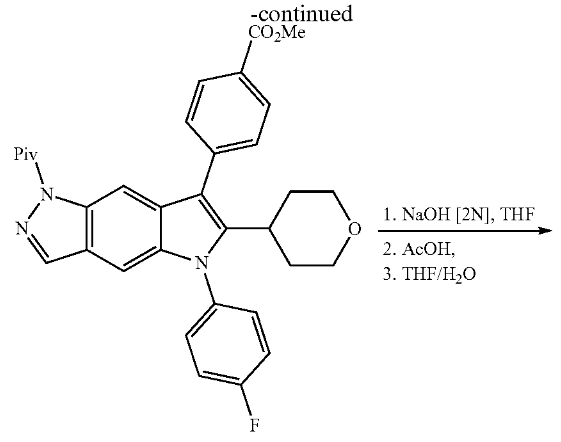

C58B

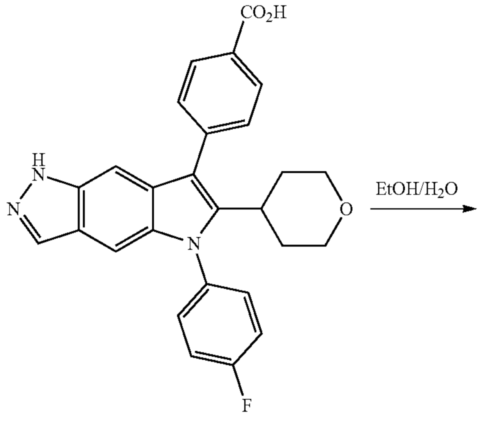

Compound 1 THF solvate

Compound 1 Form A

Step 1: Synthesis of 1-(6-bromo-5-((4-fluorophenyl) amino)-1H-indazol-1-yl)-2,2-dimethylpropan-1-one (B1)

1-(6-bromo-5-nitro-1H-indazol-1-yl)-2,2-dimethylpropan-1-one (A1) (0.4 kg, 1.206 mol, 1.0 equiv., limiting reagent) and 4-fluorophenylboronic acid (0.186 kg, 1.326 mol, 1.1 equiv.) were charged to the reactor. 1,2,2,3,4,4-hexamethylphosphetane 1-oxide (0.026 kg, 0.151 mol, 0.125 equiv.) was added to the reactor, followed by toluene (4000 L, 10 vols.). The reaction mixture was agitated. 1,1,3,3-tetramethyldisiloxane (0.324 kg, 0.426 L, 2.411 mol, 2.0 equiv.) was charged to the reactor, and the reaction mixture was heated to 100° C. When the reaction reached completion as assessed by HPLC, the reactor was cooled to 25° C. and charged with IPA (7 vols., 2.8 L). The solution was filtered over a pad of Celite (0.110 kg), the reactor was rinsed with IPA (3 vol., 1.2 L), and the rinse was dropped on the Celite cake. The filtrate was heated to 35° C., then the reactor was charged with aqueous potassium carbonate solution (1.0 M, 2.4 L, 6 vols.). The mixture was stirred for 30 minutes. Stirring was then stopped and the phases were allowed to settle for 30 minutes. The bottom aqueous phase was drained. The top organic phase was distilled under vacuum to 8 volumes. The reactor was charged with IPA (4 L, 10 vols.) and was distilled again to 8 volumes. IPA (1.6 L, 4 vols.) was charged to the reactor (12 vols. total). The reactor was heated to 78° C. internal temperature and stirred at 78° C. for not less than 1 hour. The reaction mixture was cooled to 0° C. over 6 hours, then the reaction mixture was stirred at 0° C. for 1 hour before filtration. The wet cake was rinsed with IPA (0.8 L, 2 vols.) and dried in a vacuum oven at 45° C. with a nitrogen bleed. The product 1-(6-bromo-5-((4-fluorophenyl)amino)-1H-indazol-1-yl)-2,2-dimethyl-propan-1-one (B1) was an off-white to beige solid (about 75% yield). $^1H$ NMR (400 MHz, Chloroform-d) δ 8.76 (d, J=0.9 Hz, 1H), 7.87 (d, J=0.9 Hz, 1H), 7.24 (d, J=5.9 Hz, 2H), 7.18-6.97 (m, 4H), 5.97 (s, 1H), 1.54 (s, 9H), 1.43 (d, J=0.8 Hz, 1H).

Non-limiting examples of alternative reagents and solvents that can be used in the conversion of A1 to B1 are:

Solvents: CPME, IPAc, THF;

Reducing agent: Phenylsilane, polymethylsilane, $PPh_3$; $PPh_3O$;

Catalyst: $(MoO_2Cl_2)DMF_2$ with $PPh_3$ or a silane; 4-methyl-1-phenyl-2,3-dihydrophosphole 1-oxide 4, (2R,5R)-1-{2-[(2R,5R)-2,5-diethylphospholan-1-yl] phenyl}-2,5-diethyl-1-phospholan-1-one, 1-(adamantan-1-ylphosphoroso)adamantane.

Step 2: Synthesis of methyl 4-(5-(4-fluorophenyl)-1-pivaloyl-6-(tetrahydro-2H-pyran-4-yl)-1,5-dihydropyrrolo[2,3-f]indazol-7-yl)benzoate (C58B)

A solution of 2-MeTHF (100 mL, 10 vol.) and ACN (10 mL, 1 vol.) was degassed and sparged with nitrogen 3 times. 1-(6-bromo-5-((4-fluorophenyl)amino)-1H-indazol-1-yl)-2,2-dimethylpropan-1-one (B1) (10 g, 25.63 mmol, 1 equiv., limiting reagent) was added to the reactor. Methyl 4-(2-oxo-2-(tetrahydro-2H-pyran-4-yl)ethyl)benzoate (7.4 g, 28.19 mmol, 1.1 equiv.) was added to the reactor, followed by anhydrous $K_3PO_4$ (6.53 g, 30.750 mmol, 1.2 equiv.). 2-MeTHF/ACN solvent was added to the reactor, and the reaction mixture was agitated. The solution was degassed and sparged with nitrogen 3 times. Bis(tri-tert-butyl-phosphine)palladium(0) (9.82 g, 19.22 mmol, 0.075 equiv.) was added to the reactor at 20-25° C. The solution was degassed and sparged with nitrogen 3 times. The reaction mixture was heated to 50-55° C. Once the reaction reached completion as assessed by HPLC, the reactor was cooled to 20° C. and charged with acetic acid (4.63 g, 4.4 mL, 77.1 mmol, 3 equiv.) at 20-25° C. Water (500 mL, 5 vol.) was charged to the reactor, followed by 2-MeTHF (150 mL, 15 vol.). The mixture was stirred for 30 minutes, and then the phases were allowed to separate. The bottom aqueous layer was removed and water was added (500 mL, 5 vol.). The mixture was stirred for 15 minutes and the phases were allowed to separate. The bottom aqueous layer was removed and set aside. The organic solution was distilled under reduced pressure, and 2-MeTHF was added to obtain a volume of 25. SEM 26 (20 wt %, 2 g) was charged to the reactor, which was heated to an internal temperature of 40-45° C. The reaction mixture was stirred for 12 hours and then filtered. The reactor was washed with 2-MeTHF (20 mL, 2 vol.) and the rinse dropped onto the filter. The filtrate was distilled and solvent swapped into THF. THE was added to top up to 8-9 volumes in the reactor. The reactor contents were heated to 60-65° C. to obtain a solution. The reactor was cooled to 50° C. over 1 hour, and the contents stirred at 50° C. for 30 minutes. EtOH (180 mL, 18 vol.) was charged over 3 hours. The reactor was cooled to an internal temperature of 10° C. over 8 hours. The slurry was stirred for not less than 1 hour at 10° C. The mixture was filtered. The reactor was rinsed twice with EtOH (20 ml, 2 vol.) and the rinse dropped onto the wet cake. The wet cake was dried in a vacuum oven set to 65° C. and dried for 16 hours. The product methyl 4-(5-(4-fluorophenyl)-1-pivaloyl-6-(tetrahydro-2H-pyran-4-yl)-1,5-dihydropyrrolo[2,3-f]indazol-7-yl)benzoate (C58B) was isolated as an off-white solid (about 68% yield).

Non-limiting examples of alternative reagents and solvents that can be used in the conversion of B1 to C58B are:

Solvents: MeTHF, THF, toluene, CPME, DMF, ACN, propionitrile, THF/ACN; MeTHF/ACN, THF/propionitrile; MeTHF/propionitrile;

Base: $K_2HPO_4$, $K_2H_2PO_4$, $K_2CO_3$, $Cs_2CO_3$;

Pd ligand: XPhos, Brett Phos; 2-(di-tert-butylphosphino)-1-(2-methoxyphenyl)-1H-pyrrole; catacXium.

Step 3A: Synthesis of Compound 1 Form A

Methyl 4-(5-(4-fluorophenyl)-1-pivaloyl-6-(tetrahydro-2H-pyran-4-yl)-1,5-dihydropyrrolo[2,3-f]indazol-7-yl)benzoate (25.1 g, 45.337 mmol, 1 equiv., limiting reagent) (C58B) and THF (326.3 mL, 13 vol.) were added to the reactor. Sodium hydroxide [2N](5.44 g, 68.0 mL, 136.01 mmol, 3 equiv.) was added to the reactor, which was heated to 58° C. Upon reaction completion as assessed by HPLC, the reactor was cooled to 20° C. Water (75.3 mL, 3 vol.), acetic acid (10.89 g, 10.38 mL, 181.35 mmol, 4 equiv.) and 2-MeTHF (251 mL, 10 vol.) were charged to the reactor and stirred for not less than 30 minutes. Stirring was stopped and the layers allowed to separate. Water (75.3 mL, 3 vol.) was added to the organic layer and extracted. The layers were allowed to separate, and an aqueous 6.5 wt % sodium chloride solution (NaCl 8.2 g, 0.14 mmol, 3.1 equiv.) in water (0.120 L, 4.7 vol.) was added to the organic layer. The reaction mixture was stirred for not less than 30 minutes, then agitation was stopped, and the layers were allowed to separate. The organic layer was distilled down to 2-3 volumes. EtOH (0.176 mL, 7 vol.) was added to the reactor and distillation continued. EtOH (0.150 L, 6 vol.) and water (25.1 mL, 1 vol.) were added, and the slurry was distilled down to 2-3 volumes. EtOH (0.150 L, 6 vol.) and water (25.1 mL, 1 vol.) were added to the reactor and distillation continued down to 3 volumes. EtOH (0.150 L, 6 vol.) and water (25.1 mL, 1 vol.) were added to the reactor, and the reaction mixture was stirred for not less than 30 minutes at 40° C. The reactor was cooled down to 20-25° C. at a 5° C./h rate. The reactor contents were stirred for at least 30 minutes at 20° C. The slurry was filtered and the resulting wet cake rinsed with a EtOH/$H_2O$ 1:1 mixture (50 mL, 2 vol.). The wet cake was dried in a vacuum oven set to 66° C. for not less than 12 hours. The product 4-(5-(4-fluorophenyl)-6-(tetrahydro-2H-pyran-4-yl)-1,5-dihydropyrrolo[2,3-f]indazol-7-yl)benzoic acid (Compound 1 Form A) was isolated in 90% yield.

Non-limiting examples of alternative reagents and solvents that can be used in the conversion of C58B to Compound 1 described above are as follows:

Solvents: MeTHF, EtOH, MeOH, IPA;

Base: LiOH, NaOH, KOH;

Work up: acetic acid, HCl.

Step 3B: Alternative Synthesis of Compound 1 Form A

To obtain Compound 1 Form A, methyl 4-(5-(4-fluorophenyl)-1-pivaloyl-6-(tetrahydro-2H-pyran-4-yl)-1,5-dihydropyrrolo[2,3-f]indazol-7-yl)benzoate (25.1 g, 45.337 mmol, 1 equiv., limiting reagent) and THE (326.3 mL, 13 vol.) were added to the reactor. Sodium hydroxide [2N](5.44 g, 68.0 mL, 136.01 mmol, 3 equiv.) was added to the reactor, which was heated to 58° C. Upon reaction completion as assessed by HPLC, the reactor was cooled to 20° C. Water (3.00 vol., 75.3 mL) was added to the reactor at 20° C. and stirred for 15 minutes. Acetic acid (10.89 g, 10.38 mL, 181.35 mmol, 4 equiv.) was added to the reactor at 20-25° C., and the reaction mixture was stirred for 30 minutes. The phases were allowed to settle for 30 minutes and then the bottom aqueous layer was drained. Water (20 vol., 502 mL) was added to the reactor over 5 hours at 20° C. The resulting slurry was aged for 2 hours, filtered, and washed with a mixture of water (2.5 vol., 125.5 L) and tetrahydrofuran (1.5 vol., 37.7 mL). The wet cake was dried at 65° C. for not less than 16 hours. Compound 1 as a THF solvate was isolated as an off-white to yellow solid (about 88% yield).

A solution of water (1.5 vol., 37.7 mL) and ethanol (8.5 vol, 231.4 mL) was prepared. Compound 1 THF solvate was charged to the reactor, and the reaction mixture was stirred to suspend solids. The resulting slurry was aged for 4 hours at 20-25° C. and filtered. The wet cake was washed with a solution of water (0.6 vol., 15.1 mL) and ethanol (3.4 vol., 85.3 mL). The wet cake was dried at greater than 65° C. to obtain Compound 1 Form A (about 87% yield).

Example 4: Alternative Preparation of Intermediate C58B

Scheme 6 depicts an alternative process for preparing the intermediate C58B.

Scheme 6

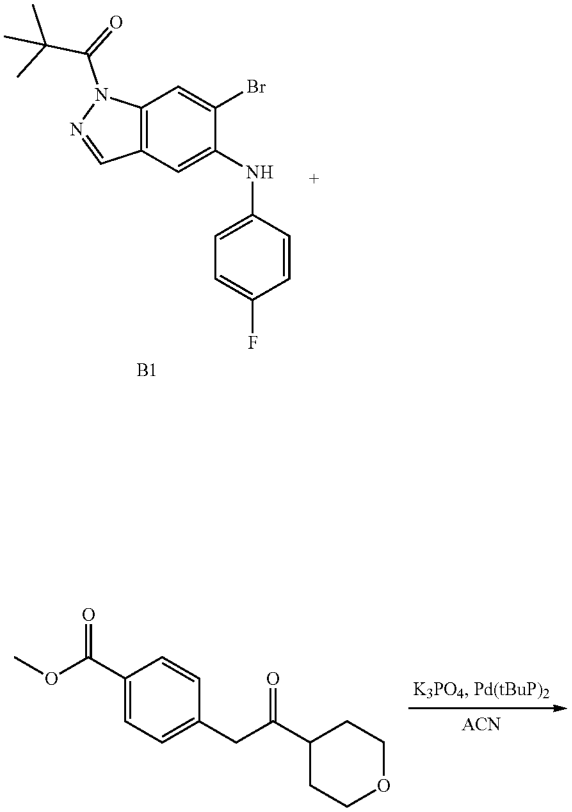

B1

D1

-continued

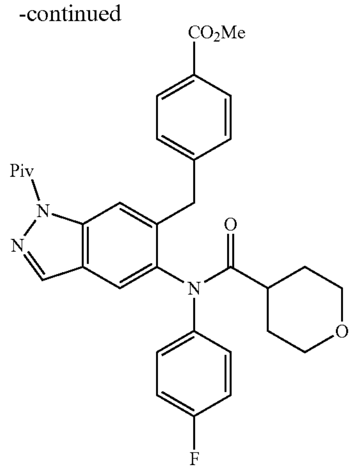

GI

LiHMDS
THF

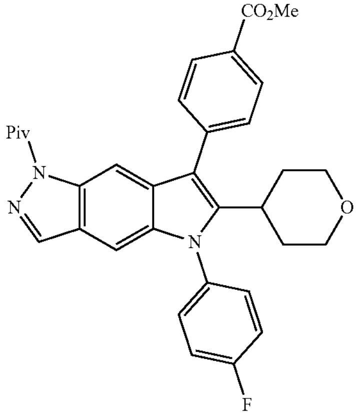

C58B

Step 1: Synthesis of methyl 4-((5-(N-(4-fluorophenyl)tetrahydro-2H-pyran-4-carboxamido)-1-pivaloyl-1H-indazol-6-yl)methyl)benzoate (G1)

A solution of acetonitrile (101 mL, 10 vol.) was degassed and sparged with nitrogen 3 times. 1-(6-bromo-5-((4-fluorophenyl)amino)-1H-indazol-1-yl)-2,2-dimethylpropan-1-one (B1) (10.1 g, 25.86 mmol, 1 equiv., limiting reagent) was added to the vessel. Methyl 4-(2-oxo-2-(tetrahydro-2H-pyran-4-yl)ethyl)benzoate (D1) (7.46 g, 28.441 mmol, 1.1 equiv.) was added to the vessel, followed by anhydrous $K_3PO_4$ (7.14 g, 33.61 mmol, 1.3 equiv.). Agitation commenced. The solution was degassed and sparged with nitrogen 3 times. Bis(tri-tert-butyl-phosphine)palladium(0) (991 mg, 1.94 mmol, 0.075 equiv.) was added to the reactor at 20-25° C. The solution was degassed and sparged with nitrogen 3 times. The reaction mixture was heated to 80-85° C. Once the reaction reached completion as assessed by HPLC, the reaction mixture was cooled to 20° C. and acetic acid was charged to obtain a pH of 4 at 20-25° C. Water was added (40.4 mL, 4 vol.). MtBE (8.75 mL, 5 vol.) was added, and the reaction mixture was stirred for 30 minutes. Agitation was stopped, and the phases were allowed to separate. The bottom aqueous layer was removed and water added (8.75 mL, 5 vol.). The reaction mixture was stirred for 15 minutes, then agitation was stopped and the phases were allowed to separate. The bottom aqueous layer was removed and set aside. The organic solution was distilled under reduced pressure. The isolated material was dissolved in THF and 40 wt % SEM26 was added. The reaction mixture was stirred for 16 hours at 40° C. and the reactor contents were filtered. The reactor was washed with THE (20 mL, 2 vol.), and the rinse was dropped onto the filter. The filtrate was distilled and THE was added. Heptane (20 mL, 2 vol.) was added, and the reaction mixture stirred. The precipitated solid was filtered. The filtrate was distilled and ethanol added (100 mL, 10 vol.). The reaction mixture was heated to 50° C. to obtain a solution, which was cooled to 20-25° C. and stirred. The solid was collected and washed with ethanol. The isolated cake was dried at >65° C. The product methyl 4-((5-(N-(4-fluorophenyl)tetrahydro-2H-pyran-4-carboxamido)-1-pivaloyl-1H-indazol-6-yl)methyl)benzoate (G1) was isolated as an off-white solid (39.8% yield for first crop).

$^1$H NMR (400 MHz, DMSO $d_6$) δ 8.54 (s,1H), 8.19 (s,1H), 8.32 (s,1H), 7.9 (m, 3H), 7.25 (m, 2H), 7.16 (m, 3H), 4.04 (m, 2H), 3.85 (s, 2H), 3.65 (m, 2H), 3.03 (m, 4H), 2.15 (m, 1H), 1.68 (m, 4H), 1.47 (m. 9H)

$^{13}$C NMR (400 MHz, DMSO $d_6$) δ 177.84, 174.88, 166.54, 162.31, 145.11, 140.02, 139.79, 138.09, 137.47, 131.12, 130.29, 130.13, 131.12, 123.8, 125.13, 121.79, 118.90, 117.26, 66.3, 52.53, 41.86, 40.19, 37.46, 29.44, 27.80

MS (Compound+H) 572.2533

Step 2: Synthesis of C58B

To a solution of methyl 4-{[1-(2,2-dimethylpropanoyl)-5-[N-(4-fluorophenyl)oxane-4-amido]indazol-6-yl]methyl}benzoate (G1) (286 mg, 0.50 mmol) in THF (2.9 mL) at −35° C. was added LiHMDS (1.0 mL, 1.0 M, 1.00 mmol).

Example 5: Large-Scale Synthesis of Compound 2-1-(6-bromo-5-nitro-1H-indazol-1-yl)-2,2-dimethylpropan-1-one as Starting Material Scheme 7 depicts a large-scale synthesis of Compound 2 that utilizes 1-(6-bromo-5-nitro-1H-indazol-1-yl)-2,2-dimethylpropan-1-one as the starting material. This process is expected to yield a solid form of Compound 2 or a pharmaceutically acceptable salt thereof at an amount of at least about 100 kg.

Scheme 7

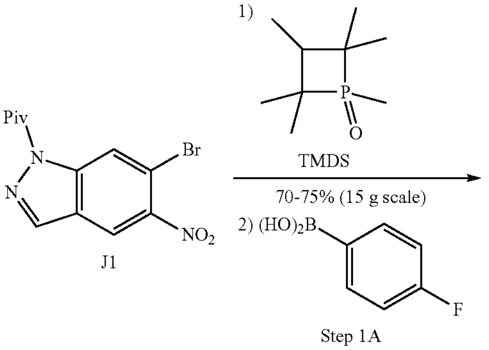

J1

Step 1A

-continued

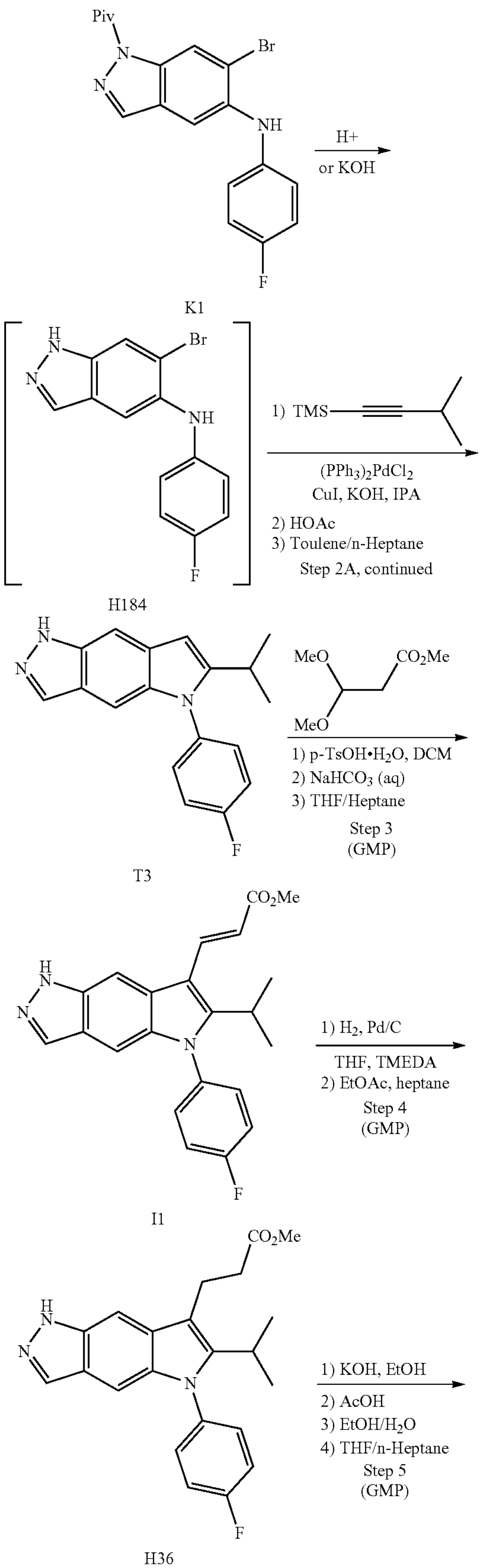

K1

H184

T3

I1

H36

-continued

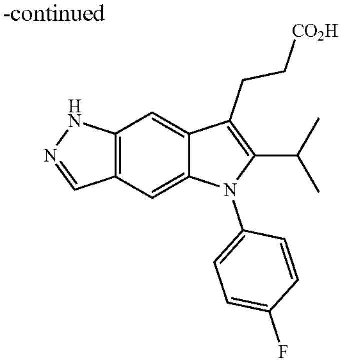

Compound 2

Step 1A: Synthesis of 1-(6-bromo-5-((4-fluorophenyl)amino)-1H-indazol-1-yl)-2,2-dimethylpropan-1-one (K1, also referred to as B1 herein)

The starting material J1 (also referred to as A1 herein; 1-(6-bromo-5-nitro-1H-indazol-1-yl)-2,2-dimethylpropan-1-one, 15.3 g, 46.911 mmol, 1 equiv.) was added into the reactor, followed by 4-fluorophenylboronic acid (8.533 g, 60.984 mmol, 1.3 equiv.) and hexamethyloxophosphetane (1.127 g, 7.037 mmol, 0.15 equiv.) as a catalyst, and toluene (153 mL, 0.307 M, 10 vol.). Dimethylsilyloxy(dimethyl) silane (TMDS) (18.904 g, 24.873 mL, 0.76 g/mL, 140.733 mmol, 3 equiv.) was added to the reactor at 18.5° C. The reaction was heated to 90° C. internal temperature. Once complete conversion was obtained (>97% conversion, around 7 hours), the internal temperature was set to 20° C. Half saturated sodium bicarbonate or $NaHCO_3$ (76.5 mL, 0.613 M, 5 vol.) was added to the reactor at 20-25° C. THF (2 vol., 30 mL) was added to the reactor, and the mixture was stirred for 15 minutes. The stirring was then ceased to let the phases separate. After the phases separated, the organic layer was washed with 5 volumes of half saturated sodium chloride aqueous solution. The organic layer was distilled down to 2 volumes. Tetrahydrofuran (THF) was added, and the organic layer was further distilled down to 1-2 volumes (repeated 3 times), and this step of adding THE and distilling was repeated 3 times before THE was added to a total of 3 volumes. Methanol (MeOH) (45.9 mL, 1.022 M, 3 vol.) was added to the reactor. The resulting slurry was heated to 55-60° C. internal temperature and then cooled to 45-50° C. to obtain a seed bed. MeOH (92 mL, 6 vol.) was added to the seed bed for over 180 minutes. The reactor was cooled down over 4 hours to 20-25° C. The resulting slurry was filtered, and the reactor was rinsed with MeOH. The rinse was then dropped onto the wet cake. The wet cake was transferred to a vacuum oven to dry at 50° C. Compound K1/B1 was isolated as a beige solid and the expected yield was 70%.

Non-limiting examples of alternative reagents and solvents that can be used in the conversion of A1/J1 to B1/K1 are:

Solvents: CPME, IPAc, THF;

Reducing agent: Phenylsilane, polymethylsilane, $PPh_3$; $PPh_3O$;

Catalyst: $(MoO_2Cl_2)DMF_2$ with $PPh_3$ or a silane; 4-methyl-1-phenyl-2,3-dihydrophosphole 1-oxide 4, (2R,5R)-1-{2-[(2R,5R)-2,5-diethylphospholan-1-yl]phenyl}-2,5-diethyl-1-phospholan-1-one, 1-(adamantan-1-ylphosphoroso)adamantane.

Step 2A: Synthesis of 6-bromo-N-(4-fluorophenyl)-1H-indazol-5-amine (B184) and 5-(4-fluorophenyl)-6-isopropyl-1,5-dihydropyrrolo[2,3-f]indazole (T3)

Compound K1/B1 from Step 1A (12.24 g, 39.983 mmol, 1 equiv.) was added to the reactor, followed by copper iodide (CuI) (0.533 g, 2.799 mmol, 0.07 equiv.), bis(triphenylphosphine)palladium(II) dichloride or $Pd(PPh_3)_2Cl_2$ as the catalyst (0.281 g, 0.4 mmol, 0.01 equiv.), and isopropyl alcohol or IPA (97.92 mL, 0.408 M, 8 vol.), and the reaction mixture was stirred. Potassium hydroxide (KOH) (5.608 g, 14.02 mL, 40 w/v %, 99.957 mmol, 2.5 equiv.) was added to the reactor at 18.3° C., and the reaction mixture was purged with nitrogen. Trimethyl(3-methylbut-1-yn-1-yl)silane (7.292 g, 8.103 mL, 0.9 g/mL, 51.977 mmol, 1.3 equiv.) was then added via syringe to the reactor at 15.9° C. The resulting dark solution was purged with nitrogen and then the reaction was heated to 78-80° C. internal temperature (note: reaction, internal temperature at 78.5° C., was refluxing). As part of in-process control (IPC) measures, a sample was taken for analysis. The target was >97% conversion at 230 nm (note: dark solution with some white precipitate). Next, acetic acid (11.405 g, 10.883 mL, 1.048 g/mL, 189.917 mmol, 4.75 equiv.) was charged to the reactor at 77° C. for over 5 minutes. As another IPC measure, another sample was taken to analyze the conversion to T3 as 97.0% at 210 nm or 95.8% at 230 nm. The heating was stopped, and the mixture was stirred at ambient temperature overnight. An aqueous solution of sodium bisulfide ($NaHSO_3$) 10.6 wt % (97.92 mL, 0.408 M, 8 vol.). Isopropyl acetate (IPAc) (122.4 mL, 0.327 M, 10 vol.) was then added to the reactor, followed by water (24.48 mL, 1.633 M, 2 vol.) to dissolve solids. The mixture was heated to 55° C. internal temperature for 2 hours and separated layers were formed, including an aqueous layer having a pH of 4-5 and having light greenish color. An aqueous solution of sodium bisulfide ($NaHSO_3$) 10.6 wt % (55 mL, 0.727 M, 4.493 vol.) was added, and the reaction was stirred at 55° C. internal temperature for 2 hours and a second aqueous layer having a pH of 4-5 and having light greenish color formed. Half saturated ammonium chloride ($NH_4Cl$) (100 mL, 0.4 M, 8.17 vol.) was added to obtain a mixture having pH ~4. Then, an aqueous solution of ammonium hydroxide ($NH_4OH$) (24 mL, 1.666 M, 1.961 vol.) was added, and the mixture was stirred for 30 minutes. Separated layers are once again formed, including an aqueous layer having a pH of 4-5 and a blue color. Half saturated $NH_4Cl$ (100 mL, 0.4 M, 8.17 vol.) was added to the organic phase and stirred for 30 minutes, and then bottom aqueous layer was drained. Next, aqueous acetic acid solution was added to the organic layer, and the organic layer was extracted. A sample of organic layer was taken. The aqueous layer should have a pH of ~5. A solvent swap distillation was then carried out with 5 volumes of toluene, and the mixture was heated to 85° C. internal temperature. Some particulates were observed. 1 volume of toluene was added to the mixture to obtain a solution, which was then cooled down to 45° C. and stirred for 1 hour to form solid precipitates. The mixture was cooled down further to ambient temperature over 2 hours and then stirred for 30 minutes at 24° C. The resulting slurry was filtered, and the reactor with toluene and the wet cake were subjected to drop wash before the material was dried in vacuum oven at 50° C. with nitrogen bleed to afford the product T3 as a solid in 82% yield. The maximum volumes for the aqueous washes in this step were 26-30 volumes.

Step 3: Synthesis of methyl (E)-3-(5-(4-fluorophenyl)-6-isopropyl-1,5-dihydropyrrolo[2,3-f]indazol-7-yl)acrylate (I1)

Step 3 was carried out under the current Good Manufacturing Practices (GMP) guidelines. Compound T3 from Step 2A (1.00 equiv.) was charged with p-toluenesulfonic acid monohydrate (2.00 equiv.) and acetic acid (11 equiv.) or alternatively, camphorsulfonic acid (3.00 equiv, 2.21 w/w equiv.) and dichloromethane (15.0 vol, 19.95 w/w equiv.). The mixture was agitated and heated to 40±5° C. After that, the mixture was charged with ethyl 3,3-dimethoxypropionate (1.50 equiv., 0.705 w/w equiv.), and the mixture was stirred at 40±5° C. for no less than 24 hours. A sample was taken to confirm reaction completion. The mixture was cooled to 25±5° C. An aqueous ~1 M potassium carbonate solution was prepared by stirring potassium carbonate (3.00 equiv., 1.31 w/w equiv.) in water (9.5 vol., 9.50 w/w equiv.) until it dissolved. The prepared 1 M potassium carbonate solution was charged to the vessel, and the mixture was stirred for no less than 30 minutes at a temperature maintained at 25±5° C. The agitation was then stopped to allow the phases to settle for no less than 30 minutes. The bottom organic layer was drained, and both the organic and aqueous phases were sampled. The aqueous layer was discarded, and the organic layer was returned to the reactor. The organic layer was then charged with water (10.0 vol., 10.0 w/w equiv.) and agitated for no less than 1 hour at a temperature maintained at 25±5° C. The agitation was again stopped to allow the phases to settle for no less than 30 minutes. The bottom aqueous layer was drained, and both the organic and aqueous phases were sampled. Once again, the aqueous layer was discarded and the organic layer was returned to the reactor. Agitation was initiated again, vacuum was applied, and the reaction mixture was distilled to a total of 3.0 volumes while maintaining jacket temperature at or below 50° C. (Distillation #1). The distilled mixture was charged with THE (6.0 vol, 5.33 w/w equiv.), vacuum was applied again, and the reaction mixture was distilled to a total of 3.0 volumes while maintaining jacket temperature at or below 50° C. (Distillation #2). The distilled mixture was charged with THE (6.0 vol., 5.33 w/w equiv.), and a sample was taken to test for residual dichloromethane. Vacuum was applied again and the reaction mixture was distilled to a total of 4.0 volumes while maintaining jacket temperature at or below 40° C. (Distillation #3). The distilled mixture was charged with THE (6.0 vol., 5.33 w/w equiv.), and a sample was taken to test for residual dichloromethane. Vacuum was applied again, and the reaction mixture was distilled to a total of 3.0 volumes while maintaining jacket temperature at or below 50° C. (Distillation #4). Polish filtration was then performed. Agitation was initiated again, vacuum was applied, and the reaction mixture was distilled to a total of 6.0 volumes while maintaining jacket temperature at or below 50° C. (Distillation #5). The mixture was heated to 60±5° C. and then cooled to 40±5° C. The cooled mixture was charged with n-heptane (1.0 vol., 0.680 w/w equiv.) over no less than 30 minutes, and then the mixture was stirred at 40±5° C. for no less than two hours. At this point, if nucleation did not occur, an additional 0.5 volumes (0.340 w/w equiv.) of n-heptane was charged over no less than 30 minutes, and the mixture was equilibrated at 40±5° C. for no less than two hours. The mixture was charged with the remaining n-heptane (13.5-14.0 vol.) over 12 hours. After that, the mixture was cooled to 20±5° C. over 4 hours by stirring the slurry at 20±5° C. for no less than 4 hours. The solids were then isolated from the slurry via filtration and the mother liquor was sampled. A wash solution was prepared by mixing tetrahydrofuran (1.0 vol., 0.888 w/w equiv.) and n-heptane (3.0 vol., 2.04 w/w equiv.). The crystallizer was charged with the prepared wash solution and then applied to the wet cake. The wash liquor and the wet cake were sampled. The wet cake was transferred to a vacuum oven at no more than 45° C. until dry. The dried solids, I1, were sampled.

Step 4: Synthesis of methyl 3-(5-(4-fluorophenyl)-6-isopropyl-1,5-dihydropyrrolo[2,3-f]indazol-7-yl) propanoate (H36)

Step 4 was carried out under the current GMP guidelines. I1 from Step 3 (1.82 kg, 1.0 equiv.) was charged to the reactor, and the reactor was purged with nitrogen gas 3 times. The reactor was charged with 5% Pd/C catalyst Johnson Matthey Type A405032-5 or Type A405028-5 (381 g, 10% wt, dry basis) and the reactor was purged again with nitrogen gas 3 times. The reactor was charged with THF (6.4 L, 3.5 vol.), and the reactor was purged with nitrogen gas 3 times. The reactor was evacuated under vacuum and purged once more with nitrogen 3 times. The reactor was charged with tetramethylethylenediamine or TMEDA (1.18 L, 2.1 equiv.), and the reactor was purged with nitrogen gas 3 times. The reactor was heated to 25° C. and pressurized to 3 bar with hydrogen gas. The reaction was stirred until complete conversion was attained as assessed by HPLC (~7-10 hours) and a sample was taken for IPC (expected conversion: >99.5%). The reaction was filtered with a filter aid to remove Pd/C. The reactor was rinsed twice with THE (2 L, 1.1 vol.) and the Celite cake was subjected to drop rinse. The product in THF solution was transferred to a reactor, and the lines were rinsed with 2×1 L THF. While the product solution is light sensitive, the THF solution was stable in the dark for at least a week. The batch was distilled under vacuum at 35° C. down to 2-3 volumes, and then the reactor was charged with ethyl acetate (7.3 L, 4 vol.) and distilled down to 2-3 volumes (repeated 3 times). When the reactor was charged with ethyl acetate (7.3 L, 4 vol.) for the fourth time, the reactor was heated to 70-75° C. to attain full dissolution. The reactor was cooled to 60° C. and then charged with n-heptane (3.6 L, 2.0 vol.) over 30 minutes at 60° C. The batch was stirred for 1 hour to obtain a seed bed. Then, the reactor was charged again with n-heptane (20 L, 11.1 vol.) over 4 hours while maintaining a temperature of 60° C. and stirred for 4 hours. The reactor was then cooled to 20° C. over 5 hours and stirred at the same temperature for no less than 1 hour. The batch was filtered, the reactor was rinsed with n-heptane (2.7 L, 1.5 vol.) and ethyl acetate (0.9 L, 0.5 vol.), and the wet cake was subjected to drop rinse. The wet cake was dried under vacuum at 50-55° C. and H36 was obtained as an off-white solid (~82% yield).

Step 5: Synthesis of Compound 2

Step 5 was carried out under the current GMP guidelines. H36 from Step 4 (1.0 equiv.) was charged to the reactor, followed by ethanol (13 vol.). Agitation was commenced. The reactor was then charged with 40% w/v KOH (2.7 equiv.) over 30 minutes at no higher than 25° C., and the batch at 25° C. was stirred for no less than 3 hours. After stirring, a sample for IPC was taken (average 100.0% conversion; target >99.6% conversion). A polish filtration of the sample was carried out through a 0.45 micron inline filter and acetic acid (2.9 equiv.) was charged through a polish filter to the batch while maintaining a temperature of no higher than 25° C. (note: expected pH range of 6-7). The reaction was then heated to 50° C., and the reactor was charged with purified water (12.4 vol.) through a polish filter for over 2 hours. Next, the reactor was cooled to 20° C. internal temperature over 5 hours. The batch was filtered, and the reactor was charged with a solution of EtOH (1.0 vol.) and water (1.0 vol.) through a polish filter. The filter cake was washed with the ethanol-water solution and then with purified water (2.0 vol.). The wet cake was dried under vacuum at 50° C. and Compound 2 was obtained as an off-white solid. In this step, the maximum volume for precipitation after the addition of water was 28 volumes.

Optional Re-Crystallization of Compound 2 for Form Conversion

To Compound 2 obtained from Step 5 was added THF (5.0 vol., 4.45 w/w equiv.). The mixture was heated to 55±5° C., then cooled to 42° C. Jet-milled Compound 2 seed material was then charged (0.05 w/w equiv.), and the mixture was held for no less than 3 hours. A sample was taken to confirm the desired form (Compound 2 Form C) by X-ray powder diffraction (XRPD). The sample was then filtered to isolate the solids from the supernatant. The solids were charged with n-heptane (2.5 vol., 1.71 w/w equiv.) at an approximately linear rate of addition for no less than 20 hours at 42° C. A sample was taken again for IPC purposes, and the sample was filtered to isolate the solids from the supernatant. The solids were charged with n-heptane (2.5 vol., 1.71 w/w equiv.) again, at an approximately linear rate of addition for no less than 16 hours at 42° C. A sample was taken again for IPC purposes, and the sample was filtered to isolate the solids from the supernatant. The solids were cooled to 25±3° C. for no less than 4 hours and then stirred at the same temperature for no less than 1 hour. A sample was taken again for IPC purposes, and the sample was filtered to isolate the solids from the supernatant. The solids were further purified via centrifugation or filtration. If possible, a mass for the mother liquor was obtained and sampled. A wash solution was prepared by mixing THE (1.8 vol., 1.60 w/w equiv.) and n-heptane (2.2 vol., 1.50 w/w equiv.). The reaction vessel was rinsed with the prepared wash solution and applied to the filter cake. If possible, a mass for the wash liquor was obtained and sampled. The solids were dried at 60° C. under nitrogen and sampled.

Alternative preparation of 6-bromo-N-(4-fluorophenyl)-1H-indazol-5-amine (1H184) and 5-(4-fluorophenyl)-6-isopropyl-1,5-dihydropyrrolo[2,3-f]indazole (T3)

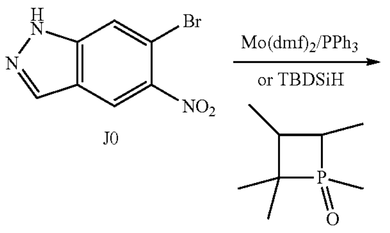

J0

-continued

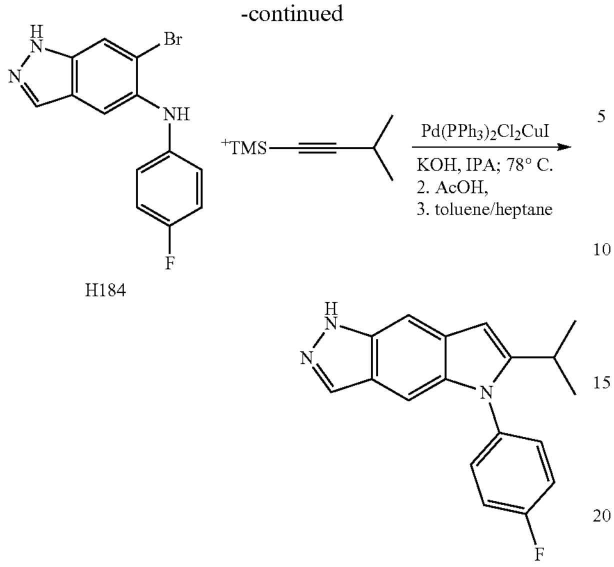

H184

T3

Step 1: Synthesis of 6-bromo-N-(4-fluorophenyl)-1H-indazol-5-amine (1H184) and 5-(4-fluorophenyl)-6-isopropyl-1,5-dihydropyrrolo[2,3-f]indazole (T3)

A mixture of J0 (also referred to as A0 herein, 3.0 kg, 11.5 mol), 4-fluorophenylboronic acid (2.64 kg, 18.9 mol), triphenylphosphine (7.16 kg, 27.3 mol), $MoO_2Cl_2$(dmf) (235 g, 0.63 mol), 2,2'-dipyridyl (100 g, 0.64 mol) and toluene (30 L) was heated to 93-99° C. over 16 hours. The mixture was cooled to 23° C., and a mixture of 45% KOH (3.2 L, 37 mol) in water (15 L) was added. The mixture was stirred for 20 minutes, then allowed to settle. The layers were separated, and the upper organic was washed with a mixture of water (12 L) and saturated brine (4 L). The mixture was filtered through a pad of Celite, rinsing with toluene (7 L), and then the layers were separated. The organic layer was diluted with MTBE (39 L), then stirred with silica (3 kg) and magnesium chloride (6 kg) for 16 hours at 22-28° C. The slurry was filtered though a pad of 6 kg silica, washing with 1:1 toluene:MTBE (70 L). The main filtrate was concentrated to dryness to afford crude H184 (4.6 kg wet weight) as a pale brown solid. A solution of crude H184 (4.6 kg, 8.8 mol) and p-TSA (1.51 kg, 7.9 mol) in THE (20 L) was heated to 60-65° C. and toluene (20 L) was added over 20 min via pump. The resulting slurry was stirred at 60-65° C. for 30 minutes, then was cooled to 15-20° C. and stirred for 1 hour. The solid was collected by filtration to give the p-TSA salt (2.46 kg, 5.1 mol) as a yellow, crystalline solid. The procedure was repeated with 6 kg of J/A0. The p-TSA salt (3.6 kg, 7.5 mol) was charged to the reactor, followed by 2-MeTHF (35 L) and agitated until the solids dissolved. The organic phase was washed with water (2×20 L), 2N NaOH (2×20 L) and brine (10 L) and the organics dried over sodium sulfate. Solids were filtered off, and the mixture was concentrated in vacuo to afford H184 (2.1 kg) as a tan solid. Overall, 9 kg of J0/A0 (~93% purity, 34.6 mol) was converted to 5.29 kg H184 (17.3 mol, 50% yield).

$^1$H NMR (400 MHz, DMSO-$d_6$) δ 13.06 (s, 1H), 7.99 (d, J=1.1 Hz, 1H), 7.89 (d, J=1.0 Hz, 1H), 7.60 (s, 1H), 7.47 (s, 1H), 7.04-6.94 (m, 2H), 6.84-6.73 (m, 2H).

Step 2: Synthesis of 5-(4-fluorophenyl)-6-isopropyl-1,5-dihydropyrrolo[2,3-f]indazole (T3)

H184 (12.24 g, 39.983 mmol, 1 equiv.), copper iodide (0.533 g, 2.799 mmol, 0.07 equiv) and $Pd(PPh_3)_2Cl_2$ (0.281 g, 0.4 mmol, 0.01 equiv.) were suspended in degassed IPA (97.92 mL, 0.408 M, 8 vols). Potassium hydroxide (5.608 g, 14.02 mL, 40 w/v %, 99.957 mmol, 2.5 equiv.) was added, and the reaction was purged with nitrogen. Trimethyl(3-methylbut-1-yn-1-yl)silane (7.292 g, 8.103 mL, 0.9 g/mL, 51.977 mmol, 1.3 equiv.) was added via syringe, and the mixture was purged with nitrogen. The reaction was heated to 75-80° C. internal temperature. Upon reaction completion, acetic acid (11.405 g, 10.883 mL, 1.048 g/mL, 189.917 mmol, 4.75 equiv.) was charged at 77° C. over 5 minutes, and the reaction stirred for at least 2 hours. The reaction was cooled to ambient temperature and aqueous $NaHSO_3$ 10.6 wt % (97.92 mL, 0.408 M, 8 Vols) was added followed by IPAC (122.4 mL, 0.327 M, 10 vols.). Water (24.48 mL, 1.633 M, 2 Vols) was added, and the mixture was heated to 55° C. for 2 hours. The mixture was cooled, and the phases were separated. The organic layer was treated with aqueous $NaHSO_3$ 10.6 wt % (55 mL, 0.727 M, 4.493 vols) at 55° C. The mixture was cooled to ambient temperature and the phases separated. The organic layer was treated with a mixture of half saturated aqueous $NH_4Cl$ (100 mL, 0.4 M, 8.17 vols) and aqueous $NH_4OH$ (24 mL, 1.666 M, 1.961 vols). The layers were separated, and the organic layer treated with half saturated aqueous $NH_4Cl$ (100 mL, 0.4 M, 8.17 vols). The layers were separated, and the organic layer were treated with acetic acid to obtain pH 5. The organic layer was separated and a solvent swap to toluene was performed. The product was isolated from 6 volumes of toluene by heating the mixture to 85° C. internal temperature. The solution was then cooled down to 45° C. and stirred for 1 hour to form solid precipitates. The mixture was cooled down further to ambient temperature over 2 hours and then stirred for 30 minutes at 24° C. The resulting slurry was filtered, and the reactor with toluene and the wet cake were subjected to drop wash before the material was dried in vacuum oven at 50° C. with nitrogen bleed to afford the product T3 as a solid in 63% yield.

Example 6: Large-Scale Synthesis of Compound 2-5-Bromo-6-Iodo-1H-Indazole as Starting Material Scheme 8 depicts a large-scale synthesis of Compound 2 that utilizes 5-bromo-6-iodo-1H-indazole (H7) as the starting material. This process is expected to yield a solid form of Compound 2 or a pharmaceutically acceptable salt thereof at an amount of at least about 300 kg.

Scheme 8

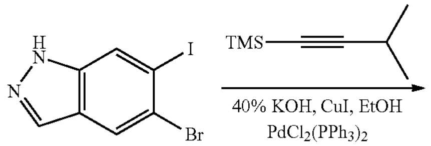

H7

Step 1B

-continued

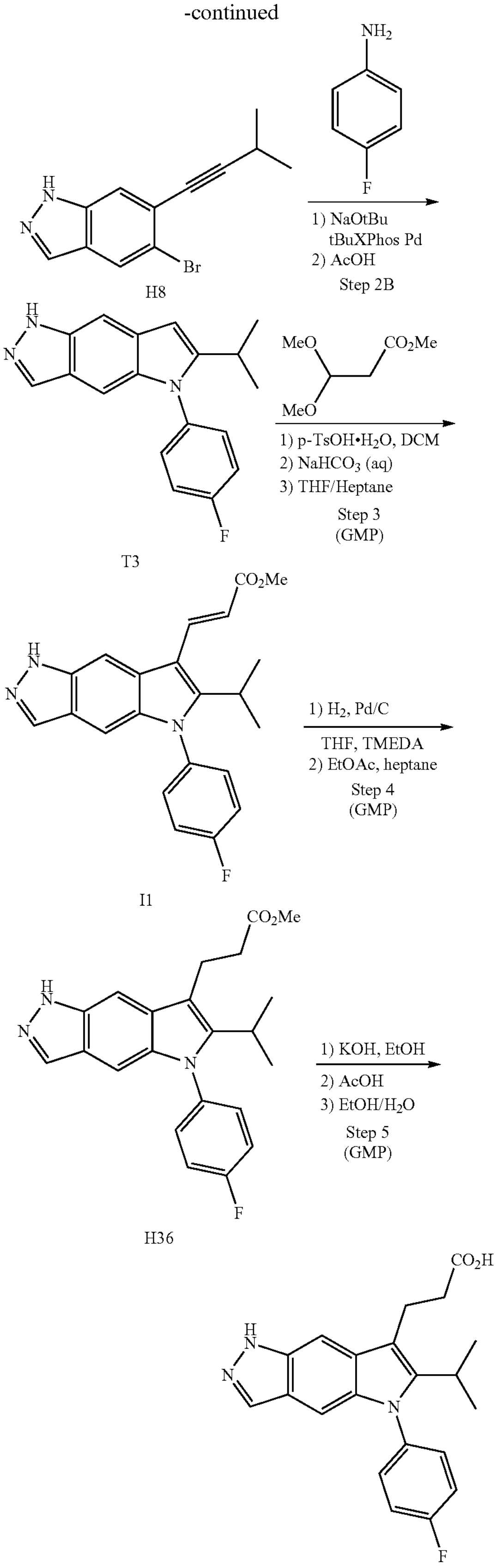

H8

T3

I1

H36

Compound 2

Step 1B: Synthesis of 5-bromo-6-(3-methylbut-1-yn-1-yl)-1H-indazole (H8)

The starting material 5-bromo-6-iodo-1H-indazole (17) (1.00 equiv., 1.00 w/w equiv.) was added to the reactor, followed by CuI (0.100 equiv., 0.0590 w/w equiv.) and the bis(triphenylphosphine)Pd dichloride (0.001 equiv., 0.0043 w/w equiv.) catalyst. Ethanol (5.00 vol., 3.95 w/w equiv.) was added to the reactor, and agitation was started. The temperature was adjusted to 20±5° C. An aqueous potassium hydroxide solution was prepared by charging potassium hydroxide (2.10 equiv.) and a total water charge of 1.04 volumes (1.04 w/w equiv.). The aqueous potassium hydroxide solution was added to the reactor, and the temperature was maintained at 20±5° C. Instead of potassium hydroxide, the previously disclosed processes as depicted in Scheme 2 employed di- or triethylamine as the base. The reaction vessel was made inert with nitrogen gas while stirring the mixture by performing pressure-purge cycles or evacuation-purge cycles 3 to 4 times. An ammonium hydroxide solution (28-30 wt %, 0.500 equiv., 0.194 wt equiv.) was added to the reactor, and the temperature was maintained at 20±5° C. Trimethyl(3-methylbut-1-yn-1-yl)silane (1.20 equiv., 0.521 w/w equiv.) was added to the reactor while the temperature was maintained at 20±5° C. Instead of trimethyl(3-methyl-but-1-yn-1-yl)silane, H7 was reacted with 3-methylbut-1-yne in the previously disclosed processes as depicted in Scheme 2.

The reaction vessel was made inert again with nitrogen gas while the mixture was stirred by performing pressure-purge cycles or evacuation-purge cycles 1 to 2 times. The mixture was heated to 75±5° C., stirred for the no less than 24 hours, and an IPC sample was taken to confirm reaction completion (IPC-1). While this IPC step was taken, the reaction vessel was made inert again with nitrogen gas. If the IPC target was not met, the reaction was stirred further for no less than 1 hour and re-sampled. After the IPC target was met, the reaction mixture was cooled to 25±5° C. and then concentrated to ~3.0 volumes. The concentrated mixture was charged with dichloromethane (5.0 vol., 6.64 w/w equiv.). A 20 wt % solution of aqueous ammonium chloride (9.0 vol. total) was added to the reaction while maintaining the temperature at 25±5° C. The resulting biphasic mixture was stirred at 25±5° C. for no less than 0.5 hours. The agitation was stopped to allow the phases to settle for no less than 0.5 hours. The bottom organic phase was drained first from the reactor, followed by the top aqueous phase, and both phases were sampled. The organic phase was returned to the reactor and agitation was commenced. The temperature of the organic phase was adjusted to 25±5° C. The remaining 3.0 volumes of the aqueous ammonium chloride solution were added to the organic phase, while the temperature was maintained at 25±5° C. The steps of stirring the biphasic mixture, ceasing the agitation to allow settling of phases, draining and sampling phases, and returning of the organic phase to the reactor were repeated. A solution with water (2.0 vol., 2.00 w/w equiv.) and 8.5 wt % phosphoric acid (0.03 vol., 0.0313 w/w equiv.) was prepared and the prepared phosphoric acid solution was added to the organic phase, followed by 1 M HCl (0.14 vol., 0.143 w/w equiv.), while the temperature was maintained at 25±5° C. The steps of stirring the biphasic mixture, ceasing the agitation to allow settling of phases, draining and sampling phases, and returning of the organic phase to the reactor were repeated once more. Water (2.0 vol., 2.00 w/w equiv.) was added to the organic phase while the temperature was maintained at 25±5° C. The steps of stirring the biphasic mixture, ceasing the agitation to allow settling of phases, draining and sampling phases, and returning of the organic phase to the reactor were repeated yet another time. Vacuum was applied, and the reaction mixture was distilled to a total of 3 volumes while maintaining internal temperature at or below 35° C., followed by addition of dichloromethane (4.0 vol., 5.31 w/w equiv.) and sampling for residual ethanol and water content (repeated 3 times). Next, the mixture was heated to 35±5° C. and stirred for no less than 15 minutes, charged with n-heptane (2.6 vol., 1.78 w/w equiv.), then heated to 40±5° C. N-heptane (2.0 vol., 1.37 w/w equiv.) was added again over no less than 30 minutes while maintaining the temperature at 40±5° C. The batch was stirred for no less than 30 minutes and monitored for formation of nucleated solids. If solids nucleated, n-heptane (7.7 vol., 5.27 w/w equiv.) was added over no less than 12 hours. If solids did not nucleate, the batch was cooled to 35±5° C. and stirred for no less than 1 hour before n-heptane was added over no less than 12 hours. The batch was cooled to 20±5° C. over no less than 7 hours and then stirred at 20±5° C. for no less than 2 hours. The solids were isolated via filtration or centrifugation, and the mother liquor was sampled. A wash solution was prepared by mixing dichloromethane (0.75 vol., 0.995 w/w equiv.) and n-heptane (2.25 vol., 1.54 w/w equiv.). The wet cake was washed with the prepared wash solution, and the wash liquor and wet cake were both sampled. N-heptane (3.0 vol., 2.05 w/w equiv.) was added to the wet cake, vacuum was applied, and the wash liquor was sampled (repeated twice). The solids were dried under vacuum at a jacket temperature of 50±5° C. After drying, the jacket was cooled and the solid was discharged. The solid, H8, was sampled for palladium and copper analysis. The maximum batch volumes in Step 1B were 14 volumes through the aqueous washes and 17 volumes during the crystallization.

Step 2B: Synthesis of 5-(4-fluorophenyl)-6-isopropyl-1,5-dihydropyrrolo[2,3-f]indazole (T3)

Sodium tert-butoxide (NaOtBu) was mixed with ethanol (8.0 vol., 6.31 w/w equiv.), agitation was started, and the mixture was cooled to 20±5° C. H8 from Step 1B was added to the mixture, followed by 4-fluoroaniline (1.13 equiv., 0.477 w/w equiv.), and the mixture was added into the reactor. Agitation was commenced, and the temperature was adjusted to 20±5° C. The initial reactor and lines were rinsed with ethanol. The reaction mixture was deoxygenated with four vacuum-nitrogen cycles. tBuXPhos Pd G3 (0.03 equiv., 0.091 w/w equiv.) was added to the mixture as a catalyst, and the mixture was deoxygenated two more times as described above. The reaction mixture was heated to 65±5° C. and stirred at the same temperature for no less than 2.5 hours, then sampled for reaction completion. The mixture was cooled to 55±5° C. and charged with acetic acid (4.75 equiv., 1.08 w/w equiv.) while maintaining batch temperature at no higher than 60° C. The mixture was stirred at 55±5° C. for no less than 4 hours and sampled for reaction completion. The mixture was cooled to 20±5° C. 2-methyltetrahydrofuran (2-MeTHF) (8.0 vol., 6.83 w/w equiv.) was added into the reactor, and the mixture was stirred at 20±5° C. for no less than 30 minutes. The slurry was filtered over Celite to obtain the filtrate. The reactor and wet cake were rinsed with 2-MeTHF (2.0 vol., 1.71 w/w equiv.), and vacuum was applied to obtain the rinsed filtrates. The filtrates were combined and then sampled. Then, the solution was heated to 50±5° C. with agitation. An aqueous saturated sodium bisulfite solution for 2 aqueous washes was prepared by stirring sodium bisulfite in water until it dissolved (no less than 20 volumes). Half of the prepared saturated sodium bisulfite solution (10.0 vol.) was added to the vessel maintaining the temperature at 50±5° C., and the mixture was stirred at 50±5° C. for no less than 1 hour. The agitation was stopped to let the phases settle for no less than 30 minutes, and then the bottom aqueous layer was drained. Both the organic and aqueous phases were sampled. The treatment of the mixture was repeated with the second half of the sodium bisulfite solution, and the steps of letting the phases settle without agitation, sampling of the phases, and draining the bottom aqueous layer were also repeated. Next, the organic layer was agitated and cooled to 20±5° C., and toluene (1.5 vol., 1.30 w/w equiv.) was added to the reactor, followed by water (10.0 vol) while maintaining the temperature at 20±5° C. The mixture was stirred at 20±5° C. for no less than 30 minutes. Then, the steps of letting the phases settle without agitation, sampling of the phases, and draining the bottom aqueous layer were repeated. The organic layer was agitated again and water (10.0 vol.) was added to the reactor while maintaining the temperature at 20±5° C. The steps of letting the phases settle without agitation, sampling of the phases, and draining the bottom aqueous layer were repeated once more. The organic layer was polish-filtered to remove any residual solids and then the solution was transferred to a clean, dried vessel. The filtered organic phase was then sampled. Agitation and vacuum were applied, and the reaction mixture was distilled to a total of 4.0 volumes while maintaining jacket temperature at or below 40° C. and then toluene (6.0 vol., 5.20 w/w equiv. for the first two distillations, then 5.0 vol., 4.34 w/w equiv. for the third distillation) was added (repeated 3 times). After the second and third distillations, the mixtures were sampled for residual 2-MeTHF and ethanol. The solution was stirred and heated to 90±5° C., then cooled to 75±3° C. The solution was then stirred at 75±2° C. for no less than 1 hour. If self-nucleation was not observed, the solution was heated to 70±3° C. and stirred for an additional 1 hour before proceeding to the next step of cooling the reaction mixture to 20±5° C. over 12 hours. The resulting slurry was stirred at 20±5° C. for no less than 5 hours, and then sampled via microscopy. The solids were isolated from the slurry via filtration or centrifugation, and the mother liquor was sampled. Toluene (4.0 vol., 3.47 w/w equiv.) was added to the crystallizer and then applied to the wet cake. The wash liquor and wet cake were both sampled. The wet cake was transferred to a drying equipment to dry at no more than 50±5° C. until a constant loss on drying (LOD) was obtained. The dried solid, T3, was sampled. The maximum volumes used in Step 2B were: 31 volumes for the aqueous washes, 9 volumes for the crystallization.

Steps 3-5: Synthesis of methyl (E)-3-(5-(4-fluorophenyl)-6-isopropyl-1,5-dihydropyrrolo[2,3-f]indazol-7-yl)acrylate (I1), methyl 3-(5-(4-fluorophenyl)-6-isopropyl-1,5-dihydropyrrolo[2,3-f]indazol-7-yl) propanoate (H36), and Compound 2

The remaining Steps 3, 4, and 5 of the process depicted in Scheme 8 were as described above (i.e., Steps 3, 4, and 5 of the process depicted in Scheme 7B).

Optional Re-Crystallization of Compound 2 for Form Conversion

The re-crystallization procedure described also applies to Compound 2 as prepared using the process depicted in Scheme 8.

Example 7: Assays for Detecting and Measuring AAT Modulator Properties

A. AAT Function Assay (MSD Assay NL20-SI Cell Line)

Alpha-1 antitrypsin (AAT) is a SERPIN (serine protease inhibitor) that inactivates enzymes by binding to them covalently. This assay measured the amount of functionally active AAT in a sample in the presence of Compound 1 or Compound 2 by determining the ability of AAT to form an irreversible complex with human neutrophil Elastase (hNE). In practice, the sample (cell supernatant, blood sample, or other) was incubated with excess hNE to allow AAT-Elastase complex to be formed with all functional AAT in the sample. This complex was then captured using a microplate coated with an anti-AAT antibody. The complex captured on the plate was detected with a labeled anti-Elastase antibody and quantitated using a set of AAT standards spanning the concentration range present in the sample. A Meso Scale Discovery (MSD) plate reader, Sulfo-tag labeling, and microplates were used to provide high sensitivity and wide dynamic range.

MATERIALS:

| Reagents/Plates | Concentration |
|---|---|
| Goat anti-human Alpha-1-Antitrypsin<br>Polyclonal Antibody<br>Use at 5 μg/mL in phosphate buffered saline (PBS) | 1 mL at 1 mg/mL |
| Human Neutrophil Elastase<br>Stock at 3.4 μM (0.1 mg + 1 mL PBS)<br>Working at 1 μg/mL (34 nm) in MSD Assay buffer (1% bovine serum albumin (BSA)) | 100 μg lyophilized |
| Mouse anti-human Neutrophil Elastase Monoclonal Antibody<br>Sulfo-tagged @ 12:1 using MSD Gold Sulfo-tag<br>N-hydroxysuccinimide (NHS) ester; use at 0.45 μg/mL in MSD Assay buffer (1% BSA) | 900 μg/mL |
| M-AAT (Alpha-1-Antitrypsin)<br>5 mg lyophilized | |
| MSD Blocker A (BSA)<br>5% solution in PBS for blocking<br>1% solution in PBS for assay buffer | 250 mL |
| MSD Read Buffer T (4X) with Surfactant | 1 L or 250 mL |
| MSD 384 high bind plates | |
| Polypropylene for dilution 384 well plate | |
| Tissue culture treated black well 384 well plate | |

Instrument(s):
- Meso Sector S600
- Bravo
- Washer dispenser
- Multidrop Combi

Assay Protocol

Day 1 Cell Culture
1. Harvest NL20 human bronchial epithelial cells expressing human Z-AAT in OptiMEM™ containing Pen/Strep (P/S).
2. Seed at 16,000 cells/well in 30 μL (384 well plate).
3. Centrifuge plates briefly up to speed (1200 rpm) and place into 37° C. incubator overnight.

Day 2: Compound Addition and Coating Plates with Capture Antibody Compound Addition:
1. Dispense 40 μL of OptiMEM™ (P/S) with doxycycline (1:1000 stock=0.1 μM final) to each well of the compound plate using a multidrop Combi in hood.
2. Remove cell plate from incubator, flip/blot, and take immediately to Bravo to transfer compounds.
3. Return plates to incubator overnight.

Coat MSD Plates
1. Dilute capture antibody (Polyclonal Goat anti-AAT) to 5 g/mL (1:200) in PBS (no BSA).
2. Dispense 25 L of diluted capture antibody into all wells of MSD 384-well High Bind plate using the Multidrop equipped with a standard cassette.
3. Incubate overnight at 4° C.

Prepare Blocker A (BSA) Solutions
1. Prepare solution of 5% MSD Blocker A (BSA) following the manufacturer's instructions.
2. Further dilute the 5% MSD Blocker A in PBS to 1% (Blocker A) as needed.

Day 3: Run MSD Assay

Block Plates
1. Wash plate 1× with 50 μL Wash buffer (PBS+0.5% Tween 20), and add 35 μL 5% Block A buffer to block non-specific binding on washer dispenser.
2. Rotate plates on shaker for 1 hour at 600 rpm.

Prepare M-AAT Standards
1. Dilute M-AAT stock to 1.6 μg/mL in 1% BSA Blocker A (Stock in −70° C.); then prepare 12×1:2 serial dilutions in 1% Blocker A.
2. The top starting final concentration on MSD plate is 320 ng/mL. These dilutions correspond to a final concentration of 320, 160, 80, 40, 20, 10, 5, 2.5, 1.25, 0.625, 0.312, 0.156 ng/mL.

Dilution Plate
1. Add 80 μL of 1% Assay buffer to all wells except columns 1/24 (standards) with Multidrop Combi.
2. Add diluted standards to columns 1 and 24.
3. Centrifuge dilution plates 1200 rpm briefly.

Cell Plate
1. Aspirate columns which will have the standards from the cell plates in the hood using 16-pin aspirator.

Prepare Human Neutrophil Elastase (hNE)
1. Prepare 1 g/mL Human Neutrophil Elastase by diluting in 1% Blocker A.
   a. Small 100 μg vial—add 1 mL PBS (100 μg/mL)
      i. This can then be diluted 1:100 in 1% Assay Buffer for a final 1 μg/mL concentration.

MSD—Add hNE (20 μL/Well)
1. After the MSD plate has blocked for at least 1 hour, wash plate 1× with 50 μL. Wash buffer (PBS+0.5% Tween 20) and then add 20 μL hNE to each well.

Bravo—Cell Plate—Dilution Plate—MSD Plate

Using the Bravo aspirate 10 μL from the cell plate, transfer to the dilution plate (9-fold dilution).

1. Mix 25 μL 3×, then aspirate 5 μL, transfer to MSD plate (5-fold dilution).
2. Mix 10 μL 3×. Total dilution is 45-fold.
3. Shake plates at 600 rpm for 1.5 hours.

Add Functional Detection hNE Antibody

1. Wash plate 1× with wash buffer.
2. Add 25 L Sulfo-tagged anti-Elastase Monoclonal Mouse anti-Elastase) diluted to 0.45 g/mL (1:2000) in 1% Blocker A into all wells of the functional activity MSD plates using the washer/dispenser.
   Note: The dilution required for sufficient signal must be determined for each new lot of labeled antibody.
3. Incubate at RT shaking at 600 rpm for 1 hour.

Final Wash and MSD Imager Read

1. Wash the plate 1×, and add 25 μL of Wash Buffer to the plate.
2. Make 2× Read buffer.
3. Remove wash buffer from MSD plate.
4. Transfer 35 μL 2× Read Buffer to MSD plate using Bravo and take to MSD to read immediately.
   Data analysis in MSD Discovery Workbench 4.0 software and $EC_{50}$ values were determined using Genedata.

B. Biochemical Assay (Z-AAT Elastase Activity Assay)

This assay measured the modulation of Compound 1 or Compound 2 on Z-AAT SERPIN activity using purified Z-AAT protein and purified human neutrophil elastase (hNE). Normally, when active monomeric Z-AAT encounters a protease such as trypsin or elastase, it forms a 1:1 covalent "suicide" complex in which both the AAT and protease are irreversibly inactivated. However, compounds binding to Z-AAT can lead to a decrease in SERPIN activity. In such cases, when a protease encounters compound-bound Z-AAT, the protease cleaves and inactivates Z-AAT without itself being inactivated.

Materials

Reagents

- PBS buffer (media prep)+0.01% BRIJ35 detergent (Calbiochem Catalog No. 203728)
- Opti-MEM media (Fisher Catalog No. 11058-021)
- Human neutrophil elastase (hNE, Athens Research Catalog No. 16-14-051200)
  - 3.4 M stock (0.1 mg/mL) prepared in 50 mM Na Acetate, pH 5.5, 150 mM NaCl, stored at −80° C.
- Elastase substrate V (ES V, fluorescent peptide substrate MeOSuc-Ala-Ala-Pro-Val-AMC, Calbiochem Catalog No. 324740)
  - 20 mM stock in DMSO, stored at −20° C.
- Purified Z-AAT protein from human plasma;
  - 12.9 M (0.67 mg/mL) Z-AAT Vertex Cambridge Sample 4942, from patient #061-SSN, stored at −80C Plates

- Corning 4511 (384 well black low volume)

Instruments

- PerkinElmer® EnVision™

Assay Protocol

Pre-Incubation of Z-AAT with Compounds 1. 7.5 μL of Z-AAT (20 nM) was incubated with Compound 1 or Compound 2 in a GCA plate for 1 hour at room temperature.

Addition of hNE 1. 7.5 μL of HNE solution (3 nM in PBS+0.01% BRIJ35) added into GCA plate.
2. Incubate plate for 30 minutes to allow Z-AAT/HNE suicide complex formation.

Addition of substrate and read plate on PE Envision 1. 7.5 μL of substrate (300 μM solution of elastase substrate (ES V) in PBS+0.01% BRIJ35) dispensed per well into GCA plate.
2. Immediately read on Envision.

C. $IC_{50}$ and $EC_{50}$ Data for Compounds 1 and 2

Compound 1 and Compound 2 are useful as modulators of AAT activity. The $IC_{50}$ of Compound 1 (Z-AAT elastase activity) is greater than 1.0 M. The $EC_{50}$ (NL20 function) of Compound 1 is less than 0.4 M. The $IC_{50}$ of Compound 2 (Z-AAT elastase activity) is greater than 1.0 μM. The $EC_{50}$ (NL20 function) of Compound 2 is less than 0.4 μM.

OTHER EMBODIMENTS

This disclosure provides merely exemplary embodiments of the disclosed subject matter. One skilled in the art will readily recognize from the disclosure and accompanying figures and claims that various changes, modifications, and variations can be made therein without departing from the spirit and scope of the inventive subject matter as defined in the following claims.

What is claimed is:

1. A process for preparing a solid form of Compound 1

(Compound 1)

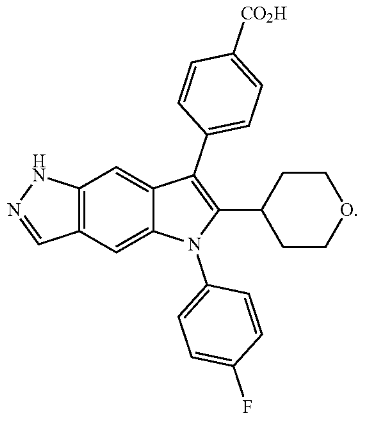

or a pharmaceutically acceptable salt thereof, comprising:

(a) reacting

B1

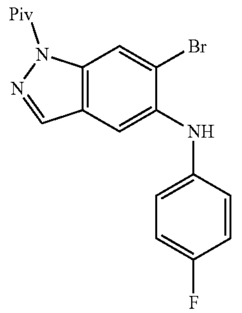

or a pharmaceutically acceptable salt thereof with

D1

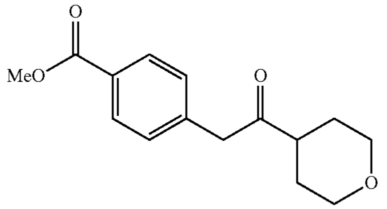

to form

C58B

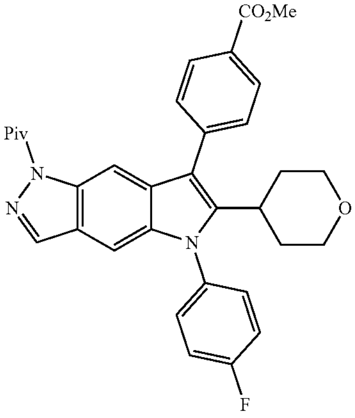

or a pharmaceutically acceptable salt thereof; and (b) de-esterifying C58B or a pharmaceutically acceptable salt thereof to yield the solid form of Compound 1 or a pharmaceutically acceptable salt thereof.

2. The process according to claim 1, wherein (i) step (a) comprises reacting B1 or a pharmaceutically acceptable salt thereof with D1 in the presence of a palladium-phosphine complex-based catalyst that is bis(tri-t-butylphosphine) Pd and a base that is potassium carbonate and wherein the reaction is optionally carried out at about 75° C.; or (ii) step (a) comprises reacting B1 or a pharmaceutically acceptable salt thereof with D1 in the presence of a solvent that is 2-methyltetrahydrofuran and wherein the reaction is optionally carried out at about 75° C.; or (iii) step (a) comprises reacting B1 or a pharmaceutically acceptable salt thereof with D1 in the presence of a palladium-phosphine complex-based catalyst that is bis(tri-t-butylphosphine) Pd and a base that is potassium carbonate and in the presence of 2-methyltetrahydrofuran and wherein the reaction is optionally carried out at about 75° C.

3. The process according to claim 1, wherein step (b) comprises de-esterifying C58B or a pharmaceutically acceptable salt thereof with a base that is sodium hydroxide and in the presence of a solvent that is tetrahydrofuran; and wherein step (b) is optionally carried out at about 55-65° C.

4. The process according to claim 1, wherein the process further comprises an additional step selected from:

step (a1) reacting

A0

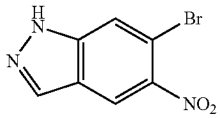

or a pharmaceutically acceptable salt thereof with pivaloyl chloride to form A1 or a pharmaceutically acceptable salt thereof, wherein the reaction is optionally carried out in the presence of a base that is sodium tert-amylate and a solvent that is tetrahydrofuran; and wherein the reaction is optionally carried out at about 10-20° C.; and/or step (a2) reacting

A1

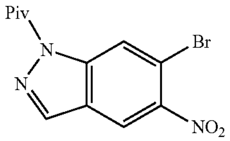

or a pharmaceutically acceptable salt thereof with 4-fluorophenylboronic acid to form B1 or a pharmaceutically acceptable salt thereof, wherein the reaction is optionally carried out in the presence of (1) a reducing agent that is dimethylsilyloxy(dimethyl)silane; or (2) a phosphetane oxide catalyst that is hexamethyloxophosphetane and a solvent that is toluene; and wherein the reaction is optionally carried out at about 90° C.

5. The process according to claim 1, wherein the process further comprises an additional step selected from:

step (b1) reacting

F1

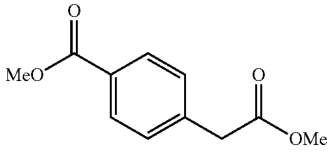

with oxane-4-carbonyl chloride to form

E1

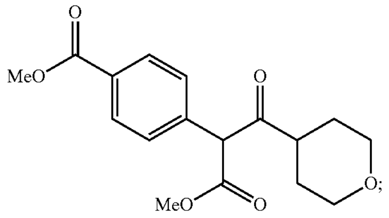

wherein step (b1) is optionally carried out in the presence of a base that is potassium tert-butoxide and a solvent that is tetrahydrofuran; and/or step (b2) reacting

E1

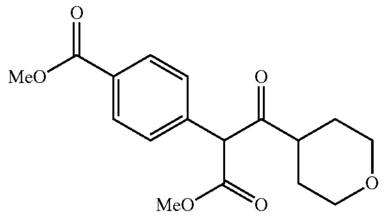

with a sodium chloride aqueous solution to form

D1

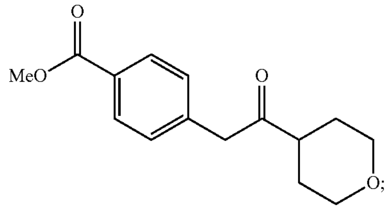

wherein step (b2) is optionally carried out in the presence of in the presence of a solvent that is dimethyl sulfoxide; and wherein step (b2) is optionally carried out at about 150° C.

* * * * *